(12) United States Patent
Dekker et al.

(10) Patent No.: US 9,657,301 B2
(45) Date of Patent: *May 23, 2017

(54) FILAMENTOUS FUNGAL MUTANTS WITH IMPROVED HOMOLOGOUS RECOMBINATION EFFICIENCY

(71) Applicant: DSM IP ASSETS B.V., Heerlen (NL)

(72) Inventors: Petrus Jacobus Theodorus Dekker, Echt (NL); Marco Alexander van den Berg, Echt (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/980,425

(22) Filed: Dec. 28, 2015

(65) Prior Publication Data

US 2016/0130589 A1    May 12, 2016

Related U.S. Application Data

(62) Division of application No. 10/594,014, filed as application No. PCT/EP2005/051464 on Mar. 31, 2005, now Pat. No. 9,243,043.

(30) Foreign Application Priority Data

Apr. 2, 2004 (EP) .................... 04076057

(51) Int. Cl.
*C12N 1/14* (2006.01)
*C12N 15/00* (2006.01)
(Continued)

(52) U.S. Cl.
CPC ............. *C12N 15/80* (2013.01); *C07K 14/37* (2013.01); *C12N 15/902* (2013.01); *C12P 17/10* (2013.01);
(Continued)

(58) Field of Classification Search
CPC .......... C12N 15/80; C12P 21/00; C12P 21/37; C07K 14/38
See application file for complete search history.

(56) References Cited

U.S. PATENT DOCUMENTS 5,464,764 A    11/1995 Capecchi
5,627,059 A    5/1997 Capecchi
(Continued)

FOREIGN PATENT DOCUMENTS

EP    0 166 601    1/1986
EP    20040076057.1    4/2004
(Continued)

OTHER PUBLICATIONS

Baxevanis et al., "Bioinformatics—A Practical Guide to the Analysis of Genes and Proteins", Wiley-Interscience, 2001, pp. 202-204, John Wiley & Sons, Inc., New York, NY.
(Continued)

*Primary Examiner* — Yong Pak
(74) *Attorney, Agent, or Firm* — McBee Moore Woodward & Vanik IP, LLC

(57) ABSTRACT

The present invention relates to a method for increasing the efficiency of targeted integration of a polynucleotide to a pre-determined site into the genome of a filamentous fungal cell with a preference for NHR, wherein said polynucleotide has a region of homology with said pre-determined site, comprising steering an integration pathway towards HR. The present invention also relates to a mutant filamentous fungus originating from a parent cell, said mutant having an HR pathway with elevated efficiency and/or an NHR pathway with a lowered efficiency and/or a NHR/HR ratio with decreased efficiency as compared to said HR and/or NHR efficiency and/or NHR/HR ratio of said parent cell under the same conditions.

14 Claims, 5 Drawing Sheets

(51) Int. Cl.

| | |
|---|---|
| *C12Q 1/68* | (2006.01) |
| *C12N 9/00* | (2006.01) |
| *C12P 21/04* | (2006.01) |
| *C07H 21/04* | (2006.01) |
| *C07K 1/00* | (2006.01) |
| *C12N 15/80* | (2006.01) |
| *C07K 14/37* | (2006.01) |
| *C12N 15/90* | (2006.01) |
| *C12P 21/02* | (2006.01) |
| *C12P 23/00* | (2006.01) |
| *C12P 37/00* | (2006.01) |
| *C12P 17/10* | (2006.01) |
| *C12P 21/00* | (2006.01) |

(52) U.S. Cl.
CPC ............... *C12P 21/00* (2013.01); *C12P 21/02* (2013.01); *C12P 23/00* (2013.01); *C12P 37/00* (2013.01)

(56) References Cited

U.S. PATENT DOCUMENTS

| | | |
|---|---|---|
| 6,204,061 B1 | 3/2001 | Capecchi |
| 6,548,285 B1 | 4/2003 | Swinkels |
| 6,569,681 B1 | 5/2003 | Ivanov |
| 6,576,443 B2 | 6/2003 | Hennecke |
| 6,753,151 B1 | 6/2004 | Jackson et al. |
| 7,736,886 B2 | 6/2010 | Puchta |
| 8,034,790 B2 | 10/2011 | Chada |
| 2002/0168709 A1 | 11/2002 | Hennecke |
| 2003/0092183 A1 | 5/2003 | Fisher |
| 2004/0073967 A1 | 4/2004 | Hooykaas et al. |
| 2005/0172365 A1 | 8/2005 | Puchta |
| 2005/0181509 A1 | 8/2005 | Kang |
| 2005/0233959 A1 | 10/2005 | Chada |
| 2007/0155014 A1 | 7/2007 | Bertolini |
| 2008/0134351 A1 | 6/2008 | Sanchez-Fernandez |
| 2008/0138905 A1 | 6/2008 | Inoue |
| 2008/0206872 A1 | 8/2008 | Hooykaas |
| 2008/0227145 A1 | 9/2008 | Dekker |
| 2009/0124014 A1 | 5/2009 | van den Berg |
| 2009/0170206 A1 | 7/2009 | van den Berg |
| 2010/0120154 A1 | 5/2010 | Touw-Riel |
| 2010/0291653 A1 | 11/2010 | Ness |
| 2012/0282698 A1 | 11/2012 | van den Berg |

FOREIGN PATENT DOCUMENTS

| | | |
|---|---|---|
| WO | 99/53017 A2 | 10/1999 |
| WO | WO 00/60359 | 10/2000 |
| WO | WO 00/60359 A3 | 10/2000 |
| WO | 01/68882 | 9/2001 |
| WO | WO 01/68882 A2 | 9/2001 |
| WO | 02/052026 A2 | 7/2002 |
| WO | WO 02/052026 A2 | 7/2002 |
| WO | 03/089617 | 10/2003 |
| WO | 2005040186 A2 | 5/2005 |
| WO | 2005/095624 | 10/2005 |
| WO | 2007013979 A2 | 2/2007 |

OTHER PUBLICATIONS

Momany et al., "Characterization of the *Aspergillus nidulans* Septin (asp) Gene Family", Genetics Society of America, 2001, pp. 969-977, Department of Botany, University of Georgia, Athens, GA.
Primrose et al., "Principles of Genome Analysis and Genomics", Blackwell Science, 2003, pp. 3-134, Malden, MA.
Krappmann et al., "Gene Targeting in Aspergillus fumigatus by Homologous Recombination Is Facilitated in a Nonhomologous End-Joining-Deficient Genetic Background," Institute of Microbiology & Genetics, Department of Molecular Microbiology and Genetics, Georg-August-University, Gotttingen, Germany, Eukaryotic XELL, Jan. 2006, pp. 212-215, vol. 5, No. 1.
Mizuntani et al., "A defect of LigD (human Lig4 homolog) for nonhomologous end joining significantly improved efficiency of gene-trageting in Aspergillus oryzae," ScienceDirect, Fungal Genetics and Biology 45 (2008) 878-889.
Supplemental examples on Krappmann et al. (2006) and Mizutani et al. (2008), submitted with Written Submission Opponent in Oral Proceedings /Written Submissions in preparation of the Oral Proceedings scheduled on Jun. 6, 2013 in the Oppositions against EP Application No. 05740129.1/1733040B1, dated Apr. 5, 2013.
Minutes Oral Proceedings Opposition against EP Application No. 05740129.1/1733040B1, dated Jul. 3, 2013.
Written Submission Opponent in Oral Proceedings against EP Application No. 057401291/1733040B1, dated Feb. 27, 2013.
DSM, Written Submission Opponent in Oral Proceedings /Written Submissions in preparation of the Oral Proceedings scheduled on Jun. 6, 2013 in the Oppositions against EP Application No. 05740129.1/1733040B1, dated Apr. 5, 2013.
Boer et al., "Higly efficient gene trageting in penicillum chrysogenum using the bi-partite approach in Δlig4 or Δku70 mutants," ScienceDirect, Fungal Genetics and Biology 47 (2010) 839-846.
Kolar, Margareta et al, Gene, 1988, vol. 61(1), pp. 127-134, Transformation of Penicillium chrysogenum using dominant selection markers and expression of an *Escherichia coli* lacZ fusion gene.
Intl Search Report of PCT/EP2007/052393 Mailed Aug. 6, 2007.
Communication of a Notice of Opposition Against EP1733040 B1; Application No. 05740129.1-2402 / 1733040 Dated Jun. 6, 2011.
Summons to Attend Oral Proceeding in Opposition Against EP1733040 Bl; Application No. 05740129.1-2402 / 1733040 Dated Nov. 7, 2012.
Proprietor Reply in Opposition EP1733040 B1; Application No. 05740129.1-2402 / 1733040 Dated Jan. 25, 2012.
Teo et al; "LIF1P Targets the DNA Ligase LIG4P to Sites of DNA Double-Strand Breaks"; Curr. Biol. 10: 165-168 (2000).
Valencia et al; "NEJ1 Controls Non-Homologous End Joining in *Saccharomyces cerevisiae*"; Nature 414: 666-669 (2001).
Kegel et al.; "NEJ1P, A Cell Type-Specific Regulator of Nonhomologous End Joining in Yeast"; Curr. Biol. 11: 1611-1617 (2001).
Cheveroche et al; "A Rapid Method for Efficient Gene Replacement in the Replacement in the Filamentous Fungus Aspergillus Nidulans"; Nucleic Acid Research 28: E97 (2000).
Meyer; "Genetic Engineering of Filamentous Fungi—Progress, Obstacles and Future Trends"; Biotechnology Advances 26: 177-185 (2008).
Ray et al., "Homologous Recombination: Ends As the Means", Trends in Plant Science, 7(10): 435-440, Oct. 2002.
Lewis et al., "Tying Up Loose Ends: Nonhomologous End-Joining in *Saccharomyces cerevisiae*", Mutation Research, 451, Feb. 2000, 71-89.
Pierce et al., "KU DNA End-Binding Protein Modulates Homologous Repair of Double-Strand Breaks in Mammalian Cells", Genes and Devekionent, 15: 3237-3242 (2001).
Schiestl et al., "Integratiion of DNA Fragments by Illegitimate Recombination in *Saccharomyces cerevisiae*", Proc. Natl. Acad. Sci., vol. 88, pp. 7585-7589, Sep. 1991.
Reiss et al., RECA Stimulates Sister Chromatid Exchange and the Fidelity of Double-Strand Repair, but Not Gene Targeting, in Plants Transformed by Agrobacterium, Proc. Natl. Acad. Sci., vol. 97, No. 7, pp. 3358-3363, Mar. 2000.
Carvalho et al, "Expanding the ku70 toolbox for filamentous fungi: establishment of complementation vectors and recipient strains for advanced gene analyses", Applied Genetics and Molecular Biotechnology, published Apr. 27, 2010 (11 pages).
Choi et al, "Enhanced Homologous Recombination in *Fusarium verticillioides* by Disruption of FvKU70, a Gene Required for a Non-homologous End Joining Mechanism", Plant Pathol, J. 24(1): 1-7 (2008).
Nayak et al, "A Versatile and Efficient Gene-Targeting System for *Aspergillus nidulans*", Genetics 172:1557-1566 (Mar. 2006).

(56) References Cited

OTHER PUBLICATIONS

Borkovich et al. "Lessons from the genome sequence of *Neurospora crassa*: Tracing the path from genomic blueprint to multicellular organism" Microbiol. Mol. Biol. Rev. 68:1-108 (2004).
Boulton et al. "Identification of *Saccharomyces cerevisiae* Ku80 homologue: Roles in DNA double strand break rejoining and in telomeric maintenance" Nucl. Acids Res. 24:4639-4648 (1996).
Galagan et al. "*Neurospora crassa* strain OR74A chromosome IV cont3.499" Accession Nos. AABX1000206 and AABX01000000 (53 pages) from Nature 422:859-868 (2003).
Galagan et al. "*Neurospora crassa* strain OR74A cont3.5, whole genome shotgun sequence" Accession Nos. AABX01000750 and AABX01000000 (28 pages) from Nature 422:859-868 (2003).
Nayak et al. "Deletion of the Ku70 homolog of *Aspergillus nidulans* facilitates gene replacement and gene tagging" Abstract No. 39 from the Second *Aspergillus* Meeting at Asilomar Conference Center (2005).
Ninomiya et al. "Analysis of non-homologous recombination genes, ncku70 and ncku80, in *Neurospora crassa*" Genes & Genet. Syst. 78:463 and 75$^{th}$ Annual Meeting of the Genetics Society of Japan (2003).
Ninomiya et al. "Highly efficient gene replacements in Neurospora strains deficient for nonhomologous end-joining" Proc. Natl. Acad. Sci. USA 101:12248-12253 (2004).
Tsukamoto et al. "Hdf1, a yeast Ku-protein homologue, is involved in illegitimate recombination, but not in homologous recombination" Nucl. Acids Res. 24:2067-2072 (1996).
Int'l Search Report of PCT/EP2005/051464 (2005).
Takao, Masashi et al., "Characterization of a UV endonuclease gene from the fisson yeast *Schizosaccharomyces pombe* and its bacterial homolog", Nucleic Acids Research, Oxford University Press 1996, pp. 1267-1271, vol. 24, No. 7.

FILAMENTOUS FUNGAL MUTANTS WITH IMPROVED HOMOLOGOUS RECOMBINATION EFFICIENCY

CROSS REFERENCE TO RELATED APPLICATIONS

This application is a divisional application of U.S. application Ser. No. 10/594,014, filed Sep. 25, 2006, which is a §371 National Stage Application of PCT/EP2005/051464, filed Mar. 31, 2005, which claims priority to European Application No. 04076057.1, filed Apr. 2, 2004, the contents all of which are incorporated herein by reference in their entireties.

REFERENCE TO SEQUENCE LISTING SUBMITTED AS A COMPLIANT ASCII TEXT FILE (.txt)

A Sequence Listing is submitted herewith as an ASCII compliant text file named "2919208-039001_Sequence_Listing_ST25.txt", created on Dec. 4, 2015, and having a size of 128,113 bytes as permitted under 37 C.F.R. §1.821(c). The material in the aforementioned text file is hereby incorporated by reference in its entirety.

BACKGROUND

Field of the Invention

The invention relates to the field of molecular biology. It particularly relates to methods to improve the efficiency of directed Integration of nucleic acids into the genome of a filamentous fungus and uses thereof.

Description of Related Art

Eukaryotic cells are preferred organisms fur (recombinant) production of polypeptides and secondary metabolites. When constructing, for example, a protein production strain, the site of integration of the gene of interest coding for the protein to be produced is crucial for the regulation of transcription and/or expression of the integrated gene of interest. Since in most eukaryotic organisms integration of DNA into the genome occurs with high frequency at random, the construction of a protein production strain by recombinant DNA technology often leads to the unwanted random integration of the expression cassette comprising the gene encoding the protein to be produced. This uncontrolled "at random multiple integration" of an expression cassette is a potentially dangerous process, which can lead to unwanted modification of the genome of the host. It is therefore highly desirable to be able to construct a protein production strain by ensuring the correct targeting of the expression cassette with high efficiency. Furthermore, now that the sequence of complete genomes of an increasing amount of organisms is becoming available, this opens the opportunity to construct genome spanning overexpression and deletion libraries. An important requirement for the efficient construction of such libraries is that the organism. In question can be efficiently transformed and that the required homology needed to direct targeted integration of a nucleic acid into the genomes relatively short.

Eukaryotic cells have at least two separate pathways (one via homologous and one via non-homologous recombination) through which nucleic acids (in particular of course DNA) can be integrated into the host genome. The yeast Saccharomyces cerevlsiaa is an organism with a preference for homologous recombination (HR). The ratio of non-homologous to homologous recombination (NHR/HR) of this organism may vary from about 0.07 to 0.007.

WO 02/052026 discloses mutants of Saccharomyces cerevisiae having an improved targeting efficiency of DNA sequences into its genome. Such mutant strains are deficient in a gene involved in NHR (KU70).

Contrary to Saccharomyces cerevisiae, most higher eukaryotes such as filamentous fungal cells up to mammalian cell have a preference for NHR. Among filamentous fungi, the NHR/HR ratio is ranged between 1 and more than 100. In such organisms, targeted integration frequency is rather low. To improve this frequency, the length of homologous regions flanking a polynucleotide sequence to be integrated into the genome of such organisms has to be relatively long for example at least 2000 bp for disrupting a single gene and at least 500 bp for screening putative transformants. The necessity of such flanking regions represents a heavy burden when cloning the DNA construct comprising said polynucleotide and when transforming the organism with it. Moreover, neighbouring genes which Ile within those flanking regions can easily be disturbed during the recombination processes following transformation, thereby causing unwanted and unexpected side-effects.

Mammalian cells deficient in KU70 have already been isolated (Pierce et al, Genes and Development, (2001), 15: 3237-3242). These mutants have a six-fold higher homology-directed repair frequency, but no increase in the efficiency of homology-directed targeted integration. This suggests that results obtained in organisms with a preference for HR (Saccharomyces cerevisiae) cannot be extrapolated to organisms with a preference for NHR.

Surprisingly, we found that steering the integration pathways of nucleic acids towards HR in filamentous fungi resulted in an improved efficiency for targeted integration of nucleic acids into the genome of filamentous fungi.

DESCRIPTION OF THE INVENTION

Figure 1:
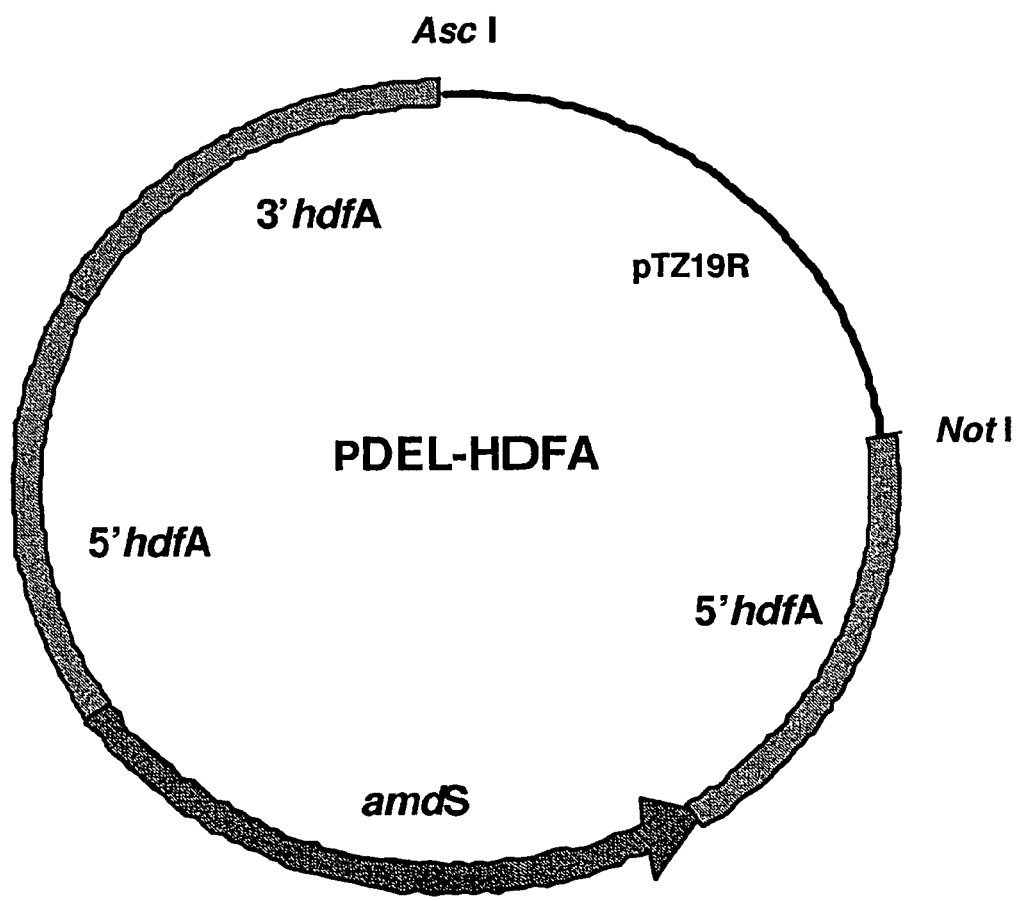
FIG. 1 depicts the replacement vector pDEL-HDFA used to inactive the hdfA gene in Aspergillus niger (A. niger). The replacement vector comprises the hdfA flanking regions, the amdS marker and E. coli DNA. The E. coli DNA was removed by digestion with restriction enzymes Ascl and Notl, prior to transformation of the A. niger strains.

All patents and publications, Including all sequences and methods disclosed within such patents and publications, referred to herein are expressly incorporated by reference. These patents and publications include: EP 357 127 B, EP 635 574 B, WO 97/06261, WO 98/46772.

Method for Increasing the Efficiency of Targeted Integration of a Polynucleotide into the Genome of a Filamentous Fungal Cell The present invention provides a method for increasing the efficiency of targeted integration of a polynucleotide to a pre-determined site into the genome of a filamentous fungal cell, with a preference for NHR, wherein said polynucleotide has a region of homology with said pre-determined site comprising steering an integration pathway towards HR. The present invention arrives at such steering either by elevating the efficiency of the HR pathway, and/or by lowering (meaning reducing) the efficiency of the NHR pathway and/or by decreasing the NHR/HR ratio.

In the context of the invention, the HR pathway is defined as all genes and elements being involved in the control of the targeted integration of polynucleotides into the genome of a host, said polynucleotides having a certain homology with a certain pre-determined site of the genome of a host wherein the integration is targeted. The NHR pathway is defined as all genes and elements being involved in the control of the integration of polynucleotides into the genome of a host, irrespective of the degree of homology of the said polynucleotides with the genome sequence of the host.

According to a preferred embodiment, the steering comprises providing a mutant of a parent filamentous fungal cell, wherein the NHR/HR ratio is decreased in the mutant of at least 5% as compared to said ratio in said parent organism as measured by the following assay. More preferably, the NHR/HR ratio is decreased in the mutant of at least 10%, even more preferably at least 50% and most preferably at least 100% as compared to said ratio in said parent organism.

According to another preferred embodiment, the filamentous fungal cell of the invention has a ratio NHR/HR, which is at least 200, at least 50, at least 10 as measured by the following assay. Preferably the ratio of the filamentous fungal cell is at least 1, more preferably at least 0.5, even more preferably at least 0.1, even more preferably at least 0.05, even more preferably at least 0.01 even more preferably at least 0.005 even more preferably at least 0.001 even more preferably at least 0.0005 even more preferably at least 0.0001 and most preferably at least 0.00001.

According to a more preferred embodiment, the filamentous fungal cell of the invention has a ratio NHR/HR, which is less than 200, even more preferably less than 50, less than 10 as measured by the following assay. Even more preferably the ratio of the filamentous fungal cell is less than 1, even more preferably less than 0.5, even more preferably less than 0.1, even more preferably less than 0.05, even more preferably less than 0.01 even more preferably less than 0.005 even more preferably less than 0.001 even more preferably less than 0.0005 even more preferably less than 0.0001 and most preferably less than 0.00001.

The ratio of NHR/HR is preferably measured by the assay as described in WO 02/052026 (table 2, p23). According to a preferred embodiment, the parent organism is one of the filamentous fungus cells as defined under the section host cell. According to another preferred embodiment, the filamentous fungus cell of the invention originates from a species as defined under the section host cell.

Alternatively and according to a less preferred embodiment, the NHR/HR ratio in a filamentous fungus is monitored using techniques known to the skilled person such as transcriptional profiling and/or northern blotting and/or western blotting of at least one of the following components involved in such pathways: KU70, KU80, MRE11, RAD50, RAD51, RAD52, XRS2, SIR4, LIG4.

In the context of this invention, "a region of homology" means "at least one" region of homology. A pre-determined site is herein defined as a site within the genetic material contained by a host cell to which a polynucleotide with homology to this same site is integrated with a method according to the invention.

In a preferred embodiment, the invention provides a method for increasing the efficiency of targeted integration of a polynucleotide to a pre-determined site into the genome of a filamentous fungal cell with a preference for NHR, wherein said polynucleotide has a region of homology with said predetermined site comprising steering an integration pathway towards HR by providing a filamentous fungus, wherein the efficiency of the NHR pathway has been lowered and/or the NHR/HR ratio has been decreased compared to the efficiency of the NHR pathway and/or the NHR/HR ratio of the filamentous fungus it originates from under the same conditions. According to a preferred embodiment, the parent organism is one of the filamentous fungus as defined under the section host cell.

The efficiency of the NHR pathway is preferably measured in the assay as described in WO02/052026 (table 2, p23).

Alternatively and according to a less preferred embodiment, the efficiency of the NHR pathway in a filamentous fungus is monitored using techniques known to the skilled person such as transcriptional profiling and/or northern blotting and/or western blotting of components involved in such pathway. More preferably, the expression level of at least one of the following components is monitored: KU70, KU80, MRE11, RAD50, RAD51, RAD52, XRS2, SIR4, LIG4. Even more preferably, the expression level of homologous components of the KU complex is monitored. Most preferably, the expression level of homologous KU70 and/or KU80 is monitored.

A lowered NHR efficiency means at least lower than in the parents cell the obtained cell originates from. Preferably, lowered means twice lower, more preferably ten times lower, even more preferably 100 times lower, most preferably more than 1000 times lower and even most preferably not detectable using northern or western blotting, array techniques or a phenotypic screen.

A typical phenotypic screen that could be used comprises the following steps: transforming the putative NHR mutants with an expression cassette comprising a selection marker gene flanked by homologous sequences of a predetermined genomic site. The selection marker gene used in this phenotypic screen can be selected from a number of marker genes that are useful for transformation of filamentous fungi. By way of example these markers include but are not limited to dominant and bi-directional selection marker gene such as an acetamidase (amdS) gene (EP 635 574 B or WO 97/06261), auxotrophic marker genes such as argB, trpC or pyrG and antibiotic resistance genes providing resistance against e.g. phleomycin (the product encoded by the ble gene confers resistance to phleomyclne), hygromycin B or G418. A preferred selection marker gene is the ble gene encoding a protein conferring resistance to phleomycin. The putative NHR mutants already contain at this predetermined genomic site a birectional selection marker gene such as an amdS gene, nitrate reductase gene (niaD), sulphate permease (Sut B) gene or PyrG gene. The niaD gene has already been described elsewhere (Gouka R J, van Hartingsveldt W, Bovenberg R A, van den Hondel C A, van Gorcom R F. Cloning of the nitrate-nitrite reductase gene duster of *Penicillium chrysogenum* and use of the niaD gene as a homologous selection marker. J Biotechnol. 1991 September; 20(2): 189-99). The niaD gene enables direct selection of transformants on plates containing chlorate, as cells become resistant to chlorate. The sutB gene has already been described elsewhere, (van de Kamp M, Pizzinini E, Vos A, van der Lende T R, Schuurs T A, Newbert R W, Turner G, Konings W N, Driessen A J. Sulfate transport in *Penicillium chrysogenum*: cloning and characterization of the sutA and sutB genes. J. Bacteriol. 1999 December; 181(23):7228-34). A preferred selection marker gene is the *A. nidulans* amdS coding sequence fused to the *A. nidulans* gpdA promoter (EP635 574 B). AmdS genes from other filamentous fungi may also be used (WO 97/06261). In the preferred form of the phenotypic screen, the amdS gene is present at the predetermined genomic site and the ble gene is used as the gene to be targeted to the predetermined site. In non-HR-improved mutants the ble-cassette will integrate randomly in the genome, enabling many transformants to grow on a double selective medium with both acetamide and phleomycin; and relatively few transformants to grow on fluoracetamide-phleomycin plates. In mutants with improved HR there will be a limited number of transformants on the acetamide-phleomcyin double selective plates as the amdS-cassette is efficiently exchanged with the ble-cassette. In this case more mutants will appear on fluoracetamide-phleomycin double selective plates.

According to another preferred embodiment, the filamentous fungus having a lowered NHR efficiency and/or a decreased NHR/HR ratio is a filamentous fungus wherein a component involved in NHR has been inhibited. In this context, "a" means "at least one": at least one component involved in NHR has been inhibited in a given filamentous fungus. Inhibition can be achieved by down regulating the expression level of a gene involved in NHR or inactivating a gene encoding a component involved in NHR and/or by down regulating the expression level of a component involved in NHR, and/or (temporarily) decreasing the (protein) activity of a component involved in NHR and a combination of these possibilities.

Preferably, the filamentous fungus obtained has the expression of a gene involved in NHR down regulated by comparison to the expression of said gene in the parent filamentous fungal cell it originates from under the same conditions. According to a preferred embodiment, the parent filamentous fungus is one of the filamentous fungus as defined under the section host cell.

The expression level of a gene, or a DNA sequence is down regulated when the expression level of this specific gene or DNA sequence in the obtained filamentous fungus is lower than the expression level of the same gene or DNA sequence in the parental filamentous fungus it originates from, preferably three times lower, more preferably four times lower, most preferably more than four times lower and even most preferably not detectable using northern, or western blotting or 'omics' techniques like transcriptomics and proteomics.

The down and/or up regulation of the expression level of a DNA sequence can be monitored by quantifying the amount of corresponding mRNA present in a cell by northern blotting (in Molecular Cloning: A Laboratory Manual, Sambrook of at, New York: Cold Spring Harbour Press, 1989) for example and/or by quantifying the amount of corresponding protein present in a cell by western blotting for example. The difference in mRNA amount may also be quantified by DNA array analysis (Eisen, M. B. and Brown, P. O. DNA arrays for analysis of gene expression. Methods Enzymol. 1999:303:179-205).

The down regulation of the expression level of at least one gene or DNA sequence may be obtained by genetic manipulation by one of the following techniques or by a combination thereof:

a. using recombinant genetic manipulation techniques,
 b. submitting the filamentous fungus to mutagenesis.

Alternatively or in combination with above-mentioned techniques and according to another preferred embodiment, the down regulation of the expression level of at least one gene or DNA sequence may be obtained by submitting the filamentous fungus to a inhibiting compound/composition.

The filamentous fungus obtained may be subsequently selected by monitoring the expression level of said gene or DNA sequence. Optionally, the filamentous fungus is subsequently selected by measuring its efficiency of the NHR and/or of the HR pathways and/or its NHR/HR ratio. In the context of the invention, the efficiency of the HR pathway of a filamentous fungus may be measured by the efficiency of the targeted integration of a given polynucleotide sequence into a predetermined site in the genome of the filamentous fungus using given homology region(s). In the context of the invention, the efficiency of the NHR pathway of a filamentous fungus may be measured by the efficiency of the non targeted integration of a given polynucleotide sequence in the genome of the filamentous fungus irrespective of any homology region(s).

More preferably, the down regulation of the expression of at least one DNA sequence is made with recombinant genetic manipulation techniques such as defined in step a. to obtain a recombinant filamentous fungus. Most preferably step a. comprises deleting the DNA sequence, even most preferably the deleted DNA sequence is replaced by a non-functional variant thereof, and even most preferably the deletion and replacement are made by gene replacement preferably as described in EP 357127 B.

In cases of deletion or replacement of at least one DNA sequence of the chosen filamentous fungus, an appropriate DNA sequence has to be introduced at the target locus. The target locus is in this case the DNA sequence involved in NHR pathway to be deleted or replaced. The appropriate DNA sequence is preferably present on a cloning vector. Suitable cloning vector are the ones that are able to integrate at the pre-determined target locus in the chromosomes of the filamentous fungal host cell used. Preferred integrative cloning vector comprises a DNA fragment, which is homologous to the DNA sequence to be deleted or replaced for targeting the integration of the cloning vector to this pre-determined locus. In order to promote targeted integration, the cloning vector is preferably linearized prior to transformation of the host cell. Preferably, linearization is performed such that at least one but preferably either end of the cloning vector is flanked by sequences homologous to the DNA sequence to be deleted or replaced.

The length of the homologous sequences flanking the DNA sequence to be deleted or replaced is preferably less than 2 kb, even preferably less than 1 kb, even more preferably less than 0.5 kb, even more preferably less than 0.2 kb, even more preferably less than 0.1 kb, even more preferably less than 50 bp and most preferably less than 30 bp.

The selection marker gene in the cloning vector can be selected from a number of marker genes that are useful for transformation of filamentous fungi. By way of example these markers include but are not limited to dominant and bidirectional selection marker gene such as an acetamidase (amdS) gene (EP 635 574 B or WO 97/06261), auxotrophic marker genes such as argB, trpC, or pyrG and antibiotic resistance genes providing resistance against e.g. phleomycin, hygromycin B or G418. A preferred selection marker gene is the A. nidulans amdS coding sequence fused to the A. nidulans gpdA promoter (EP635 574 B). AmdS genes from other filamentous fungus may also be used (WO 97/06261). The amdS selection marker gene has the advantage it can be used several times in the same strain to replace and/or delete distinct DNA sequences.

By means of counterselection on fluoracetamide media as described in EP 635 574 B, the resulting strain is marker free and can be used for further gene modifications.

A preferred strategy for down regulating the expression of a given DNA sequence comprises the deletion of the wild type DNA sequence and/or replacement by a modified DNA sequence, whose expression product is not functional. The deletion and the replacement are preferably performed by the gene replacement technique described in EP 0 357 127 B1. The specific deletion of a gene is preferably performed wing the amdS gene as selection marker gene as described in EP 635 574 B.

Alternatively or in combination with other mentioned techniques, a technique based on in vivo recombination of cosmids in E. coli can be used, as described in: A rapid method for efficient gene replacement in the filamentous fungus Aspergillus nidulans (2000) Chaveroche, M K., Chico, J-M. and d'Enfert C; Nucleic acids Research, vol 28, no 22. This technique is applicable to other filamentous fungi like for example A. niger.

Down regulating the expression of a DNA sequence may also be achieved by using anti sense nucleic acids, or by UV or chemical mutagenesis (Mattem, I. E., van Noort van den Berg, P., Archer, D. B., Roberts, I. N. and van den Hondel, C. A., Isolation and characterization of mutants of Aspergillus niger deficient in extracellular proteases. Mol Gen Genet. 1992 August; 234(2):332-6.).

Preferably, the deficiency brought in the NHR pathway is an inducible one. This can be reached by replacing the endogenous regulatory regions of the gene encoding the component involved in NHR by new regulatory regions, preferably by using a repressible or regulatable promoter, more preferably by using a promoter that can be switch on/off: by glucose repression, or ammonia repression, or pH repression. Examples of glucose-repressed promoters are the Penicillium chrysogenum pcbAB promoter (Martin J F, Casqueiro J, Kosalkova K, Marcos A T, Gutierrez S. Penicillin and cephalosporin biosynthesis: mechanism of carbon catabolite regulation of penicillin production. Antonie Van Leeuwenhoek. 1999 Jan.-Feb.; 75(1-2):21-31. Review.) or the Aspergillus niger glucoamylase promoter. Examples of on/off switchable promoters are described in the following publications:

An activator/repressor dual system allows tight tetracycline-regulated gene expression in budding yeast: Belli et al, (1998) Nucl. Add Research. vol 26, n.4:942.947,
A light-switchable gene promoter system: Shimizu-Sato et al, (2002) Nat. Biotech. Vol 20, no 10:1041-1044.

According to a preferred embodiment, the filamentous fungus is deficient in at least one of its endogenous genes, which are homologous with the following yeast genes involved in the NHR pathway KU70, KU80, RAD50, MRE11, XRS2 and SIR4 (van den Bosch et at (2002): DNA double-strand break repair by homologous recombination. Biol. Chem. Vol. 383:873-892 and Allen et al, (2003): Interactive competition between homologous recombination and non-homologous end joining. Mol. Cancer Res., vol 1:913-920). All kinds of mutants having at least one component involved in NHR, which is no longer capable or at least significantly less capable to perform its function in the process of NHR, are mutants contemplated by the present invention. Preferably, the component involved in NHR has been inhibited so that the efficiency of the NHR pathway in the obtained mutant is less than 90% of the activity in the parent cell it originates from under the same conditions as measured in the assay defined earlier, even preferably less than 85%, more preferably less than 80%, even more preferably less than 70%, most preferably less than 50%.

According to a preferred embodiment, the parent filamentous fungus is one of filamentous fungus as defined under the section host cell.

Preferably, the filamentous fungus cell is deficient in at least one of the following genes:
hdfA as identified in SEQ ID NO: 2 or 19 or homologues thereof, or
hdfB as identified in SEQ ID NO: 5 or 22 or homologues thereof, or or both.

According to another preferred embodiment, the filamentous fungus has the amount of at least one of the proteins encoded by these genes hdfA and hdfB that is decreased upon Induction.

According to another preferred embodiment, the down regulation of the expression level of at least one gene or DNA sequence may be obtained by genetic modification by submitting the filamentous fungus to mutagenesis. Filamentous fungal cells may be subjected to random mutagenesis and subsequently to a selection assay to isolate the mutants with improved HR from the whole diverse population of mutants.

According to a preferred embodiment of the present invention, one of the filamentous fungal cell defined under the section host cell is used as starting strain to perform the mutagenesis.

For example, the starting strain is subjected to UV irradiation so that the survival percentage is ranged between 0.001% and 60%. Preferably, the survival percentage is ranged between 0.01% and 50%. It is well known to the skilled person that conidiospores is the preferred material to mutagenize filamentous fungi by physical or chemical means. Mutants may however also be obtained from mycelium cells. Also, other mutagenic treatments than UV can be applied as chemical agents (e.g. NTG). The selection method described herein may be applied to select mutants obtained from either conidiospores or mycelium cells.

Preferably the mutagenesls is applied to conldlospores. UV irradiation is preferably applied for different times such as 7.5, 15 and 30 minutes to obtain mild, medium and strong mutation rate levels in the cells. The mutated samples may either be directly re-sporulated or incubated for an extended recovery period in a rich medium such as YNB or YEPD (see definition in example. 9) before sporulation was induced (for example as described in example 9).

The sporulated batches may be then tested for their efficiency in gene targeting. This could be tested by the following method. Protoplasts may be transformed with at least one, preferably two or more DNA fragments carrying expression cassettes of functional selection markers. The selection marker genes in the expression cassettes can be selected from a number of marker genes that are useful for transformation of filamentous fungi. By way of example these markers include but are not limited to dominant and bi-directional selection marker gene such as an acetamidase (amdS) gene (EP 635 574 or WO 97/06261), auxotrophic marker genes such as argB, trpC, or prG and antibiotic resistance genes providing resistance against e.g. phleomycin, hygromycin Bor G418. Preferably the selection markers used are the ble and amdS genes. The amdS cassette used is the *A. nidulans* coding sequence fused to the *A. nidulans* gpdA promoter (EP635 574 B). amdS genes from other filamentous fungus may also be used (WO 97106261). The gene ble encodes a protein capable of conferring resistance to phleomycin. The gene amdS encodes a protein enabling cells to grow on acetamide as the sole nitrogen source (as described in EP635 574B). Techniques applied for the transfer of DNA to protoplasts of filamentous fungi are well known in the art and are described in many references, including Finkelstein and Ball (eds.), Biotechnology of filamentous fungi technology and products, Butterworth-Heinemann (1992); Bennett and Lasure (eds.) More Gene Manipulations in fungi, Academic Press (1991); Turner, in: Killer (ed), Biotechnology, second completely revised edition, VHC (1992). The Ca-PEG mediated protoplast transformation is used as described in EP635574B.

To select targeted integration of these two expression cassettes to two distinct specific loci in the filamentous fungi genome short homologous stretches of DNA may be added for example via PCR on both sides of the DNA fragments. Several types of construct could be made to improve the chances to select a mutant having an improved targeting efficiency: the homologous stretches of DNA could typically vary from 30 bp to 1000 bp, preferably 30 bp to 700 bp, more preferably 30 bp to 500 bp, even more preferably 30 bp to 300 bp, more preferably 30 bp to 200 bp, even more preferably 30 bp to 100 bp and most preferably 30 bp. In theory all loci in the filamentous fungi genome could be chosen for targeting integration of the expression cassettes. Preferably, the locus wherein targeting will take place is such that when the wild type gene present at this locus has been replaced by the gene comprised in the expression cassette, the obtained mutant will display a change detectable by a given assay. Preferably the locus is the niaD locus, thereby disrupting the nitrate reductase gene (Gouka R J, van Hartingsveldt W, Bovenberg R A, van den Hondel C A, van Gorcom R F. Cloning of the nitrate-nitrite reductase gene cluster of *Penicillium chrysogenum* and use of the nIaD gene as a homologous selection marker. J Biotechnol. 1991 September; 20(2):189-99), enabling direct selection of transformants on plates containing chlorate, as cells become resistant to chlorate. Another preferred locus is the sutB locus, thereby disrupting the sulphate permease gene (van de Kamp M, Pizzinhi E, Vos A, van der Lende T R, Schuurs T A, Newbert R W, Turner G, Konings W N, Driessen A J. Sulfate transport in *Penicillium chrysogenum*: cloning and characterization of the sutA and sutB genes. J. Bacteriol. 1999 December; 181(23):7228-34), enabling direct selection of transformants on plates containing selenate. Mutants with both selection markers present and having the two alterations resulting from the inactivation of the genes present at the integration loci are strains with improved targeted integration.

According to another preferred embodiment, the mutant filamentous fungus having a lowered efficiency in the NHR pathway, or a decreased NHR/HR ratio and/or an elevated efficiency of the HR pathway is obtained by decreasing, more preferably partially or most preferably completely inhibiting a component involved in NHR.

Partial or complete inhibition of a component involved in NHR can be obtained by different methods, for example by an antibody directed against such a component or a chemical inhibitor or a protein inhibitor or a physical inhibitor (Tour O. et al, (2003) Nat. Biotech: Genetically targeted chromophore-assisted light inactivation. Vol. 21. no. 12:1505-1508) or peptide inhibitor or an anti-sense molecule or RNAi molecule (R. S. Kamath_et al, (2003) Nature: Systematic functional analysis of the *Caenorhabditis elegans* genome using RNAi.vol. 421, 231-237). Irrespective of the kind of (partial or more preferably complete) inhibition it is important that a component involved in NHR is no longer capable or at least significantly less capable to perform its function in the process of NHR as defined above.

Components involved in NHR comprise filamentous fungal homologues of yeast KU70, RAD50, MREII, XRS2, LIG4, SIR4, KU80, LIFL or NEIL or associating component. Because the nomenclature of genes differs between organisms a functional equivalent or a functional and/or a functional fragment thereof, all defined herein as being capable of performing (in function, not in amount) at least one function of the yeast genes KU70, RAD50, MREII, XRS2, LIG4, SIR4, KU80, LIFL or NEIL are also included in the present invention. By transiently (partially or more preferably completely) inhibiting a component involved in NHR a nucleic acid is integrated at any desired position without permanently modifying a component involved in NHR and preventing unwanted side effects caused by the permanent presence of such a modified component involved in NHR.

In addition of the above-mentioned techniques or as an alternative, it is also possible to obtain a lowered NHR efficiency by inhibiting the activity of proteins, which are involved in NHR or to re-localize the NHR involved proteins by means of alternative signal sequences (Ramon de Lucas, J., Martinez O, Perez P., Isabel Lopez, M., Valenciano, S. and Laborde, F. The *Aspergillus nidulans* camitine carrier encoded by the acuH gene is exclusively located in the mitochondria. FEMS Microbial Lett. 2001 Jul. 24; 201(2):193-8.) or retention signals (Dertox, P. M. and Madrid, S. M. The foldase CYPB is a component of the secretory pathway of *Aspergillus niger* and contains the endoplasmic reticulum retention signal HEEL. Mol. Genet Genomics. 2001 December; 266(4):537-45.).

Alternatively or in combination with above-mentioned techniques, inhibition of protein activity can also be obtained by UV or chemical mutagenesis (Mattem, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet 1992 August; 234(2):332-6.) or by the use of inhibitors like the proteasomal inhibitor of Affinity (clasto-lactacystin-β-lactone, Affinity Research Products Ltd., CW8405-Z02185.).

According to another preferred embodiment, the steering towards HR comprises adding an excess of small double stranded polynucleotides able to bind and thereby limit the expression of NHR components, next to the polynucleotide to be integrated (Agrawal N. et al: RNA interference: biology, mechanism and applications. Microbiol. Mol. Bid. Rev., vol. 67, no. 4:657-685).

In a preferred embodiment the invention provides a method for increasing the efficiency of targeted integration of a polynucleotide to a pre-determined site, whereby said polynucleotide has homology at or around the said pre-determined site, in a filamentous fungus with a preference for NHR comprising steering an integration pathway towards HR by providing a filamentous fungal cell, wherein the efficiency of the HR pathway has been elevated compared to the one of the parent filamentous fungus it originates from under the same conditions. The efficiency of the HR pathway is preferably assayed by the same assay as the one used for determining the NHR/HR ratio. According to a preferred embodiment, the parent organism is one of the filamentous fungi as defined in the section host cell.

Elevated means at least higher than in the parental cell the obtained cell originates from. Preferably, elevated means twice higher, more preferably three times higher, even more preferably four times higher, most preferably more than four times higher using northern, or western blotting or array technique or a phenotypic screen.

According to another preferred embodiment, the filamentous fungus has the expression level of at least one gene involved in HR, which has been up regulated by comparison to the expression level of the same gene in the filamentous fungal cell it originates from. This can be achieved by increasing the expression level of a gene encoding a component involved in HR and/or by increasing the expression level of a component involved in HR and/or by (temporarily) increasing the activity of the component involved in HR.

Preferably, the filamentous fungus obtained has the expression of a gene involved in HR, which has been up regulated by comparison to the expression of said gene in the filamentous fungal cell it originates from.

The expression level of a DNA sequence is up regulated when the expression level of this specific DNA sequence in the obtained filamentous fungus is higher than the expression level of the same DNA sequence in the parental filamentous fungus it originates from, preferably three times higher, more preferably four times higher, most preferably more than four times higher using northern, or western blotting or array technique. According to a preferred embodiment, the parent organism is one of the filamentous fungi as defined in the section host cell.

The up regulation of the expression level of at least one DNA sequence may be obtained by genetic manipulation by one of the following techniques or by a combination thereof:
c. using recombinant genetic manipulation techniques,
d. submitting the filamentous fungus to mutagenesis, Alternatively or in combination with above-mentioned techniques and according to another preferred embodiment, the up regulation of the expression level of at least one gene or DNA sequence may be obtained by submitting the filamentous fungus to an activating compound/composition.

The filamentous fungus may be subsequently selected by monitoring the expression level of said DNA sequence and optionally the efficiency of the HR pathway of the filamentous fungus. The HR efficiency of a filamentous fungus may be measured by the efficiency of the targeted integration of a given polynucleotide sequence into a pre-determined site in the genome of the filamentous fungus using given homology region(s).

Preferably, the up regulation of the expression of at least one DNA sequence is made with recombinant genetic manipulation techniques such as defined in step a. to obtain a recombinant filamentous fungus. Preferably step a. comprises transforming the filamentous fungus with a DNA construct comprising the DNA sequence, preferably said DNA sequence being operationally linked to a promoter of a highly expressed gene. The chosen promoter may be stronger than the endogenous promoter of the DNA sequence to be over expressed. The promoter for expression of the DNA sequence is preferably derived from a highly expressed fungal gene.

A number of preferred highly expressed fungal genes are given by way of example: the amylase, glucoamylase, alcohol dehydrogenase, xylanase, glyceraldehydephosphate dehydrogenase or cellobiohydrolase genes from *Aspergilli* or *Trichoderma*. Most preferred highly expressed genes for these purposes are an *Aspergillus niger* glucoamylase gene, an *Aspergillus oryzae* TAKA-amylase gene, an *Aspergillus nidulans* gpdA gene or a *Trichoderma reesei* cellobiohydrolase gene. A glucoamylase promoter is the most preferred promoter to be used. These highly expressed genes are suitable both as target loci for integration of cloning vectors and as source of highly expressed fungal genes.

According to another preferred embodiment, step a. comprises increasing the copy number of the DNA sequence into the filamentous fungal cell, preferably by integrating into its genome copies of the DNA sequence, more preferably by targeting the integration of the DNA sequence at a highly expressed locus, preferably at a glucoamylase locus.

The up regulation of the expression of the DNA sequence may be reached by increasing the copy number of the DNA sequence by introducing at least one copy of the DNA sequence into the filamentous fungus or by changing for a stronger promoter or changing for a gene encoding a protein with better kinetics and/or lifetime. The DNA sequence may be present on a plasmid or integrated into the genome. The skilled person can choose amongst two alternative possibilities:
  over express at least one endogenous DNA sequence of the filamentous fungus being involved in the HR pathway. In this case, the filamentous fungus comprises several copies of its endogenous DNA sequence.
  over express at least one heterologous DNA involved in HR. In this case, the filamentous fungus would hale its endogenous DNA sequence involved in HR and, in addition at least one copy of a heterologous DNA sequence involved in HR. This heterologous DNA sequence is an homologue of its corresponding endogenous DNA sequence.

The filamentous fungus can be transformed with one or more copy of the DNA sequence (derived from inter alia Tilbum et al, 1983, Gene, 26:205-221). The DNA sequence can be either stably integrated into the genome of the filamentous fungus or introduced into the cell as part of a DNA molecule capable of autonomous replication. The DNA sequence is preferably present on a cloning vector. Any cloning vector capable of transforming a filamentous fungal host cell is suitable for use in the present invention. Cloning vectors for use in the invention thus comprise integrative cloning vectors, which integrate at random or at a predetermined target locus in the chromosomes of the filamentous fungal host cell, as well as autonomously maintained cloning vectors such as vectors comprising the AMA1-sequence in a preferred embodiment of the invention, the integrative cloning vector comprises a DNA fragment, which is homologous to a DNA sequence in a predetermined target locus in the genome of the filamentous fungal host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb.

Preferably, the DNA sequence in the cloning vector, which is homologous to the target locus is derived from a highly expressed locus meaning that it is derived from a gene, which is capable of high expression level in the filamentous fungal host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 WI (as described in EP 357 127 B1).

To Increase even more the number of copies of the DNA sequence to be over expressed the technique of gene conversion as described in WO98/46772 may be used.

The skilled person will appreciate the possibility that the homologous DNA sequence for targeting and the promoter sequence can coincide in one DNA fragment. The list of highly expressed genes given above is also suited as target locus.

An example of an autonomously maintained cloning vector is a cloning vector comprising the AMA1-sequence. AMA1 is a 6.0-kb genomic DNA fragment isolated from *Aspergillus nidulans*, which is capable of Autonomous Maintenance in *Aspergillus* (see e.g. Aleksenko and Clutterbuck (1997), Fungal Genet Biol. 21: 373-397).

According to another preferred embodiment of the method of the invention, step a. comprises transforming the filamentous fungus with a DNA construct comprising a selection marker gene. The selection marker gene in the cloning vector can be selected from a number of marker genes that are useful for transformation of filamentous fungi. By way of example these markers include but are not limited to dominant and bi-directional selection marker genes such as an amdS gene (EP 635574, WO 97/06261), auxotrophic marker genes such as argB, trpC, or pyrG and antibiotic resistance genes providing resistance against e.g. phleomycin, hygromycin B or G418. The use of a dominant and bi-directional selection marker gene is preferred. Preferably an amdS gene is preferred, more preferably an amdS gene from *Aspergillus nidulans* or *Aspergillus niger*. A most preferred selection marker gene is the *A. nidulans* amdS coding sequence fused to the *A. nidulans* gpdA promoter (see EP635574). AmdS genes from other filamentous fungus may also be used (WO 97/06261). The amdS selection marker gene has the advantage it can be used several times in the same strain to introduce, over express and/or delete distinct DNA sequences. By means of counterselection on fluoracetamide media as described in EP 635574, the resulting strain is maker free and can be used for further gene modifications.

Alternatively or in addition with above-mentioned techniques, up regulation of the expression of a DNA sequence can be reached using UV or chemical mutagenesis (Mattem, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet. 1992 August; 234 (2):332-6.).

In addition and/or in combination with up regulation of expression of DNA sequences involved in HR, it is also possible to obtain an increased HR efficiency by increasing the activity of proteins involved in HR by UV or chemical mutagenesis (Mattem, I. E., van Noort J. M., van den Berg, P., Archer, D. B., Roberts, I. N. and van den Hondel, C. A., Isolation and characterization of mutants of *Aspergillus niger* deficient in extracellular proteases. Mol Gen Genet 1992 August; 234(2):332-6.).

The skilled person would understand that to achieve the up regulation of the expression of a DNA sequence, one may use each of the described technique either separately or in combination.

The skilled person would also understand that to obtain a filamentous fungus with an increased HR/NHR ratio, and/or with a lowered NHR Efficiency and/or an elevated HR efficiency, one may use at least one of each technique described for respectively down and up regulating the expression of a given gene in a filamentous fungus. Preferably, all the techniques performed on the filamentous fungus to obtain a recombinant filamentous fungus having both a lowered NHR efficiency and an elevated HR efficiency have been performed using a dominant and bi-directional selection marker, preferably an amdS gene more preferably an amdS gene from *Aspergillus nidulans* or *Aspergillus niger*. The obtained filamentous fungus may be subsequently selected by monitoring the expression level of said DNA sequence as described before by using for example northern and/or western blotting and/or array and/or phenotype screening. Optionally, the efficiency of the NHR and/or HR pathways of the cell is monitored. The efficiency of these pathways of a filamentous fungus may be monitored as defined earlier on.

Preferably, the modification brought in the HR pathway is an inducible one. This can be reached by replacing the endogenous regulatory regions of the gene encoding the component involved in HR by inducible regulatory regions, preferably by using an inducible promoter. Examples of inducible promoters are the glucoamylase promoter of *Aspergillus niger*, the TAKA amylase promoter of *Aspergillus oryzae*, the paf promoter (Marx, F., Haas, H., Reindl, M., Stoffler, G., Lottspeich, F. and Redl, B. Cloning, structural organization and regulation of expression of the *Penicillium chrysogenum* paf gene encoding an abundantly secreted protein with antifungal activity Gene 167 (1-2), 167-171 (1995) or the pcbC promoter of *Penicillum chrysogenum* (Martin J F, Casqueiro J, Kosalkova K, Marcos A T, Gutierrez S. Penicillin and cephalosporin biosynthesis: mechanism of carbon catabolite regulation of penicillin production. Antonie Van Leeuwenhoek. 1999 January-February; 75(1-2):21-31. Review.) or the switch on/off systems earlier cited for down regulation of the expression of genes involved in NHR.

According to a preferred embodiment, the genes involved in the HR pathway, which are modified are the following genes or homologues thereof: RAD51, RAD52.

All kinds of mutants having at least one component involved in HR, which is more capable or at least significantly more capable to perform its function in the process of HR are mutants contemplated by the present invention. Preferably, the activity of the components involved in HR has been modified so that the efficiency of the HR pathway is more than 110% of the efficiency in the parent cell it originates from under the same conditions as measured in the assay defined earlier, more preferably more than 200%, most preferably more than 500%. According to a preferred embodiment the parent organism is one of the filamentous fungi as defined under the section host cell. Methods according to the present invention, as extensively but not limiting discussed above, can be used in a wide variety of applications. Some specific applications are described below.

Host Cell

Accordingly, the present invention further relates to the filamentous fungus per se, which is preferably used in the method of the invention for increasing the efficiency of targeted integration of a polynucleotide to a pre-determined site into the genome of said filamentous fungal cell, said filamentous fungus having a preference for NHR, and wherein said polynucleotide has a region of homology with said pre-determined site and said method comprising steering an integration pathway towards HR. The characteristics of the filamentous fungus that can be used in this method have been earlier defined. The filamentous fungus preferably used in the method of the invention is a mutant originating from a parent cell, wherein the ratio of NHR/HR is decreased and/or wherein the efficiency of the NHR pathway has been lowered and/or the efficiency of the HR pathway has been elevated in said mutant cell as compared to said ratio and said efficiencies in said parent organism under the same conditions. The assay used to determine the ratio NHR/HR and/or the efficiency of the NHR pathway and/or the efficiency of the HR pathway has been earlier described.

The host cell of the present invention is a filamentous fungus, which is capable of being transformed with a cloning vector. For most filamentous fungi tested thus far it was found that they could be transformed using transformation protocols developed for *Aspergillus* (derived from inter alia Tilbum at al. 1983, Gene 26: 205-221). The skilled person will recognise that successful transformation of the filamentous fungal host species is not limited to the use of vectors, selection marker systems, promoters and transformation protocols specifically exemplified herein.

A filamentous fungus is herein defined as a eukaryotic microorganism of the subdivision Eumycotina in filamentous form, I.e. the vegetative growth of which occurs by hyphal elongation. Preferred filamentous fungal host cells are selected from the group consisting of the genera *Aspergillus, Trichoderma, Fusarium, Penicillium*, and *Acremonium*.

In a more preferred embodiment of the invention, the filamentous fungal host cell is selected from the group consisting of *A. nidulans, A. oryzae, A. sojae, Aspergilli* of the *A. niger* Group, *Trichoderma reesi* and *Penicillium* species. Preferably the *Penicillium* is a *Penicillium chrysogenum* or *Penicillium citrinum* species.

The *A. niger* group is herein defined according to Raper and Fennell (1965, In: The Genus *Aspergillus*, The Williams & Wilkins Company, Baltimore, pp 293-344) and comprises all (black) *Aspergilli* therein included by these authors. Most preferred filamentous fungal host cells are selected from the group consisting of *Aspergilli* of the *A. niger* group, *A. oryzae, Trichoderma reesei* and *Penicillium chrysogenum*.

According to a preferred embodiment, the parent organism is the deposited filamentous fungus cell *Aspergillus niger* CBS 513.88, *Aspergillus oryzae* ATCC 20423, IFO 4177, ATCC 1011, ATCC 9576, ATCC14488-14491, ATCC 11601, ATCC12892, *Penicillium chrysogenum* CBS 455.95 or *Penicillium citrinum* ATCC 38065, *Penicillium chrysogenum* P2, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006, *Claviceps paspali* CBS110.22, *Claviceps purpurea* CBS164.59, *Penicillium brevicompactum* ATCC 9056, *Aspergillus terreus* ATCC 20542, *Aspergillus nidulans* ATCC 28901 and or derivatives thereof.

According to another preferred embodiment, the filamentous fungal cell of the invention has a ratio NHR/HR, which is at least 200, at least 50, at least 10 as measured by the following assay. Preferably the ratio of the filamentous fungal cell is at least 1, more preferably at least 0.5, even more preferably at least 0.1, even more preferably at least 0.05, even more preferably at least 0.01 even more preferably at least 0.005 even more preferably at least 0.001 even more preferably at least 0.0005 even more preferably at least 0.0001 and most preferably at least 0.00001.

According to a more preferred embodiment, the filamentous fungal cell of the invention has a ratio NHR/HR, which is less than 200, even more preferably less than 50, less than 10 as measured by the following assay. Even more preferably the ratio of the filamentous fungal cell is less than 1, even more preferably less than 0.5, even more preferably less than 0.1, even more preferably less than 0.05, even more preferably less than 0.01 even more preferably less than 0.005 even more preferably less than 0.001 even more preferably less than 0.0005 even more preferably less than 0.0001 and most preferably less than 0.00001.

The ratio of NHR/HR is preferably measured by the assay as described in WO 02/052026 (table 2, p23).

Preferably, the filamentous fungal cell is deficient in a gene encoding a component involved in NHR, and/or has a decreased level of a component involved in NHR.

Even more preferably, the filamentous fungal cell is deficient in at least one of the following genes: hdfA or homologues thereof as identified in SEQ ID NO: 2 or 19, hdfB or homologues thereof as identified in SEQ ID NO: 5, or 22 or both, and/or has, preferably a decreased amount of at least one of the proteins encoded by these genes. Most preferably, the filamentous fungal cell is inducibly deficient n at least one of the following genes: hdfA or homologues thereof as identified in SEQ ID NO: 2 or 19, hdfB or homologues thereof as identified in SEQ ID NO: 5, or 22 or both, and/or has, preferably inducibly, a decreased amount of at least one of the proteins encoded by these genes.

According to another preferred embodiment, the filamentous fungal cell is such that in its genome, a gene involved in NHR has been replaced by a non-functional gene or by a selection marker or by another gene.

According to another preferred embodiment, the mutant has an increased level of a component involved in HR.

The filamentous fungus according to the invention may have been obtained by molecular biology techniques. A filamentous fungus obtained by such a genetic engineering approach is defined as a recombinant filamentous fungus. However, a recombinant filamentous fungus in the context of the invention could have been subjected earlier in time to mutagenesis technique to reach another wanted effect. According to a most preferred embodiment, the filamentous fungus obtained is a recombinant filamentous fungus.

Use of the Host Cell of the Invention

According to a preferred embodiment, there is provided a method which comprises at least the steps of introducing a polynucleotide of interest into the filamentous fungus of the invention, for example by the process of transformation or electroporation, and integration of said polynucleotide in the genetic material of said cell. Integration is a complex process wherein a nucleic acid sequence becomes part of the genetic material of a host cell. One step in the process of nucleic add integration is recombination; via recombination nucleic acid sequences are exchanged or Inserted and the introduced nucleic acid becomes part of the genetic material of a host cell. In principle two different ways of recombination are possible: homologous and illegitimate or NHR. Most (higher) eukaryotes do not or at least not significantly practice HR although the essential proteins to accomplish such a process are available. One reason for this phenomenon is that frequent use of homologous recombination in (higher) eukaryotes could lead to undesirable chromosomal rearrangements due to the presence of repetitive nucleic acid sequences. To accomplish HR via a method according to the invention, it is important to provide a polynucleotide, which has homology with a predetermined site. It is clear to a person skilled in the art that the percentage of homology and the length of (a) homologous region(s) play(s) an important role in the process of homologous recombination. The percentage of homology is preferably close to 100%. A person skilled in the art is aware of the fact that lower percentage of homology are also used in the field of homologous recombination, but dependent on, for example, the regions of homology and their overall distribution, can lead to a lower efficiency of HR but are still useful and therefore included in the present invention. Furthermore, the length of a (nearly) homologous region is approximately 3 kb which is sufficient to direct homologous recombination. At least one homologous region is necessary for recombination but more preferably two homologous regions flanking the nucleic acid of interest are used for targeted integration. The researcher skilled in the art knows how to select the proper percentage of homology, the length of homology and the amount of homologous regions. By providing such a homology a nucleic acid is integrated at every desired position within the genetic material of a host cell. It is clear to a person skilled in the art that the invention as disclosed herein is used to direct any nucleic acid (preferably DNA) to any pre-determined site as long as the length of homology and percentage of homology are high enough to provide/enable HR.

Before the present invention was made, a polynucleotide could not have always easily been integrated at every desired position into the genome of a given filamentous fungus. The method according to the invention is applied, for example, to affect the gene function in various ways, not only for complete inactivation but also to mediate changes in the expression level or in the regulation of expression, changes in protein activity or the subcellular targeting of an encoded protein. Complete inactivation, which can usually not be accomplished by existing methods such as antisense technology or RNAi technology (Zrenner R, Willmitzer L, Sonnewald U. Analysis of the expression of potato uriclinediphosphate-glucose pyrophosphorylase and its inhibition by antisense RNA. Planta. (1993); 190(2):247-52.) is useful for instance for the inactivation of genes controlling undesired side branches of metabolic pathways, for instance to increase the production of specific secondary metabolites such as (beta-lactam) antibiotics or carotenoids. Complete inactivation is also useful to reduce the production of toxic or unwanted compounds (chrysogenin in *Penicillium*; Aflatoxin in *Aspergillus*: MacDonald K D et al.: heterokaryon studies and the genetic control of penicillin and chrysogenin production in *Penicillium chrysogenum*. J Gen Microbiol. (1963) 33:375-83). Complete inactivation is also useful to alter the morphology of the organism in such a way that the fermentation process and down stream processing is improved.

The invention allows to replace existing regulatory sequences by alternative regulatory sequences to alter expression of endogenous genes (e. g. expression in response to specific inducers.

One aspect of the present invention relates to the replacement of an active gene by an inactive gene according to a method of the invention. Complete inactivation, which can usually not be accomplished by existing methods such as antisense technology or RNA1 technology, is useful for instance for the inactivation of genes controlling undesired side branches of metabolic pathways, for instance to increase the quality of bulk products such as starch, or to increase the production of specific secondary metabolites or to inhibit formation of unwanted metabolites.

Another aspect of the invention relates to the extensive metabolic reprogramming or engineering of a filamentous fungal cell. Introduction of complete new pathways and/or modification of unwanted pathways will lead to the obtention of a cell specifically adapted for the production of a specific compound such as a protein or a metabolite.

Another aspect of the present invention relates to the replacement of an inactive or altered gene by an active gene. For example, after successive rounds of classical mutagenesis, it often occurs the selected filamentous fungal strain has some endogenous genes altered or even inactivated during the random mutagenesis process.

In yet another aspect of the invention there is provided a method to introduce a substance conferring resistance for an antibiotic substance to a filamentous fungal cell. In yet a further aspect of the invention, there is provided a method to confer a desired property to a filamentous fungal cell. In a preferred embodiment a gene delivery vehicle is used to deliver a desired polynucleotide to a predetermined site. Gene delivery vehicles are well known in the art and have been earlier described in the description.

Also another preferred method according to a further aspect of the invention is to effectuate predictable expression of transgenes encoding novel products, for example by replacing existing coding sequences of genes giving a desired expression profile by those for a desired novel product. According to a more preferred embodiment, the filamentous fungus provided by the invention further comprises a DNA construct comprising a desired gene coding for a desired protein to be produced.

Preferably, the desired gene encoding the desired protein to be produced is inserted into an expression vector, which is subsequently used to transform the obtained host cell. In the expression vector, the DNA sequence may be operationally linked to appropriate expression signals, such as a promoter, optionally a signal sequence and a terminator, which are capable of directing the expression and synthesis of the protein in the host organism.

More preferably, the desired gene is operationally linked to a promoter and to a secretion signal. The strategy, which can be used to express the desired gene is the same as the one described under the section up regulation of the expression of a DNA sequence, whose expression product is involved in HR: increasing copy number, targeting integration, use of a promoter of a highly expressed gene, choice of the selection marker gene and combinations thereof.

The desired protein is preferably an enzyme. If the protein is not naturally secreted, the polynucleotide encoding the protein may be modified to have a signal sequence in accordance with techniques known in the art. The proteins, which are secreted may be endogenous proteins which are expressed naturally, but can also be heterologous. Heterologous means that the gene encoded by the protein is not produced under native condition in the wild type filamentous fungus. Examples of enzymes which may be produced by the filamentous fungi of the invention are carbohydrases, e.g. cellulases such as endoglucanases, β-glucanases, cellobiohydrolases or β-glucosidases, hemicellulases or pectinolytic enzymes such as xylanases, xylosidases, mannanases, galactanases, galactosidases, rhamnogalacturonases, arabanases, galacturonases, lyases, or amylolytic enzymes; phosphatases such as phytases, esterases such as lipases, proteolytic enzymes, oxidoreductases such as oxidases, transferases, or isomerases. More preferably, the desired gene encodes a phytase.

As another example existing coding sequences are modified so that the protein encoded has optimized characteristics for instance to make a protein with improved thermal characteristics and/or improved kinetic properties (Km, Kcat), and/or improved enzyme stability, and/or extended substrate range, and/or increased life span, etc. The invention further relates to the use of the filamentous fungus of the invention for produdng a polypeptide of interest. Alternatively, the filamentous fungus obtained may be used for produdng a secondary metabolite. Preferred secondary metabolites are carotenoid compounds, beta-lactam compounds, drugs, anti-tumor compounds, etc.

Preferably, the filamentous fungus as obtained in the present Invention is used for produdng the desired protein by culturing the transformed host cell under conditions conducive to the expression of the DNA sequence encoding the desired protein, and recovering the desired protein as described for example in the following references:

Li, Z. J., Shukla, V., Fordyce, A. P., Pedersen, A. G., Wenger, K. S., Marten, M. R. Fungal morphology and fragmentation behavior in a fed-batch *Aspergillus oryzae* fermentation at the production scale.

Biotechnol Bioeng. 2000 November 5; 70(3):300-12

Withers, J. M., Swift, R. J., Wiebe, M. G., Robson, G. D., Punt, P. J., van den Hondel, C. A Optimization and stability of glucoamylase production by recombinant strains of *Aspergillus niger* in chemostat culture.

Biotechnol Bioeng. 1998 Aug. 20; 59(4):407-18.

Amanullah, A., Christensen, L. H., Hansen, K., Nienow, A. W., Thomas, R. C. Dependence of morphology on agitation intensity in fed-batch cultures of *Aspergillus oryzae* and its implications for recombinant protein production.

Biotechnol Bioeng. 2002 Mar. 30; 77(7):815-26.

DNA Sequences and Polypeptides Encoded by these DNA Sequences

According to a further aspect of the invention, there are provided the following isolated cDNA sequences:

SEQ ID NO: 2 hdfA from *A. niger,*
SEQ ID NO: 19 hdfA from *Penicillium chrysogenum*
SEQ ID NO: 5 hdfB from *A. niger*
SEQ ID NO: 22 hdfB from *Penicillium chrysogenum* and homologues thereof.

Each SEQ ID NO: 1, 18, 4 and 21 corresponds respectively to the genomic DNA sequence associated with each cDNA sequence given above.

Each SEQ ID NO: 3, 20, 6 and 23 corresponds respectively to the protein sequence encoded by the respective cDNA sequence given above.

The sequence information as provided herein should not be so narrowly construed as to require inclusion of erroneously identified bases. The specific sequences disclosed herein can be readily used to isolate the complete gene from filamentous fungi, in particular *A. niger* or *Penicillium chrysogenum* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches Including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

"Homologous" is below defined. Homologous can be understood as meaning derived from other filamentous fungus than *Aspergillus niger* or *Penicillium chrysogenum*. Full length DNA from other organisms can be obtained in a typical approach, using cDNA or genomic DNA libraries constructed from other organisms, e.g. filamentous fungi, in particular from the species *Aspergillus Penicillium* by screening them.

The invention also encompasses paralogues of hdfA and/or hdfB. In the context of the invention, paralogues means DNA sequences homologous to SEQ ID NO: 1 or SEQ NO: 4 or SEQ ID NO: 18 or SEQ ID NO: 21 and derived from *A. niger* or *Penicillium chrysogenum* respectively.

For example, *Aspergillus* or *Penicillum* strains can be screened for homologous hdfA and/or hdfB polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to an hdfA and/or hdfB polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new hdfA and/or hdfB nucleic add sequence, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific br the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g. Sambrook et al., vide supra; and Ausubel et al., vide infra.

"Homologous" can also be understood as meaning functional equivalents.

The terms "functional equivalents" and "functional variants" are used interchangeably herein. Functional equivalents of hdfA and/or hdfB DNA are isolated DNA fragments that encode a polypeptide that exhibits a particular function of the hdfA and/or hdfB. A functional equivalent of an hdfA and/or hdfB polypeptide according to the invention is a polypeptide that exhibits at least one function as part of the NHR complex. Functional equivalents therefore also encompass biologically active fragments.

Functional protein or polypeptide equivalents may contain only conservative substitutions of one or more amino adds of sequences having SEQ ID NO: 3 or 6 or 20 or 23 or substitutions, insertions or deletions of non-essential amino adds. Accordingly, a non-essential amino acid is a residue that can be altered in one of these sequences without substantially altering the biological function. For example, amino acid residues that are conserved among the hdfA and/or hdfB proteins of the present invention, are predicted to be particularly unamenable to alteration. Furthermore, amino acids conserved among the hdfA and/or hdfB proteins according to the present invention are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding hdfA and/or hdfB proteins that contain changes in amino acid residues that are not essential for a particular biological activity. Such hdfA and/or hdfB proteins differ in amino acid sequence from SEQ ID NO: 3 or 6, or 20 or 23 and yet retain at least one of their biological activities. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the amino add sequence shown in SEQ ID NO 3 or 6 or 20 or 23. For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie at al. and the references cited therein.

An isolated nucleic add molecule encoding an hdfA and/or hdfB protein homologous to the protein according to SEQ ID NO: 3 or 6 or 20 or 23 can be created by introducing one or more nucleotide substitutions, additions or deletions into the coding nucleotide sequences according to SEQ ID NO: 2 or SEQ ID NO: 5, or SEQ ID NO: 19 or SEQ ID NO: 22 such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *A. niger* hdfA and/or hdfB protein. Orthologues of the *A. niger* hdfA and/or hdfB protein are proteins that can be isolated from other strains or species and possess a similar or identical biological activity. Such orthologues can readily be Identified as comprising an amino acid sequence that is substantially homologous to SEQ ID NO: 3 or 6 or 20 or 23.

"Homologous" can also be understood as meaning "substantially homologous". The term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 45%, preferably about 50%, preferably about 60%, preferably about 65%, more preferably about 70%, even more preferably abort 75%, 80%, 85%, 90%, 95%, 96%, 97%, 98% or 99% identity or more are defined herein as sufficiently identical.

Also, nucleic acids encoding other hdfA and/or hdfB family members, that have a nucleotide sequence that differs from SEQ ID NO: 2 or 5 or 19 or 22, are within the scope of the invention. Moreover, nucleic acids encoding hdfA and/or hdfB proteins from different species, which thus have a nucleotide sequence which differs from SEQ ID NO: 2 or 5 or 19 or 22.

Nucleic acid molecules corresponding to variants (e.g. natural allelic variants) and homologues of the hdfA and/or hdfB DNA of the invention can be isolated based on their homology to the hdfA and/or hdfB nucleic acids disclosed herein using the cDNAs disclosed herein or a suitable fragment thereof, as a hybridisation probe according to standard hybridisation techniques preferably under highly stringent hybridisation conditions.

"Stringency" of hybridisation reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reaunneal when complementary strands are present in an environment below their melting temperature. The higher the degree of desired homology between the probe and hybridizable sequence, the higher the relative temperature, which can be used. As a result, it follows that higher relative temperatures would tend to make the reaction conditions more stringent, while lower temperatures less so.

For additional details and explanation of stringency of hybridization reactions, see Ausubel et al, Current Protocols in Molecular Biology, Wiley Interscience' Publishers, (1995).

"Stringent conditions" or "high stringency conditions", as defined herein, may be identified by those that (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficdl/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 Rg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e. g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50 C. The skilled artisan will recognize how to adjust the temperature, ionic strength, etc. as necessary to accommodate factors such as probe length and the like. or by using an algorithm suitable for determining sequence similarity.

Homologous (similar or identical) sequences can also be determined by using a "sequence comparison algorithm". Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. An example of an algorithm that is suitable for determining sequence similarity is the BLAST algorithm, which is described in Altschul, et al., J. Mot. Biol. 215: 403-410 (1990).

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached.

The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=4, and a comparison of both strands.

The BLAST algorithm then performs a statistical analysis of the similarity between two sequences (see, e. g., Karlin & Altschul, Proc. Nat'l. Acad. Sci. USA 90: 5873-5787 (1993)). One measure of similarity provided by the BLAST algorithm is the smallest sum probability (P (N)), which provides an Indication of the probability by which a match between two nucleotide or amino acid sequences would occur by chance. For example, an amino acid sequence is considered similar to a protein such as a protease if the smallest sum probability in a comparison of the test amino add sequence to a protein such as a protease amino acid sequence is less than about 0.1, more preferably less than about 0.01, and most preferably less than about 0.001. Preferably the similarity is at least 40% homology to one of the DNA sequences having SEQ ID NO:2, 5, 19 and 22. More preferably the similarity is at least 50%, more preferably, at least 60%, more preferably at least 70%, more preferably at least 80%, more preferably at least 90%.

In addition to naturally occurring allelic variants of the hdfA and/or hdfB sequence, the skilled person will recognise that changes can be introduced by mutation into the nucleotide sequences of SEQ ID NO: 2 or 5 or 19 or 22, thereby leading to changes in the amino add sequence of the hdfA and/or hdfB protein without substantially altering the function of the hdfA and/or hdfB protein.

In another aspect of the invention, deteriorated hdfA and/or hdfB proteins are provided. Deteriorated hdfA and/or hdfB proteins are proteins, wherein at least one biological activity is decreased. Such proteins may be obtained by randomly introducing mutations along all or part of the hdfA and/or hdfB coding sequence, such as by saturation mutagenesis, and the resulting mutants can be expressed recombinantly and screened for biological activity. For instance, the art provides for standard assays for measuring their enzymatic activity and thus deteriorated proteins may easily be selected. Preferably, the assay is the one described earlier on (see for example WO02/052026 page 23 or the phenotypic screening assay).

In a preferred embodiment, the hdfA and/or hdfB protein has an amino acid sequence according to SEQ ID NO: 3 or 6 or 20 or 23. In another embodiment, the hdfA and/or hdfB polypeptide is substantially homologous to the amino acid sequence according to SEQ ID NO: 3 or 6 or 20 or 23 and retains at least one biological activity of a polypeptide according to SEQ ID NO:3 or 6 or 20 or 23, yet differs in amino acid sequence due to natural variation or mutagenesis as described above.

In a further preferred embodiment, the hdfA and/or hdfB protein has an amino acid sequence encoded by an isolated nucleic acid fragment capable of hybridising to a nucleic acid according to SEQ ID NO: 2 or 5 or 19 or 22, preferably under highly stringent hybridisation conditions.

Accordingly, the hdfA and/or hdfB protein is a protein which comprises an amino acid sequence at least about 60%, 65%, 70%, 75%, 80%, 85%, 90%, 95%, 96%, 97%, 98%, 99% or more homologous to the amino acid sequence shown in SEQ ID NO:3 or 6 or 20 or 23 and retains at least one functional activity of the polypeptide according to SEQ ID NO: 3 or 6 or 20 or 23.

Functional equivalents of a protein according to the invention can also be identified e.g. by screening combinatorial libraries of mutants, e.g. truncation mutants, of the protein of the invention for a given activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Younran (1992) Proc. Natl. Acad. Sci. USA 89:7811-7815; Delgrave at al. (1993) Protein Engineering 6(3):327-331).

In addition to the hdfA and/or hdfB gene sequences shown in SEQ ID NO: 2 and 5 and 19 and 22, it will be apparent for the person skilled in the art that DNA sequence polymorphisms that may lead to changes in the amino acid sequence of the hdfA and/or hdfB protein may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, can be used as hybridization probes or polymerase chain reaction (PCR) primers. Uses of the nucleic acid molecules of the present invention that do not encode a polypeptide having an hdfA and/or hdfB activity include, inter alfa, (1) isolating the gene encoding the hdfA and/or hdfB protein, or allelic variants thereof from a cDNA library e.g. from other organisms than *A. niger* or *Penicillium chrysogenum*; (2) in situ hybridization (e.g. FISH) to metaphase chromosomal spreads to provide precise chromosomal location of the hdfA and/or hdfB gene as described in Verma et al., Human Chromosomes: a Manual of Basic Techniques, Pergamon Press, New York (1988); (3) Northern blot analysis for detecting expression of hdfA and/or hdfB mRNA In specific tissues and/or cells and 4) probes and primers that can be used as a diagnostic tool to analyse the presence of a nucleic add hybridisable to the hdfA and/or hdfB probe in a given biological (e.g. tissue) sample.

Also encompassed by the invention is a method of obtaining a functional equivalent of an hdfA and/or hdfB gene or cDNA. Such a method entails obtaining a labelled probe that includes an isolated nucleic acid which encodes all or a portion of the sequence according to SEQ ID NO: 2 or 5 or 19 or 22 or a variant thereof; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the hdfA and/or hdfB gene.

In one embodiment, an hdfA and/or hdfB nucleic add of the invention is at least 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO: 1, or 2, or 4 or 5 or 18, or 19, or 21, or 22.

In another preferred embodiment an hdfA and/or hdfB polypeptide of the invention is at least 60%, 65%, 70%, 75%, 80%, 85%, 90%, 91%, 92%, 93%, 94%, 95%, 96%, 97%, 98%, 99%, or more homologous to the amino acid sequence shown in SEQ ID NO: 3 or 6 or 20 or 23.

The invention relates to DNA sequences having SEQ ID NO: 1, or 2, or 4, or 5, or 18, or 19, or 21, or 22 per se and to homologues thereof as defined above. DNA sequences related to these DNA sequences and obtained by degeneration of the genetic code are also part of the invention. DNA sequences related to DNA SEQ ID NO: 2, 5, 19, and 22 and obtained by hybridisation (see former paragraph) are also part of the invention. Isolated polypeptide encoded by these DNA sequences or homologues thereof as defined above are also part of the invention. Polypeptides hdfA and hdfB have a function involved in NHR. All these polypeptides can be used in the method of the invention to obtain filamentous fungi, which may have improved targeting efficiencies.

The invention will be illustrated in more detail in the following examples. Such examples are not intended to limit the scope of the invention.

EXAMPLES

Example 1

Figure 2:
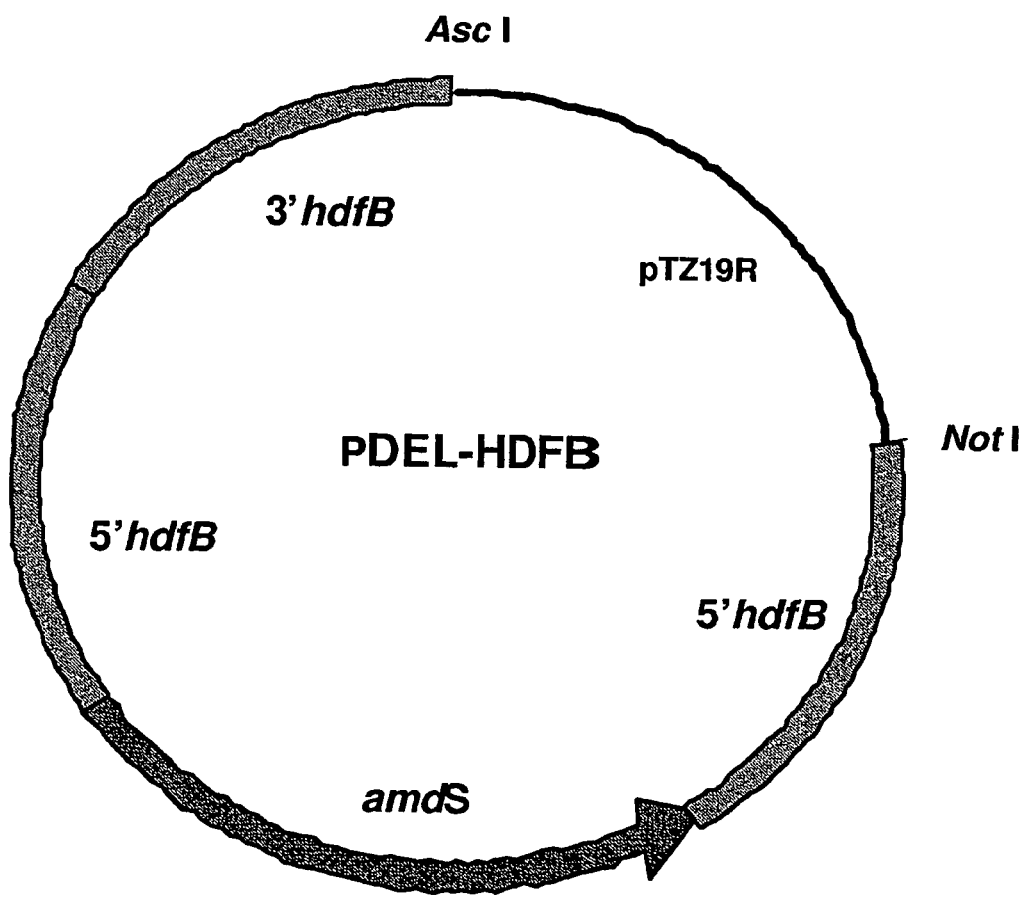
FIG. 2 depicts the replacement vector pDEL-HDFB used to inactive the hdfB gene in A. niger. The replacement vector comprises the hdfB flanking regions, the amdS marker and E. coli DNA. The E. coli DNA was removed by digestion with restriction enzymes Ascl and Notl, prior to transformation of the A. niger strains.

Identification of the hdfA and hdfB Genes and Construction of the Deletion Vectors Genomic DNA of *Aspergillus niger* strain CBS513.88 was sequenced and analyzed. Two genes with translated proteins annotated as homologues to KU70 and KU80, were identified and named hdfA and hdfB respectively. Sequences of the hdfA and hdfB loci, comprising the open reading frame (ORF) (with introns) and approximately 1000 bp 5' and 3' of the genes, are shown in sequence listings 1 and 4. Gene replacement vectors for hdfA and hdfB were designed according to known principles and constructed according to routine cloning procedures (see FIGS. 1 and 2). In essence, these vectors comprise approximately 1000 bp flanking regions of the hdf ORFs for homologous recombination at the predestined genomic loci. In addition, they contain the *A. nidulans* bi-directional amdS selection marker, in-between direct repeats. The general design of these deletion vectors were previously described in EP635574B and WO 98/46772.

Example 2

Inactivation of the hdfA Gene in *Aspergillus niger*

Figure 3:
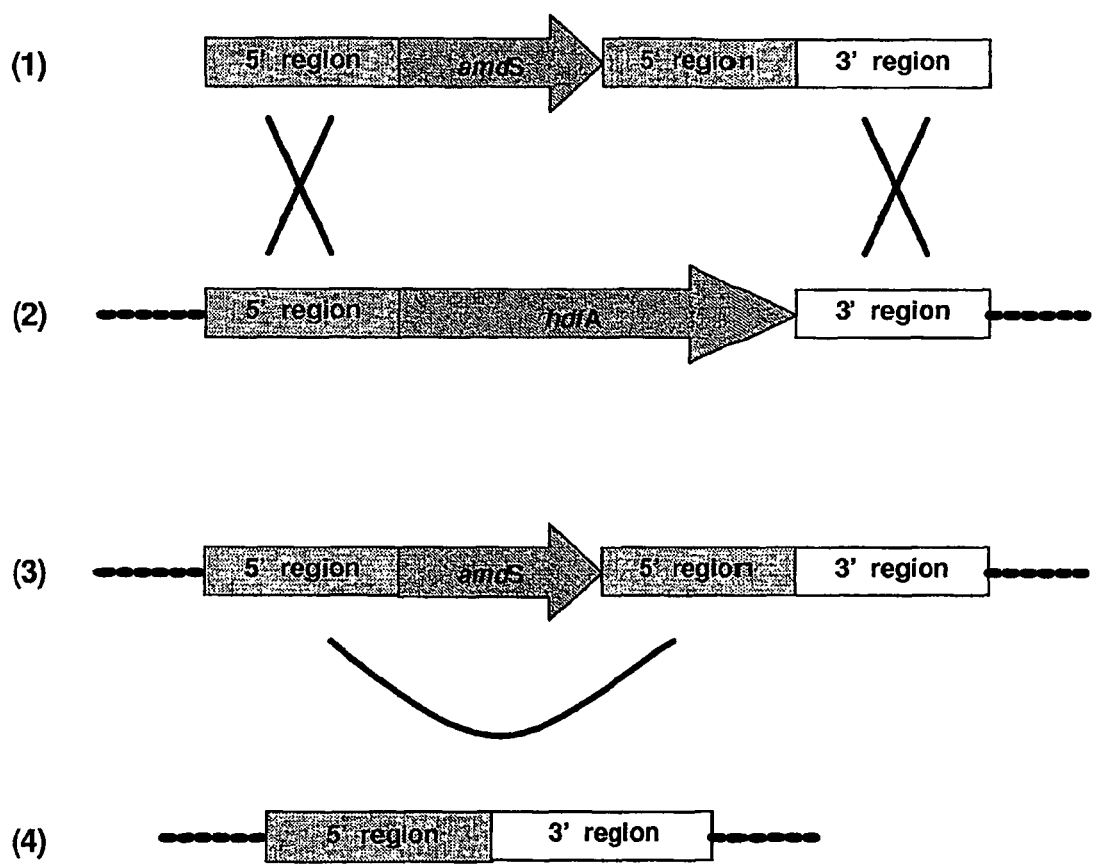
FIG. 3 depicts the strategy used to delete the hdfA gene of A. niger. The DNA construct used comprises the amdS selection marker flanked by homologous regions (5' and 3') of the hdfA gene (1). This construct integrates through double homologous recombination (X) at the genomic hdfA locus (2) and replaces the genomic hdfA gene copy (3). Subsequently, recombination over the direct repeats (U) removes the amdS marker, resulting in precise excision of the hdfA gene (4).

Linear DNA of deletion vector pDEL-HDFA (FIG. 1) was isolated and used to transform *Aspergillus niger* CBS513.88 using method earlier described (Biotechnology of Filamentous fungi: Technology and Products. (1992) Reed Publishing (USA); Chapter 6: Transformation pages 113 to 156). This linear DNA can integrate into the genome at the hdfA locus, thus substituting the hdfA gene by the amdS gene as depicted in FIG. 3. Transformants were selected on acetamide media and colony purified according to standard procedures as described in EP635574B. Spores were plated on fluoro-acetamide media to select strains, which lost the amdS marker. Growing colonies were diagnosed by PCR for integration at the hdfA locus and candidate strains tested by Southern analyses for deletion of the hdfA gene. Deletion of the hdfA gene was detectable by ~2.2 kb size reduction of DNA fragments covering the entire locus and hybridized to appropriate probes. Approximately 8 strains showed a removal of the genomic hdfA gene from a pool of approximately 400 initial transformants.

Strain dHDFA was selected as a representative strain with the hdfA gene inactivated.

Example 3

Inactivation of the hdfB Gene in *Aspergillus niger*

Figure 4:
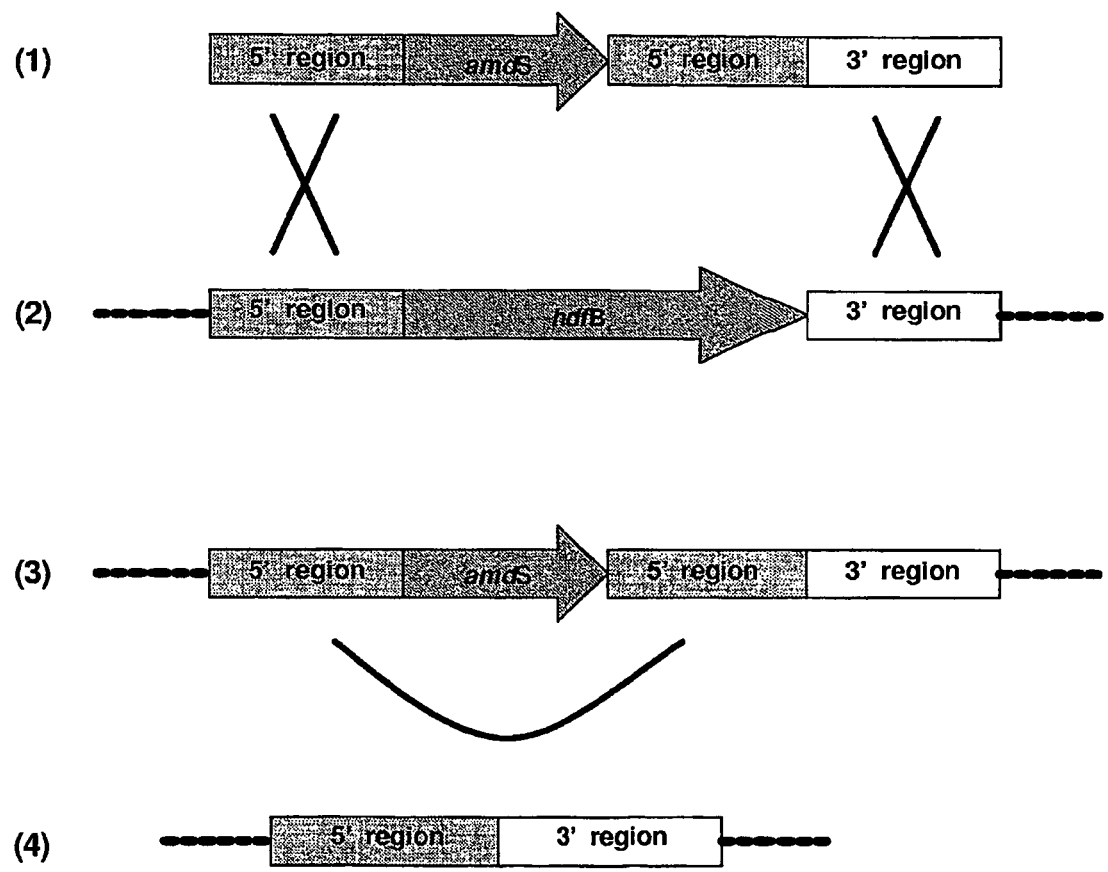
FIG. 4 depicts the strategy used to delete the hdfB gene of A. niger. The DNA construct comprises the amdS selection marker flanked by homologous regions (5' and 3') of the hdfB gene (1). This construct integrates through double homologous recombination (X) at the genomic hdfB locus (2) and replaces the genomic hdfB gene copy (3). Subsequently, recombination over the direct repeats (U) removes the amdS marker, resulting in precise excision of the hdfA gene (4).

Linear DNA of deletion vector pDEL-HDFB (FIG. 2) was isolated and used to transform the *Aspergillus niger* strain CBS513.88. This linear DNA can integrate into the genome at the hdfB locus, thus substituting the hdfB gene for amdS (FIG. 4). The same technique of gene replacement was used as the one described in example 2. Transformants were selected on acetamide media and colony purified according to standard procedures. Spores were plated on fluoro-acetamide media to select strains, which lost the amdS marker (EP 635574B). Growing colonies were diagnosed by PCR for integration at the hdfB locus and candidate strains tested by Southern analyses for deletion of the hdfB gene. Deletion of the hdfB gene was detectable by ~2.6 kb size reduction of DNA fragments covering the entire locus and hybridized to appropriate probes. Approximately 7 strains showed a removal of the genomic hdfB gene from a pool of approximately 370 Initial transformants.

Strain dHDFB was selected as a representative strain with the hdfB gene inactivated.

Example 4

Inactivation of the hdfA and hdfB Genes in *Aspergillus niger*

Linear DNA of deletion vector pDEL-HDFB (FIG. 2) was isolated and used to transform strain dHDFA obtained in Example 2. This linear DNA can integrate into the genome at the hdfB locus, thus substituting the hdfB gene for amdS (FIG. 4). The technique of gene replacement used is the one described in example 2. Transformants were selected on acetamide media and colony purified according to standard procedures. Spores were plated on fluoro-acetamide media to select strains, which lost the amdS marker. Growing colonies were diagnosed by PCR for integration at the hdfB locus and candidate strains tested by Southern analyses for deletion of the hdfB gene. Deletion of the hdfB gene was detectable by ~2.6 kb size reduction of DNA fragments covering the entire locus and hybridized to appropriate probes. Approximately 15 strains showed a removal of the genomic hdfB gene from a pool of approximately 380 initial transformants.

Strain dHDFAB was selected as a representative strain with both the hdfA and hdfB genes inactivated.

Example 5

Improved Targeting for Single Homologous Recombination Events

Figure 5:
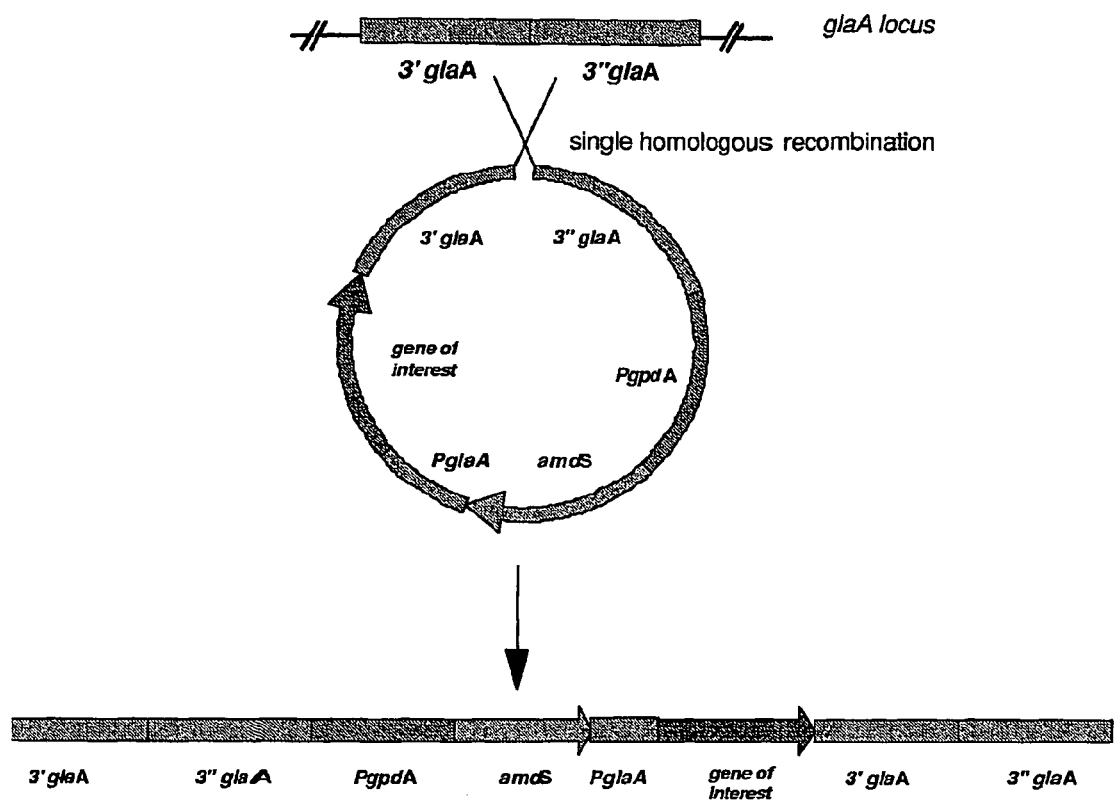
FIG. 5 depicts the schematic strategy used to integrate a DNA construct into the genome of *A. niger* through single homologous recombination. The expression vector comprises the selectable amdS marker and a gene of interest flanked by homologous regions of the glaA locus (3' glaA and 3" glaA respectively) to direct integration at the genomic glaA locus.

One mechanism by which DNA may integrate into the genome of *Aspergillus niger* at a predestined locus is through a single homologous recombination. Homologous DNA aligns and integrates at the genomic position by recombination (see FIG. 5). Two vectors were used to test the targeting efficiency through a single homologous recombination of *Aspergillus niger* strains obtained in examples 2, 3, and 4. The two vectors comprise regions homologous to the glucoamylase (glaA) locus to direct recombination and resulting integration (FIG. 5).

The first vector designed for such homologous integration has already been earlier described in WO 02/45524 (pGB-FIN11-EPO). This vector contains the gene coding for the proline specific endoprotease.

The second vector (pGBFIN11-PLA) contains the gene coding for phospholipase A1 (PLA1) from *A. oryzae*. The gene encoding this enzyme has already been published (Watanabe I, et al, Biosci. Biotechnol. Biochem. (1999), Vol 63, numero 5, pages 820-826). This gene was cloned into pGBFIN11 using the same technique as described in WO 02/045524 for the cloning of the proline specific endoprotease gene in pGBFIN11-EPO.

Strains CBS513.88, dHDFA, dHDFB and dHDFAB were transformed with either pGBFIN11-EPO or pGBFIN11-PLA plasmids according to transformation techniques earlier described in example 2. The results obtained were the same with both plasmids used. We found respectively, 5%, 10%, 10% and 10%, of transformants with plasmids integrated at the target locus. Hence, we concluded that the inactivation of at least one hdf-gene in *Aspergillus niger* leads to a significant increase of the targeting efficiency of these strains through a single homologous recombination event.

Example 6

Improved Targeting for Double Homologous Recombination Events at Several Different Loci The targeting efficiency was further assessed by transformation of the dHDFA strain with deletion vectors designed for the inactivation of a number of amylase encoding genes from the genome. Gene-flanking regions were cloned essentially as described in Example 1, and the resulting vectors were linearised and used to transform protoplasts of CBS513.88 and the dHDFA strain. The targeting frequency was assessed by PCR analyses and activity-based plate assays indicative of the inactivation of the corresponding genes. The latter was done by propagating transformants on PDA plates supplemented with 0.4% agar and subsequent staining with an iodine/potassium iodine solution (Lugol, Sigma L 6146). As can be seen in Table 1 below, the targeting frequency, as Judged by PCR analyses and/or activity-based plate assays indicative of the inactivation of the corresponding genes, was significantly improved over that observed with the CBS513.88 strain.

TABLE 1

Targeting frequencies of several deletion vectors in the dHDFA strain as compared with strain CBS513.88

| Gene | SEQ ID NO: | Plasmid | Targeting (%) CBS513.88 | dHDFA | Increase (fold) |
|---|---|---|---|---|---|
| amyBI | 9 | pDEL-AMYBI | 18 | 83 | 4.6 |
| amyBII | 12 | pDEL-AMYBII | 17 | 79 | 4.6 |
| amyA | 15 | pDEL-AMYA | 6 | 57 | 9.5 |

These findings provide further support for our conclusion that inactivation of at least one of the hdf genes in *Aspergillus niger* results in a significant increase of the targeting efficiency of vectors for integration through double homologous recombination.

Example 7

The Effect of Size Reduction of the Homologous Flanking Regions of the amyBII Gene on Targeting Frequencies In a separate series of experiments the effect of flanking region length on the transformation efficiency and targeting frequency through double homologous recombination was further investigated. Protoplasts of strains CBS513.88 and dHDFA were transformed with PCR fragments encompassing the *A. nidulans* amdS marker flanked by amyBII flanking regions of variable length. The data shown in Table 2 clearly demonstrate that, in addition to enhanced overall transformation efficiencies, targeting of the integrative cassettes was much improved in the dHDFA strain.

TABLE 2

Transformation efficiency and targeting frequencies of amyBII PCR deletion cassettes of variable length in the dHDFA strain and strain CBS513.88

| Length (kb) | Nr. of transformants | | Targeting (%) | |
|---|---|---|---|---|
| | CBS513.88 | dHDFA | CBS513.88 | dHDFA |
| 1.0 | 13 | 84 | 46 | 87[b] |
| 0.5 | 0 | 7 | n.d.[a] | |
| 0.25 | 0 | 1 | n.d.[a] | |

[a]not determined
[b]combined % for three variants tested

Example 8

Phenotype Analysis and Production of Polypeptide

No phenotypic differences were observed during growth of the dHDFA, dHDFB or dHDFAB strains on solid media or shake flasks. Strains dHDFA, dHDFB and dHDFAB transformed with plasmids pGBFIN11-EPO or pBGFIN-PLA all secreted active enzyme into the medium as determined according to the following procedures.

Solid media was the potato dextrose agar (PDA) medium (Difco, POTATO DEXTROSE AGAR, cultivation medium, catalogus. nr. 213400, year 1996-1997).

Shake flask experiments were performed in 100 ml of the medium as described in EP 635 574 B at 34° C. and 170 rpm in an Incubator shaker using a 500 ml baffled shake flask. After four days of fermentation, samples were taken to determine either the proline specific endoprotease activity or the phospholipase activity.

The proteolytic activity of the proline specific endoprotease was spectrophotometrically measured in time at pH 5 and about 37° C. using Z-Gly(cine)-Pro(line)-pNA as a substrate. 1U proline specific endoprotease is defined as the amount of enzyme which converts 1 micromol Z-Gly(cine)-Pro(line)-pNA per min at pH 5 and at 37° C.

To determine phospholipase PLA1 activity from *Aspergillus niger* (PLA1) spectrophotometrically, an artificial substrate is used: 1,2-dithiodioctanoyl phosphatidylcholine (diC8, substrate). PLA1 hydrolyses the sulphide bond at the A1 position, dissociating thio-octanoïc acid. Thio-octanoïc acid reacts with 4.4 dithiopyridine (color reagent, 4DTDP), forming 4-thiopyridone. 4-Thiopyridone is in tautomeric equilibrium with 4-mercaptopyridine, which absorbs radiation having a wavelength of 334 nm. The extinction change at that wavelength is measured. One unit is the amount of enzyme that liberates of 1 nmol thio-octanoic acid from 1,2-dithiodioctanoyl phosphatidylcholine per minute at 37° C. and pH 4.0.

The substrate solution is prepared by dissolving 1 g diC8 crystals per 66 ml ethanol and add 264 ml acetate buffer. The acetate buffer comprises 0.1 M Acetate buffer pH 3.85 containing 0.2% Triton-X100. The colour reagent is a 11 mM 4,4-dithiodipyridine solution. It was prepared by weighting 5.0 mg 4,4-dithiodipyridine in a 2 ml eppendorf sample cup and dissolving in 1.00 ml ethanol. 1.00 ml of mili-Q water was added.

Interestingly, morphologic changes such as color differences or colony appearance occurred less frequent for transformants obtained from the dHDFA, dHDFB and dHDFAB strains than for transformants obtained from CBS513.88. This could be due to reduction of random integrations (NHR) thus preventing unexpected phenotypic changes.

Example 9

Isolation of *Penicillium* Mutants with Improved Efficiency for Homologous Recombination by Mutagenesis To isolate mutants with an improved efficiency of gene targeting a combination of classical mutagenesis and molecular biology was applied. *Penicillium chrysogenum* (CBS 455.95) spores were obtained from colonies sporulating in YEPD (2% Yeast extract from Difco, 1% pepton from Difco, 2% glucose). These spores were washed in sterile tap water and 10 ml of a suspension containing $10^8$ conidiospores per ml was subjected to UV irradiation at 254 nm (Sylvania, 15 Watts Black Light Blue tube, model FT15T8/BLB). UV irradiation was applied for 7.5, 15 or 30 minutes while the suspensions were slowly shaken. These different irradiation times were chosen to obtain mild, medium and strong mutation rate levels in the cells. After one hour of recovery in the dark, the cells from these three time points were divided in two equal aliquots. The first sample was directly re-sporulated as earlier described (Hersbach, G J M, Van der Beek, C P and Van Duck, P W M. The Penicillins: properties, biosynthesis and fermentation. In: Vandamme E J (ed) Biotechnology of Industrial Antibiotics (pp 45-140). Marcel Dekker, New York) and the other sample was incubated for an extended recovery period in YNB medium (0.67% A w/v Yeast Nitrogen Base with amino acids (Difco), 2.0% w/v glucose) for 4 hours at 25 C before sporulation was induced.

Third mutagenized samples were obtained by germinating wild type spores overnight in YNB, followed by two washing steps in sterile tap water and resuspended in sterile tap water. Again UV irradiation was applied for 7.5, 15 and 30 minutes while the suspensions were slowly shaken. These samples were directly re-sporulated (as described above) after one hour of recovery in the dark.

To select the wanted mutants from these mutagenesized populations, the mutagenesized populations were inoculated in YEPD medium. After germination the development of cells was followed using standard light microscopy. When the average hyphae of a culture was nicely developing, cells were harvested and incubated with lysing enzymes to obtain protoplasts. Protoplasts were transformed with two DNA fragments carrying expression cassettes of functional selection markers, ble and amdS. The gene ble encodes a protein capable of conferring resistance to phleomycin (Kolar M, Punt P J, van den Hondel C A, Schwab H. Transformation of *Penicillium chrysogenum* using dominant selection markers and expression of an *Escherichla coil* lacZ fusion gene. Gene. 1988; 62(1):127-34). The gene amdS encodes a protein enabling cells to grow on acetamide as the sole nitrogen source (as described in EP635 574B). Techniques applied for the transfer of DNA to protoplasts of *P. chrysogenum* are well known in the art and are described in many references, including Finkelstein and Ball (eds.), Biotechnology of filamentous fungi, technology and products, Butterworth-Heinemann (1992); Bennett and Lasure (eds.) More Gene Manipulations in fungi, Academic Press (1991); Turner, in: Pühler (ed), Biotechnology, second completely revised edition, VHC (1992). The Ca-PEG mediated protoplast transformation is used as described in EP635574.

To select targeted integration of these expression cassettes to specific loci in the *Penicillium* genome short homologous stretches of DNA were added via PCR on both sides of the DNA fragments. Three types of construct were made: the first type contains homologous stretches of DNA of 30 bp, the second of 50 bp and the third of 100 bp. Selection was performed transforming mutants obtained from the nine sporulated batches with two DNA constructs (We and amdS) with 30, 50 or 100 bp homologous strectches defining 27 distinct batches. The ble gene was targeted to the niaD locus, thereby disrupting the nitrate reductase gene (Gouka R J, van Hartingsveldt W, Bovenberg R A, van den Handel C A, van Gorcom R F. Cloning of the nitrate-nitrite reductase gene cluster of *Penicillium chrysogenum* and use of the niaD gene as a homologous selection marker. J Biotechnol. 1991 September; 20(2):189.99), enabling direct selection of transformants on plates containing chlorate, as cells become resistant to chlorate. The amdS gene was targeted to the sutB locus, thereby disrupting the sulphate permease gene (van de Kamp M, Pizzinini E, Vos A, van der Lende T R, Schuurs T A, Newbert R W, Turner G, Konings W N, Driessen A J. Sulfate transport in *Penicillum chrysogenum*: cloning and characterization of the sutA and sutB genes. J. Bacterial. 1999 December; 181(23):7228-34), enabling direct selection of transformants on plates containing selenate. Transformants were first selected on chlorate and then tested for selenate. Furthermore, the presence of the selection markers was demonstrated by growth on plates containing acetamide as sole nitrogen source (EP635574B) and subsequently on plates containing phleornydne. As control wild type *P. chrysogenum* CBS 455.95 was also transformed with the same DNA fragments. Mutants with both selection markers present and resistant against both chlorate and selenate are strains with improved targeted integration.

The invention claimed is:

1. A mutant of a parent filamentous fungal cell, the parent organism having a preference for non-homologous recombination (NHR), wherein the filamentous fungal host cell is a *Penicillium* species, wherein the ratio of NHR/homologous recombination (HR) is decreased in the mutant as compared to said ratio in said parent organism measured under the same conditions, wherein the mutant is deficient in a gene encoding a component involved in NHR, and/or has a decreased level of a component involved in NHR, wherein the mutant is, optionally inducibly, deficient in at least one filamentous fungal homologue of yeast KU80, yeast KU70, or both, or has, optionally inducibly, a decreased amount of at least one of the proteins encoded by these genes.

2. The mutant according to claim 1, wherein in the genome of the organism a gene involved in NHR has been replaced by a non-functional variant.

3. The mutant according to claim 1, wherein the mutant has an increased level of a component involved in HR.

4. The mutant according to claim 1, wherein the mutant is a recombinant mutant.

5. The mutant according to claim 1, wherein the mutant is transformed with a DNA construct comprising a DNA sequence comprising a gene of interest encoding a polypeptide of interest.

6. The mutant according to claim 1, wherein the *Penicillium* is a *Penicillium chrysogenum* or *Penicillium citrinum* species.

7. A method for producing a polypeptide of interest, comprising:
(a) culturing the mutant according to claim 1, under conditions conducive to expression of the DNA sequence encoding the polypeptide; and
(b) recovering the polypeptide of interest.

8. A method for producing a metabolite, comprising:
(a) culturing the mutant according to claim 1, under conditions conducive to produce the metabolite; and
(b) recovering the metabolite.

9. The method according to claim 8, wherein the metabolite is a carotenoid compound or a beta-lactam compound.

10. A method for increasing the efficiency of targeted integration of a polynucleotide to a pre-determined site into the genome of a filamentous fungal cell with a preference for NHR, wherein said polynucleotide has a region of homology with said pre-determined site, wherein said filamentous fungal cell belongs the genus *Penicillium*, comprising providing a mutant of a parent filamentous fungal cell, wherein the ratio of NHR/HR is decreased in the mutant as compared to said ratio in said parent organism measured under the same conditions, wherein said mutant is deficient in a gene encoding a component involved in NHR, and/or has a decreased level of a component involved in NHR, wherein the mutant is, optionally inducibly, deficient in at least one filamentous fungal homologue of yeast KU80, yeast KU70, or both, or has, optionally inducibly, a decreased amount of at least one of the proteins encoded by these genes.

11. The method of claim 10, wherein the steering comprises providing a mutant of a parent filamentous fungal cell, wherein the ratio of NHR/HR is decreased in the mutant as compared to said ratio in said parent organism measured under the same conditions.

12. The method of claim 10, wherein the steering comprises providing a mutant which is deficient in a gene encoding a component involved in NHR, and/or has a decreased level of a component involved in NHR.

13. The method of claim 10, wherein a gene involved in NHR has been replaced by a non-functional variant.

14. The method according to claim 10, wherein the mutant has an increased level of a component involved in HR.

* * * * *

SEQUENCE LISTING

```
<160> NUMBER OF SEQ ID NOS: 23

<210> SEQ ID NO 1
<211> LENGTH: 2284
<212> TYPE: DNA
<213> ORGANISM: Aspergillus niger

<400> SEQUENCE: 1
atggcggacg gcaacccaca tcgggaagat gaggcggccg aggaagaaga ggagattgat      60
gagactgtac gcaaatttac ccatgaactt ggactggaac tctggaactg acaataagat     120
```

-continued

| | |
|---|---|
| cagagctaca aaccagtcaa agatgcggtc ctcttcgcaa tcgatgtcag cgattccatg | 180 |
| ttgacgcctc gcccctcagc agatcctaag aaacacaccc aagaatcacc caccacggca | 240 |
| gcgctcaaat gcgcctatca cttcatgcaa caacgaatca tatcaaatcc acaagacatg | 300 |
| atgggtgttt tgctgttcgg gacccaggcg tccaagttct tgaagaaga tgaagacagt | 360 |
| cggggagacc tgtcctaccc caactgctac ctcttcactg atctggatgt tccttcggct | 420 |
| catgaggtca aaggacttcg agcactggta gatgatgaag agactcaag ggaggttcta | 480 |
| tctccagcga aagagcaggt ctctatggca aacgtcctat tttgcgccaa ccagatattc | 540 |
| acatccagag cgccaaattt cctctcccgg cgtttgttca tcataaccga caatgacaac | 600 |
| ccccatggtg atgataaaac cctgcggtca gcggcgactg tacgtgctaa ggatctttac | 660 |
| gatcttggtg tcacaattga gctgtttccg atctcacgcc ctgagcatga gttcaagaac | 720 |
| agcaagttct atgacgtaag ctatcatact ctatagcaaa gtggcagggg tcgatactca | 780 |
| ctacagatac aaaggatatt atctacaagt cattgcccag cgatccagag cgcctgcat | 840 |
| atctacaatc tgattcaaaa gcggcgactg cgaccgggga cgggatttca ctcctcaaca | 900 |
| cgcttctgtc cagtattaat tcgagaacgg ttccgcgtcg cactcatttt tcgaacatgc | 960 |
| ctttagaact tggcccagac ttcagaattt cggtatcggg ctatatactc ttacgaaggc | 1020 |
| aagcgcccgc tagaaactcc ttcatctggc tgaacggcga aagcctgtg gtcgcgaaag | 1080 |
| gagtgacttc ccactccgca gatgatactg gccggactgt cgagaaatgg agatcagaa | 1140 |
| aggcatataa gttcggtggc gaccaagtaa ccttttcgcc tgatgagcag aaggcgctta | 1200 |
| gggatttcgg tgagccagta atccgggtta ttgggttcaa gcctatcact gcgcttccat | 1260 |
| tctgggcaaa cgtcaagcac ccatatttta tctatccatc cgaggaagac tatgtaggct | 1320 |
| cctcgcgagt attttccgca ttgcatcaga ctcttttgcg ttccaagaag atggcactcg | 1380 |
| tctggttcat tgcacgcaag ggtgctggcc ccgttctcgc cgctatgatc gcaggcgaag | 1440 |
| aaaagcttga tgagaatggc gtacaaaaat accctcctgg catgtggatt cttcccctcc | 1500 |
| ccttcgcaga cgatatccgg cagaaccccg aaacaacgtt gaatgtcgcc ccggagtcat | 1560 |
| tgattgatca gatgcgcgtg atcgtccagc aactgcagct gccgaaggga gtgtacgagc | 1620 |
| ctctcaaata ccccaatcca tgtaagtcac ttctgtcttg cattgctcgt atacgatgaa | 1680 |
| cgagaagctg acagcccgtg atcagcccct caatggcatt accgcatcct acaagctctc | 1740 |
| gcattagacg aagatctccc cgaaaaacca gaagacaaaa ccattccgaa ataccgccaa | 1800 |
| atcgacaagg taaatccacc acacccaaca cgagaaataa ccctccaggc gtccaactta | 1860 |
| ctgacaattg caccacagcg cgccggtgac tacgtattat cctgggccga cgaactcgaa | 1920 |
| aagcaatacg ccaaaacctc agcagcggcc cctcgcccaa ccagcaccct cgtgaaacga | 1980 |
| ggatcaaaag accgagcaag cgaaaccgag gactccaagc catcgaaaaa gatcaaggtt | 2040 |
| gaggaagact ctggaagcct agaggaggaa gtccgcaggc atcacaagaa gggaacgcta | 2100 |
| tccaaggtaa gccaccacag gctttctaca cgtcctcgtg atggcaaata tgacatcgta | 2160 |
| ttaaccggcg gttttctagc ttacggtcgc tatcctcaag gacttcttga cttccaatgg | 2220 |
| acgctcaaat gccggtaaga aggcggatct tattgagcgg gtagaggagt tcttggagca | 2280 |
| gtga | 2284 |

<210> SEQ ID NO 2
<211> LENGTH: 1947
<212> TYPE: DNA
<213> ORGANISM: Aspergillus niger

<400> SEQUENCE: 2

```
atggcggacg gcaacccaca tcgggaagat gaggcggccg aggaagaaga ggagattgat      60
gagactagct acaaaccagt caaagatgcg gtcctcttcg caatcgatgt cagcgattcc     120
atgttgacgc ctcgcccctc agcagatcct aagaaacaca cccaagaatc acccaccacg     180
gcagcgctca aatgcgccta tcacttcatg caacaacgaa tcatatcaaa tccacaagac     240
atgatgggtg ttttgctgtt cgggacccag gcgtccaagt tctttgaaga agatgaagac     300
agtcggggag acctgtccta ccccaactgc tacctcttca ctgatctgga tgttccttcg     360
gctcatgagg tcaaaggact tcgagcactg gtagatgatg aaggagactc aagggaggtt     420
ctatctccag cgaaagagca ggtctctatg gcaaacgtcc tattttgcgc caaccagata     480
ttcacatcca gagcgccaaa tttcctctcc cggcgtttgt tcatcataac cgacaatgac     540
aacccccatg gtgatgataa aaccctgcgg tcagcggcga ctgtacgtgc taaggatctt     600
tacgatcttg tgtcacaat tgagctgttt ccgatctcac gccctgagca tgagttcaag     660
aacagcaagt tctatgactc attgcccagc gatccagagg cgcctgcata tctacaatct     720
gattcaaaag cggcgactgc gaccggggac gggatttcac tcctcaacac gcttctgtcc     780
agtattaatt cgagaacggt tccgcgtcgc actcattttt cgaacatgcc tttagaactt     840
ggcccagact tcagaatttc ggtatcgggc tatatactct tacgaaggca agcgcccgct     900
agaaactcct tcatctggct gaacggcgag aagcctgtgg tcgcgaaagg agtgacttcc     960
cactccgcag atgatactgg ccggactgtc gagaaatggg agatcagaaa ggcatataag    1020
ttcggtggcg accaagtaac cttttcgcct gatgagcaga aggcgcttag ggatttcggt    1080
gagccagtaa tccgggttat tgggttcaag cctatcactg cgcttccatt ctgggcaaac    1140
gtcaagcacc catatttat ctatccatcc gaggaagact atgtaggctc ctcgcgagta    1200
ttttccgcat tgcatcagac tcttttgcgt tccaagaaga tggcactcgt ctggttcatt    1260
gcacgcaagg gtgctggccc cgttctcgcc gctatgatcg caggcgaaga aaagcttgat    1320
gagaatggcg tacaaaaata ccctcctggc atgtggattc ttcccctccc cttcgcagac    1380
gatatccggc agaaccccga acaacgttg aatgtcgccc cggagtcatt gattgatcag    1440
atgcgcgtga tcgtccagca actgcagctg ccgaagggag tgtacgagcc tctcaaatac    1500
cccaatccat cccttcaatg gcattaccgc atcctacaag ctctcgcatt agacgaagat    1560
ctccccgaaa aaccagaaga caaaaccatt ccgaaatacc gccaaatcga caagcgcgcc    1620
ggtgactacg tattatcctg ggccgacgaa ctcgaaaagc aatacgccaa acctcagca    1680
gcggccctc gcccaaccag caccctcgtg aaacgaggat caaaagaccg agcaagcgaa    1740
accgaggact ccaagccatc gaaaaagatc aaggttgagg aagactctgg aagcctagag    1800
gaggaagtcc gcaggcatca caagaaggga acgctatcca agcttacggt cgctatcctc    1860
aaggacttct tgacttccaa tggacgctca aatgccggta agaaggcgga tcttattgag    1920
cgggtagagg agttcttgga gcagtga                                         1947
```

<210> SEQ ID NO 3
<211> LENGTH: 648
<212> TYPE: PRT
<213> ORGANISM: Aspergillus niger

<400> SEQUENCE: 3

```
Met Ala Asp Gly Asn Pro His Arg Glu Asp Glu Ala Ala Glu Glu Glu
1               5                   10                  15
```

```
Glu Glu Ile Asp Glu Thr Ser Tyr Lys Pro Val Lys Asp Ala Val Leu
            20                  25                  30

Phe Ala Ile Asp Val Ser Asp Ser Met Leu Thr Pro Arg Pro Ser Ala
            35                  40                  45

Asp Pro Lys Lys His Thr Gln Glu Ser Pro Thr Thr Ala Ala Leu Lys
 50                  55                  60

Cys Ala Tyr His Phe Met Gln Gln Arg Ile Ile Ser Asn Pro Gln Asp
 65                  70                  75                  80

Met Met Gly Val Leu Leu Phe Gly Thr Gln Ala Ser Lys Phe Phe Glu
                85                  90                  95

Glu Asp Glu Asp Ser Arg Gly Asp Leu Ser Tyr Pro Asn Cys Tyr Leu
            100                 105                 110

Phe Thr Asp Leu Asp Val Pro Ser Ala His Glu Val Lys Gly Leu Arg
            115                 120                 125

Ala Leu Val Asp Asp Glu Gly Asp Ser Arg Glu Val Leu Ser Pro Ala
130                 135                 140

Lys Glu Gln Val Ser Met Ala Asn Val Leu Phe Cys Ala Asn Gln Ile
145                 150                 155                 160

Phe Thr Ser Arg Ala Pro Asn Phe Leu Ser Arg Arg Leu Phe Ile Ile
            165                 170                 175

Thr Asp Asn Asp Asn Pro His Gly Asp Asp Lys Thr Leu Arg Ser Ala
            180                 185                 190

Ala Thr Val Arg Ala Lys Asp Leu Tyr Asp Leu Gly Val Thr Ile Glu
            195                 200                 205

Leu Phe Pro Ile Ser Arg Pro Glu His Glu Phe Lys Asn Ser Lys Phe
            210                 215                 220

Tyr Asp Ser Leu Pro Ser Asp Pro Glu Ala Pro Ala Tyr Leu Gln Ser
225                 230                 235                 240

Asp Ser Lys Ala Ala Thr Ala Thr Gly Asp Gly Ile Ser Leu Leu Asn
            245                 250                 255

Thr Leu Leu Ser Ser Ile Asn Ser Arg Thr Val Pro Arg Arg Thr His
            260                 265                 270

Phe Ser Asn Met Pro Leu Glu Leu Gly Pro Asp Phe Arg Ile Ser Val
            275                 280                 285

Ser Gly Tyr Ile Leu Leu Arg Arg Gln Ala Pro Ala Arg Asn Ser Phe
            290                 295                 300

Ile Trp Leu Asn Gly Glu Lys Pro Val Val Ala Lys Gly Val Thr Ser
305                 310                 315                 320

His Ser Ala Asp Asp Thr Gly Arg Thr Val Glu Lys Trp Glu Ile Arg
            325                 330                 335

Lys Ala Tyr Lys Phe Gly Gly Asp Gln Val Thr Phe Ser Pro Asp Glu
            340                 345                 350

Gln Lys Ala Leu Arg Asp Phe Gly Glu Pro Val Ile Arg Val Ile Gly
            355                 360                 365

Phe Lys Pro Ile Thr Ala Leu Pro Phe Trp Ala Asn Val Lys His Pro
            370                 375                 380

Tyr Phe Ile Tyr Pro Ser Glu Glu Asp Tyr Val Gly Ser Ser Arg Val
385                 390                 395                 400

Phe Ser Ala Leu His Gln Thr Leu Leu Arg Ser Lys Lys Met Ala Leu
            405                 410                 415

Val Trp Phe Ile Ala Arg Lys Gly Ala Gly Pro Val Leu Ala Ala Met
            420                 425                 430
```

-continued

```
Ile Ala Gly Glu Glu Lys Leu Asp Glu Asn Gly Val Gln Lys Tyr Pro
            435                 440                 445

Pro Gly Met Trp Ile Leu Pro Leu Pro Phe Ala Asp Asp Ile Arg Gln
        450                 455                 460

Asn Pro Glu Thr Thr Leu Asn Val Ala Pro Glu Ser Leu Ile Asp Gln
465                 470                 475                 480

Met Arg Val Ile Val Gln Gln Leu Gln Leu Pro Lys Gly Val Tyr Glu
                485                 490                 495

Pro Leu Lys Tyr Pro Asn Pro Ser Leu Gln Trp His Tyr Arg Ile Leu
            500                 505                 510

Gln Ala Leu Ala Leu Asp Glu Asp Leu Pro Glu Lys Pro Glu Asp Lys
        515                 520                 525

Thr Ile Pro Lys Tyr Arg Gln Ile Asp Lys Arg Ala Gly Asp Tyr Val
530                 535                 540

Leu Ser Trp Ala Asp Glu Leu Glu Lys Gln Tyr Ala Lys Thr Ser Ala
545                 550                 555                 560

Ala Ala Pro Arg Pro Thr Ser Thr Leu Val Lys Arg Gly Ser Lys Asp
                565                 570                 575

Arg Ala Ser Glu Thr Glu Asp Ser Lys Pro Ser Lys Lys Ile Lys Val
            580                 585                 590

Glu Glu Asp Ser Gly Ser Leu Glu Glu Val Arg Arg His His Lys
        595                 600                 605

Lys Gly Thr Leu Ser Lys Leu Thr Val Ala Ile Leu Lys Asp Phe Leu
        610                 615                 620

Thr Ser Asn Gly Arg Ser Asn Ala Gly Lys Lys Ala Asp Leu Ile Glu
625                 630                 635                 640

Arg Val Glu Glu Phe Leu Glu Gln
                645
```

<210> SEQ ID NO 4
<211> LENGTH: 2651
<212> TYPE: DNA
<213> ORGANISM: Aspergillus niger

<400> SEQUENCE: 4

```
atggccgata aagaggcaac tgtctacatc gtggactgcg gcaagtccat gggggagcgg     60
cgtcatggtc gcgaagtgac ggatctcgac tgggcgatgc aatatgtttg ggatcgtatt    120
acagggacgg tgagatcctt attcttgaga atcatatcat acatgaaagc ttatgttttg    180
gataggtggc cactgacga aaaatggctt tgatcggtgt tcttgggctc aggacagatg    240
gtgagtgact agcctcccgg gtacagttgg tagttgtagt ttgctggtcg gggctaatgc    300
aggaacgtcc agaaaccgct aatgagttgg aggatgatcc tgattattcg catatctcgg    360
ttttgtctgg gattaaacag tatgattcat ttttgtctgc tgatcctctg gttattcgct    420
gatgaactat aggtttctta tgccggatat ccggggtttg agcgaccgaa taaagcctag    480
caagactaat aagggagatg gtgagttact cttcttgtat ggaattggag tgattggggc    540
tgagccgatg aatatagcta tctctgcact tgtgctcgcg attcagatga ttatcactca    600
gtgcaagaaa ctgaagtaca agcgcaggat tgtcctggtt actaatgggc agggcccgat    660
gaacccggat aatcttagtg aaataacgaa gaagattaag gaggataaca ttgaacttat    720
tattctgtta gtgtcaattg atacactgag agaaccgggg tactaacatg ctgcagggga    780
ccagactttg atgatcctga atatggggtg aagaggaag ataagatcc gcgaaaggta     840
tttaacttcg ttccatatgc tctagactaa taataacaat ggctacaggc cgaaaatgaa    900
```

-continued

```
acactcctgc gtagtcttgc cgaagactgc gaaggagcct atggaaccct agaacaagct      960
gttgcggagc tggaaactcc tcgtgtgaaa accacaagga taacagcaag cttcaagggc     1020
catttgcaac taggaaaccc cgcagaatat gatactgcag ttcggatccc tgtggagcgc     1080
tactacagga catacgttgc aaaagctccg tcggctagtc agttcacagt acgtaacgaa     1140
gaggagatgg gaatggccgc ggccgcagcc ggctcgcagg aaggtagttc ccttgtgggt     1200
gttcgaaaca acaggtccta ccaaattgac gatgggacta ctgaagaagg ggtgagggac     1260
gtggatcgag agcaacttgc caagggttat gagtacgggc ggacattggt ccctattagc     1320
gagacggatg agaatatcac cacccctgag acatttgcgg ctatcgagct tcttgggttt     1380
atacagagcg atcgggtgag ttctacccte caataactgt tattatgctg ctaagtgggt     1440
tttgccatta gtatgatcga tacatgcaca tgtcgacgac aaacatcatc atcgcgcagc     1500
gcgcgaatga caaggcagca ctcgctcttt cctctttcat acatgcgctg ttcgagctgg     1560
aatcgtacgc tgtcgcccgt atggtgctaa aggagaacaa accccctgtc atagtcgtgc     1620
ttgcgccatc aatcgaaccc gactacgagt gtctcctcga agcgcagttg ccattcgcag     1680
aagacgtacg aacgtaccgc ttccctccac tcgacagagt cattacagtg tctggtaaag     1740
tggtgacaca gcatcgaaac ctacccaacg acgatctgtt gaatgcgatg acaaatacg      1800
tgaaaagcat ggagcttacc gatatggacg agaacgggtg agaagaattg gaagtgatct     1860
caacttcact gctgactttg tacaaagtga cccgacggaa tctctcccaa tagacgactc     1920
tttctctcca gtcctgcacc ggatcgactc cgcaatccgt caccgtgcca ttcatcccaa     1980
cgaccctatc ccgcccccag cctcagtcct aacgaagttc tcccaccctc cggatgacct     2040
cgtcgagaag tccaagaaat acctagacaa gctagtagca gtgtcggacg tcaagaaagg     2100
tcagtccatc tcggccttga gcctcttagg ccccccatcat actcacagtg atgaatctag     2160
tcccaccaaa aaccaaaggc accaaacgga cccgcgaaac cgagaagcca ctatccggtc     2220
tcgacgtcga tgcccttctc caccaagaga agcgcacgaa gatctcaccc aacaacgcaa     2280
ttcccgagtt taagcagacg ctctcgcagg cagagaacat cgagatcatc aaggatgcag     2340
tgaagcagat gagcactatc attgaagacc aaatcaggca tagtcttggc gatgttaatt     2400
atcatcgggt cactgagggg ctaggtgtga tgcgggagga actgatcgat tatgaggaac     2460
tgctctgta taacgattc ttgaagcagc tgaaggagaa gttgttgaaa gaggagctcg      2520
gtggggatcg acgggagctg tggtggctgc taagaaggag taagttgggg ttgattgaac     2580
agagggagtc ggaacactct gaggtgagag aagaggaagc gaaggcgttt atgtctatgg     2640
ctgctaagtg a                                                          2651
```

<210> SEQ ID NO 5
<211> LENGTH: 2178
<212> TYPE: DNA
<213> ORGANISM: Aspergillus niger

<400> SEQUENCE: 5

```
atggccgata aagaggcaac tgtctacatc gtgggactgcg gcaagtccat gggggagcgg       60
cgtcatggtc gcgaagtgac ggatctcgac tgggcgatgc aatatgtttg ggatcgtatt      120
acagggacgg tggccactgg acgaaaaatg ctttgatcg tgttcttgg gctcaggaca         180
gatgtttgct ggtcggggct aatgcaggaa cgtccagaaa ccgctaatga gttggaggat      240
gatcctgatt attcgcatat ctcggttttg tctgggatta aacagtttct tatgccggat      300
```

-continued

```
atccggggtt tgagcgaccg aataaagcct agcaagacta ataagggaga tgctatctct    360
gcacttgtgc tcgcgattca gatgattatc actcagtgca agaaactgaa gtacaagcgc    420
aggattgtcc tggttactaa tgggcagggc ccgatgaacc cggataatct tagtgaaata    480
acgaagaaga ttaaggagga taacattgaa cttattattc tgggaccaga ctttgatgat    540
cctgaatatg gggtgaaaga ggaagataaa gatccgcgaa aggccgaaaa tgaaacactc    600
ctgcgtagtc ttgccgaaga ctgcgaagga gcctatggaa ccctagaaca agctgttgcg    660
gagctggaaa ctcctcgtgt gaaaaccaca aggataacag caagcttcaa gggccatttg    720
caactaggaa accccgcaga atatgatact gcagttcgga tccctgtgga gcgctactac    780
aggacatacg ttgcaaaagc tccgtcggct agtcagttca cagtacgtaa cgaagaggag    840
atgggaatgg ccgcggccgc agccggctcg caggaaggta gttcccttgt gggtgttcga    900
aacaacaggt cctaccaaat tgacgatggg actactgaag aaggggtgag ggacgtggat    960
cgagagcaac ttgccaaggg ttatgagtac gggcggacat tggtccctat tagcgagacg   1020
gatgagaata tcaccaccct agagacattt gcggctatcg agcttcttgg gtttatacag   1080
agcgatcggt atgatcgata catgcacatg tcgacgacaa acatcatcat cgcgcagcgc   1140
gcgaatgaca aggcagcact cgctcttttcc tctttcatac atgcgctgtt cgagctggaa   1200
tcgtacgctg tcgcccgtat ggtgctaaag gagaacaaac cccctgtcat agtcgtgctt   1260
gcgccatcaa tcgaacccga ctacgagtgt ctcctcgaag cgcagttgcc attcgcagaa   1320
gacgtacgaa cgtaccgctt ccctccactc gacagagtca ttacagtgtc tggtaaagtg   1380
gtgacacagc atcgaaacct acccaacgac gatctgttga atgcgatgga caaatacgtg   1440
aaaagcatgg agcttaccga tatggacgag aacggtgacc cgacggaatc tctcccaata   1500
gacgactctt tctctccagt cctgcaccgg atcgactccg caatccgtca ccgtgccatt   1560
catcccaacg accctatccc gccccagcc tcagtcctaa cgaagttctc ccaccctccg    1620
gatgacctcg tcgagaagtc caagaaatac ctagacaagc tagtagcagt gtcggacgtc   1680
aagaaagtcc caccaaaaac caaaggcacc aaacggaccc gcgaaaccga aagccacta    1740
tccggtctcg acgtcgatgc ccttctccac caagagaagc gcacgaagat ctcacccaac   1800
aacgcaattc ccgagtttaa gcagacgctc tcgcaggcag agaacatcga gatcatcaag   1860
gatgcagtga agcagatgag cactatcatt gaagaccaaa tcaggcatag tcttggcgat   1920
gttaattatc atcgggtcac tgagggggcta ggtgtgatgc gggaggaact gatcgattat   1980
gaggaacctg ctctgtataa cgatttcttg aagcagctga aggagaagtt gttgaaagag   2040
gagctcggtg gggatcgacg ggagctgtgg tggctgctaa aaggagtaa gttggggttg   2100
attgaacaga gggagtcgga acactctgag gtgagagaag aggaagcgaa ggcgtttatg   2160
tctatggctg ctaagtga                                                 2178
```

<210> SEQ ID NO 6
<211> LENGTH: 725
<212> TYPE: PRT
<213> ORGANISM: Aspergillus niger

<400> SEQUENCE: 6

```
Met Ala Asp Lys Glu Ala Thr Val Tyr Ile Val Asp Cys Gly Lys Ser
1               5                   10                  15

Met Gly Glu Arg Arg His Gly Arg Glu Val Thr Asp Leu Asp Trp Ala
            20                  25                  30

Met Gln Tyr Val Trp Asp Arg Ile Thr Gly Thr Val Ala Thr Gly Arg
```

-continued

```
                35                  40                  45
Lys Met Ala Leu Ile Gly Val Leu Gly Leu Arg Thr Asp Val Cys Trp
 50                  55                  60
Ser Gly Leu Met Gln Glu Arg Pro Glu Thr Ala Asn Glu Leu Glu Asp
 65                  70                  75                  80
Asp Pro Asp Tyr Ser His Ile Ser Val Leu Ser Gly Ile Lys Gln Phe
                 85                  90                  95
Leu Met Pro Asp Ile Arg Gly Leu Ser Asp Arg Ile Lys Pro Ser Lys
            100                 105                 110
Thr Asn Lys Gly Asp Ala Ile Ser Ala Leu Val Leu Ala Ile Gln Met
        115                 120                 125
Ile Ile Thr Gln Cys Lys Lys Leu Lys Tyr Lys Arg Arg Ile Val Leu
    130                 135                 140
Val Thr Asn Gly Gln Gly Pro Met Asn Pro Asp Asn Leu Ser Glu Ile
145                 150                 155                 160
Thr Lys Lys Ile Lys Glu Asp Asn Ile Glu Leu Ile Ile Leu Gly Pro
                165                 170                 175
Asp Phe Asp Asp Pro Glu Tyr Gly Val Lys Glu Glu Asp Lys Asp Pro
            180                 185                 190
Arg Lys Ala Glu Asn Glu Thr Leu Leu Arg Ser Leu Ala Glu Asp Cys
        195                 200                 205
Glu Gly Ala Tyr Gly Thr Leu Glu Gln Ala Val Ala Glu Leu Glu Thr
    210                 215                 220
Pro Arg Val Lys Thr Thr Arg Ile Thr Ala Ser Phe Lys Gly His Leu
225                 230                 235                 240
Gln Leu Gly Asn Pro Ala Glu Tyr Asp Thr Ala Val Arg Ile Pro Val
                245                 250                 255
Glu Arg Tyr Tyr Arg Thr Tyr Val Ala Lys Ala Pro Ser Ala Ser Gln
            260                 265                 270
Phe Thr Val Arg Asn Glu Glu Met Gly Met Ala Ala Ala Ala Ala Ala
        275                 280                 285
Gly Ser Gln Glu Gly Ser Ser Leu Val Gly Val Arg Asn Asn Arg Ser
    290                 295                 300
Tyr Gln Ile Asp Asp Gly Thr Thr Glu Glu Gly Val Arg Asp Val Asp
305                 310                 315                 320
Arg Glu Gln Leu Ala Lys Gly Tyr Glu Tyr Gly Arg Thr Leu Val Pro
                325                 330                 335
Ile Ser Glu Thr Asp Glu Asn Ile Thr Thr Leu Glu Thr Phe Ala Ala
            340                 345                 350
Ile Glu Leu Leu Gly Phe Ile Gln Ser Asp Arg Tyr Asp Arg Tyr Met
        355                 360                 365
His Met Ser Thr Thr Asn Ile Ile Ala Gln Arg Ala Asn Asp Lys
    370                 375                 380
Ala Ala Leu Ala Leu Ser Ser Phe Ile His Ala Leu Phe Glu Leu Glu
385                 390                 395                 400
Ser Tyr Ala Val Ala Arg Met Val Leu Lys Glu Asn Lys Pro Pro Val
                405                 410                 415
Ile Val Val Leu Ala Pro Ser Ile Glu Pro Asp Tyr Glu Cys Leu Leu
            420                 425                 430
Glu Ala Gln Leu Pro Phe Ala Glu Asp Val Arg Thr Tyr Arg Phe Pro
        435                 440                 445
Pro Leu Asp Arg Val Ile Thr Val Ser Gly Lys Val Val Thr Gln His
    450                 455                 460
```

```
Arg Asn Leu Pro Asn Asp Asp Leu Leu Asn Ala Met Asp Lys Tyr Val
465                 470                 475                 480

Lys Ser Met Glu Leu Thr Asp Met Asp Glu Asn Gly Asp Pro Thr Glu
            485                 490                 495

Ser Leu Pro Ile Asp Asp Ser Phe Ser Pro Val Leu His Arg Ile Asp
        500                 505                 510

Ser Ala Ile Arg His Arg Ala Ile His Pro Asn Asp Pro Ile Pro Pro
    515                 520                 525

Pro Ala Ser Val Leu Thr Lys Phe Ser His Pro Pro Asp Asp Leu Val
530                 535                 540

Glu Lys Ser Lys Lys Tyr Leu Asp Lys Leu Val Ala Val Ser Asp Val
545                 550                 555                 560

Lys Lys Val Pro Pro Lys Thr Lys Gly Thr Lys Arg Thr Arg Glu Thr
                565                 570                 575

Glu Lys Pro Leu Ser Gly Leu Asp Val Asp Ala Leu Leu His Gln Glu
            580                 585                 590

Lys Arg Thr Lys Ile Ser Pro Asn Asn Ala Ile Pro Glu Phe Lys Gln
        595                 600                 605

Thr Leu Ser Gln Ala Glu Asn Ile Glu Ile Ile Lys Asp Ala Val Lys
    610                 615                 620

Gln Met Ser Thr Ile Ile Glu Asp Gln Ile Arg His Ser Leu Gly Asp
625                 630                 635                 640

Val Asn Tyr His Arg Val Thr Glu Gly Leu Gly Val Met Arg Glu Glu
                645                 650                 655

Leu Ile Asp Tyr Glu Glu Pro Ala Leu Tyr Asn Asp Phe Leu Lys Gln
            660                 665                 670

Leu Lys Glu Lys Leu Leu Lys Glu Glu Leu Gly Gly Asp Arg Arg Glu
        675                 680                 685

Leu Trp Trp Leu Leu Arg Arg Ser Lys Leu Gly Leu Ile Glu Gln Arg
    690                 695                 700

Glu Ser Glu His Ser Glu Val Arg Glu Glu Glu Ala Lys Ala Phe Met
705                 710                 715                 720

Ser Met Ala Ala Lys
            725

<210> SEQ ID NO 7
<211> LENGTH: 4501
<212> TYPE: DNA
<213> ORGANISM: Aspergillus niger

<400> SEQUENCE: 7
cagctcattc agagagctac ccgtagtaga acaggaatac tgggggtatt gtgagaacgc      60
gaccgcacga ccgcccttcc cattgccaaa gccatcttcc agcaattgtg tgtacatttg     120
ttccgtcagc gggttggcgt aacggaaggc aacgtacggc ttgtgaggcg cagtctccgg     180
gttgatcttg tccagcagct tgcacatttc cttgcattgg tattccgacc attttcttat     240
gggtgagcct ccgccgatgt ccgcatactg cttttgaatc ttgggtgtgc gtcgtttcga     300
aataagaggc ccgaggtaat gctggaactt gccaagagaa atcaaatcgc cgtcggcctt     360
gaatagaagt agaatgttag aaacgtagca accagaatga cagcttgcca tagtcggaga     420
cgtacaaaga gccggctgag gaaatcctct acttcgtctg tcgtcgaggg ccctcccatg     480
ttcaggaaga ccatggctgt agggccctta gagcctgttg catcctgggt aaccggaggc     540
actgttgttg ccagcccaca tctttgttct tgcttgtatc cgaacagggt gcgagaagcc     600
```

```
ggtcgcagca attgccgggg cagggtaaac gggcggcgga gagccatgac aggtaattgt    660
actgaattcg gttgacctag tcaatggagg taataagaaa agaccgttcg tatcgcgcaa    720
gcagatgaac tattcacgcc gcattaaata ttcaaaagat ggacgagtgg caagaacagg    780
tagtgggtgt atacaacagc gcaaggcctt ctggaagctg aaaagtccag aacggcttga    840
tgacggagca ccgagaccac gaccaactcc gactcccgac agccaatgac cggccagcta    900
gcgtcatcaa ttaccgggcg gacatcacat gatgttcgtg tctccccgcg tctttctgcc    960
caccggtttg atcgcgtccc tcgcgaccgg atccagtgac gatatagata gatctatctc   1020
cggctgcagg cagcagaggc caaacaggca gacacaacag ccccacttgt tcctggttac   1080
gattcaagtt gtcttaacct ttatacttcc ctctttcaat ttcgataata tcttgaatgc   1140
tttaaacgat tccacaacat tctactatgg cggacggcaa cccacatcgg gaagatgagg   1200
cggccgagga agaagaggag attgatgaga ctgtacgcaa atttacccat gaacttggac   1260
tggaactctg gaactgacaa taagatcaga gctacaaacc agtcaaagat gcggtcctct   1320
tcgcaatcga tgtcagcgat tccatgttga cgcctcgccc ctcagcagat cctaagaaac   1380
acacccaaga atcacccacc acggcagcgc tcaaatgcgc ctatcacttc atgcaacaac   1440
gaatcatatc aaatccacaa gacatgatgg gtgttttgct gttcgggacc caggcgtcca   1500
agttctttga agaagatgaa gacagtcggg gagacctgtc ctaccccaac tgctacctct   1560
tcactgatct ggatgttcct tcggctcatg aggtcaaagg acttcgagca ctggtagatg   1620
atgaaggaga ctcaagggag gttctatctc cagcgaaaga gcaggtctct atggcaaacg   1680
tcctattttg cgccaaccag atattcacat ccagagcgcc aaatttcctc tcccggcgtt   1740
tgttcatcat aaccgacaat gacaaccccc atggtgatga taaaaccctg cggtcagcgg   1800
cgactgtacg tgctaaggat cttacgatc ttggtgtcac aattgagctg tttccgatct   1860
cacgccctga gcatgagttc aagaacagca agttctatga cgtaagctat catactctat   1920
agcaaagtgg caggggtcga tactcactac agatacaaag gatattatct acaagtcatt   1980
gcccagcgat ccagaggcgc ctgcatatct acaatctgat tcaaaagcgg cgactgcgac   2040
cggggacggg atttcactcc tcaacacgct tctgtccagt attaattcga gaacggttcc   2100
gcgtcgcact cattttcga acatgccttt agaacttggc ccagacttca gaatttcggt   2160
atcgggctat atactcttac gaaggcaagc gcccgctaga aactccttca tctggctgaa   2220
cggcgagaag cctgtggtcg cgaaaggagt gacttcccac tccgcagatg atactggccg   2280
gactgtcgag aaatgggaga tcagaaaggc atataagttc ggtggcgacc aagtaacctt   2340
ttcgcctgat gagcagaagg cgcttaggga tttcggtgag ccagtaatcc gggttattgg   2400
gttcaagcct atcactgcgc ttccattctg ggcaaacgtc aagcacccat attttatcta   2460
tccatccgag gaagactatg taggctcctc gcgagtattt tccgcattgc atcagactct   2520
tttgcgttcc aagaagatgg cactcgtctg gttcattgca cgcaagggtg ctggccccgt   2580
tctcgccgct atgatcgcag gcgaagaaaa gcttgatgag aatggcgtac aaaaatatccc   2640 tcctggcatg tggattcttc ccctcccctt cgcagacgat atccggcaga accccgaaac   2700
aacgttgaat gtcgccccgg agtcattgat tgatcagatg cgcgtgatcg tccagcaact   2760
gcagctgccg aagggagtgt acgagcctct caaatacccc aatccatgta agtcacttct   2820
gtcttgcatt gctcgtatac gatgaacgag aagctgacag cccgtgatca gcccttcaat   2880
ggcattaccg catcctacaa gctctcgcat tagacgaaga tctccccgaa aaaccagaag   2940
```

-continued

```
acaaaaccat tccgaaatac cgccaaatcg acaaggtaaa tccaccacac ccaacacgag    3000 aaataacccct ccaggcgtcc aacttactga caattgcacc acagcgcgcc ggtgactacg   3060
tattatcctg ggccgacgaa ctcgaaaagc aatacgccaa acctcagca gcggcccctc    3120 gcccaaccag caccctcgtg aaacgaggat caaaagaccg agcaagcgaa accgaggact   3180
ccaagccatc gaaaaagatc aaggttgagg aagactctgg aagcctagag gaggaagtcc   3240
gcaggcatca aagaaggga acgctatcca aggtaagcca ccacaggctt tctacacgtc    3300
ctcgtgatgg caaatatgac atcgtattaa ccggcggttt tctagcttac ggtcgctatc   3360
ctcaaggact tcttgacttc caatggacgc tcaaatgccg gtaagaaggc ggatcttatt   3420
gagcgggtag aggagttctt ggagcagtga catggcggga ttgttggatt cgctagtgcg   3480
cttctgttgg tggatgtcgt tatgtggtgt cttatctcgg ttaggcgtt cgtgacctga    3540 ggacatgagc ttgtaattaa tgatggggttg gatgtcgcgg tattcgttct tcagcgaaac   3600
gtaatggaca cgtattttag gcgatgtaca gttataaaaa atcgaattcg ctgggctagc   3660
cggacatgtc aaaacgaaga gcattaggag agacatatca ggtccaagtg ctatctttca   3720
aaccagtcgc ttaagatcac cgaggcattt atctccagaa aattcaccgg ttcagcaggt   3780
gcgcgtatcc cgaattcaaa ttaatattgg aacgatcgta ataaccacc cagattcgcc    3840 gtaaacgata gtagtcaggc tttgccgccg acagaagggg acgagtatgt caactgagtc   3900
aacttgaacc gagcagtccc tgtaaacaac gccacgctgt tgtaatatc cctttagaaa    3960 cgtattgtcg ctggcaatta tccacaaaaa atgagtctaa acgggcgaaa aaagtcaccc   4020
gaatgggaga atatgtggaa agaagaaaga aagagagacc aaagcaagag agcgccgaaa   4080
ggaagctatc gtaatatata caagtagaag ccgtgggtat ttttataaaa agcagaaacg   4140
ttaacggtat gcgtacaatg atcaacattg tccataaact tgacagtagc agacttcttc   4200
gtcgggacag ctgagagtag caaagtgtta gtatttagga cgcattcagc aggtaggggg   4260
ggaggggtgc aaaggcaaca tactatattg attctttgcc gaatatgaca tgccagagaa   4320
attccatgac acggccacta ctggcgtcat ccttgtcggt atcgattatc cactggcgga   4380
tcttgatgta gtcctctcgt ggtcgtcggt ggacctgctc ccgggacacg gcgaattgcg   4440
cacagcacgc cgcgccaatc tgtttcggca tttgcaggaa cttctggtat ttagcttcgt   4500
c                                                                   4501
```

<210> SEQ ID NO 8
<211> LENGTH: 4702
<212> TYPE: DNA
<213> ORGANISM: Aspergillus niger

<400> SEQUENCE: 8

```
cactcaggat tcttatatct tatggggccc aagtatctct gcagtcaggc gaccaaggaa     60
cagcgttgca cgctgctgtg gtgggtggct ttcacggctc agtcaatttg cttctgacag    120
aaaatgcgga ggttgatgca tcatgtacac tcattgggac cccgttggcg gcagtcatgc   180
ctcgtaaatg gaagtcctgc tgtggtcgtt accatcgaag ctgtgctgag caattaattg   240
cttggggtgc agatattgat cgcattgatg aacgtctggg gactccaatg gacattgcat   300
acaaggcagg aaacaatgag ggtgtggagc tgttacttga gaatggagca ctggatccca   360
aatccacagc gtatccacta aattcggaca attgaccggg cacgaagtgc ttttctgttt   420
gagatatata tggagcactg aagaaaataa tcagagactt gccgtacttg aaaacttgga   480
gaaatgatcg gatcggtaaa tgtccaattt gccctgggtg tctgggctcg caagacccct   540
```

```
ttaaaataat atagacattc acgcactact cgcagcaaat cttaacaatt tgggcttgtc    600
taagctctgg gagatcacta atttattata gaaccttcaa atgtcgatta gtatgtgaga    660
gttatcttgt caattcagcc tgttagtaca ataaaaccca ctcatagcgg ctccgtcata    720
tataaaattg tgcactacac tcacttgcga tatatgatgc gcagcaccc atgttagtat     780 ctgcaatgtc acttcaattt cgccaacaaa ggaccctcca taagtagct actctgcaat    840 ttaaatcact agacttgtat cacaaatcat gtaaataaag caatacggag ataagctgc    900 ccactgcatg cccctcttag taagcaccca ctgcatgatg tcatgtgctt tcgcgtcccg    960
cccgctccca atcgggaaat atcacgcgtc tgcctactca gagtgcatct ttctgccttg   1020
agctcgtccc ttttatgtcg agccagctgc ggcatcgaat ggatctgatt ccatcgataa   1080
tctcagtcat tcatactgaa aatggccgat aaagaggcaa ctgtctacat cgtggactgc   1140
ggcaagtcca tgggggagcg gcgtcatggt cgcgaagtga cggatctcga ctgggcgatg   1200
caatatgttt gggatcgtat tacagggacg gtgagatcct tattcttgag aatcatatca   1260
tacatgaaag cttatgtttt ggataggtgg ccactggacg aaaaatggct ttgatcggtg   1320
ttcttgggct caggacagat ggtgagtgac tagcctcccg ggtacagttg gtagttgtag   1380
tttgctggtc ggggctaatg caggaacgtc cagaaaccgc taatgagttg gaggatgatc   1440
ctgattattc gcatatctcg gttttgtctg ggattaaaca gtatgattca ttttttgtctg  1500 ctgatcctct ggttattcgc tgatgaacta taggtttctt atgccggata tccggggttt   1560
gagcgaccga ataaagccta gcaagactaa taagggagat ggtgagttac tcttcttgta   1620
tggaattgga gtgattgggg ctgagccgat gaatatagct atctctgcac ttgtgctcgc   1680
gattcagatg attatcactc agtgcaagaa actgaagtac aagcgcagga ttgtcctggt   1740
tactaatggg cagggcccga tgaacccgga taatcttagt gaaataacga agaagattaa   1800
ggaggataac attgaactta ttattctgtt agtgtcaatt gatacactga gagaaccggg   1860
gtactaacat gctgcagggg accagacttt gatgatcctg aatatggggt gaaagaggaa   1920
gataaagatc cgcgaaaggt atttaacttc gttccatatg ctctagacta ataataacaa   1980
tggctacagg ccgaaaatga aacactcctg cgtagtcttg ccgaagactg cgaaggagcc   2040
tatgaacccc tagaacaagc tgttgcggag ctggaaactc ctcgtgtgaa aaccacaagg   2100
ataacagcaa gcttcaaggg ccatttgcaa ctaggaaacc ccgcagaata tgatactgca   2160
gttcggatcc ctgtggagcg ctactacagg acatacgttg caaaagctcc gtcggctagt   2220
cagttcacag tacgtaacga agaggagatg ggaatggccg cggccgcagc cggctcgcag   2280
gaaggtagtt cccttgtggg tgttcgaaac aacaggtcct accaaattga cgatgggact   2340
actgaagaag gggtgaggga cgtggatcga gagcaacttg ccaagggtta tgagtacggg   2400
cggacattgg tccctattag cgagacggat gagaatatca ccaccctaga gacatttgcg   2460
gctatcgagc ttcttgggtt tatacagagc gatcgggtga gttctacct ccaataactg     2520 ttattatgct gctaagtggg ttttgccatt agtatgatcg atacatgcac atgtcgacga   2580
caaacatcat catcgcgcag cgcgcgaatg acaaggcagc actcgctctt tcctcttttca  2640 tacatgcgct gttcgagctg gaatcgtacg ctgtcgcccg tatggtgcta aaggagaaca   2700
aaccccctgt catagtcgtg cttgcgccat caatcgaacc cgactacgag tgtctcctcg   2760
aagcgcagtt gccattcgca gaagacgtac gaacgtaccg cttccctcca ctcgacagag   2820
tcattacagt gtctggtaaa gtggtgacac agcatcgaaa cctacccaac gacgatctgt   2880
```

```
tgaatgcgat ggacaaatac gtgaaaagca tggagcttac cgatatggac gagaacgggt    2940
gagaagaatt ggaagtgatc tcaacttcac tgctgacttt gtacaaagtg acccgacgga    3000
atctctccca atagacgact ctttctctcc agtcctgcac cggatcgact ccgcaatccg    3060
tcaccgtgcc attcatccca acgaccctat cccgccccca gcctcagtcc taacgaagtt    3120
ctcccaccct ccggatgacc tcgtcgagaa gtccaagaaa tacctagaca agctagtagc    3180
agtgtcggac gtcaagaaag gtcagtccat ctcggccttg agcctcttag gcccccatca    3240
tactcacagt gatgaatcta gtcccaccaa aaaccaaagg caccaaacgg acccgcgaaa    3300
ccgagaagcc actatccggt ctcgacgtcg atgcccttct ccaccaagag aagcgcacga    3360
agatctcacc caacaacgca attcccgagt ttaagcagac gctctcgcag gcagagaaca    3420
tcgagatcat caaggatgca gtgaagcaga tgagcactat cattgaagac caaatcaggc    3480
atagtcttgg cgatgttaat tatcatcggg tcactgaggg gctaggtgtg atgcgggagg    3540
aactgatcga ttatgaggaa cctgctctgt ataacgattt cttgaagcag ctgaaggaga    3600
agttgttgaa agaggagctc ggtggggatc gacgggagct gtggtggctg ctaagaagga    3660
gtaagttggg gttgattgaa cagagggagt cggaacactc tgaggtgaga aagaggaag    3720
cgaaggcgtt tatgtctatg gctgctaagt gagcagaccg ttattgatcc ctattagtcc    3780
ccgattaagg actgggcaac agttcgataa tgacaaatga acaagctcca atgctgcatg    3840
actgtgctcg ctagagtaca atattcacga taaccctgcg ctaagtaaca aggcttatcc    3900
catgccaaat gtaacacaca taacatataa taccaaattc gatgaacagt acacgggata    3960
tcaatcatga ccatgagtag aaatagacat cgcaagcaac cattatatcc acacactcaa    4020
gaaattctcc caatcctctt cttcccaata tcaatcttcc cacccaacct atattcaagt    4080
cagcacaact ttaccatcaa aaagtaagaa caagatggga aaaagaaca tacctcgtag    4140
catcctcatc cgccaaattc aacaactcat tctgcacctg caactcattg ttaattgcaa    4200
tccccaactc cttctgccga ttgacaatcc tcatcaactc atccaccgcg acatcctgat    4260
cctccatcat ctgcttctgc aactgcacca ccccactatt atccaactcg cgcgtcctct    4320
ccgtctccct ccccaacact ctccccgacg accgaatcgc cttcttgccc cctgcgtcc    4380
ccatcaacgc ctccttatcc tgaatcgacg ccaccgcact atcaatccga ctcttcgccg    4440
ccatcgcatt caacagatcc tccagtccat ctttctcctt cctcgcgttg atgagtagat    4500
ccttccgtcg tcgcatctct ccttccccga gcgtgttgtt cccactaaca ctccatgccg    4560
tggcggtcgt agctgtattt ctgcgcccga gtttacttcc tggtcttgac cctgcattat    4620
tttcctcccc acctccagaa gaagagttac tcaaattcct caacccactc tccaaactcg    4680
caatcaatcc cccggccta ac                                              4702
```

<210> SEQ ID NO 9
<211> LENGTH: 3965
<212> TYPE: DNA
<213> ORGANISM: Aspergillus niger

<400> SEQUENCE: 9

```
gtttgacgcg tttgcagtgt agaagcttcc agctaccgta gattactgat acaaactcaa      60
tacactattt ctataacctt actgttcaat acagtacgat caaaatttcc ggaatattaa     120
tgttacggtt accttccata gtagactag cgcacttggc attagggttc gaaatacgat     180
caaagagtat tgggggggt gacagcagta atgactccaa ctgtaaatcg gcttctaggc     240
gcgctccatc taaatgttct ggctgtggtg tacaggggca taaaattacg cactacccga     300
```

```
atcgatagaa ctactcattt ttatatagaa gtcagaattc atggtgtttt gatcatttta    360
aatttttata tggcgggtgg tgggcaactc gcttgcgcgg gcaactcgct taccgattac    420
gttagggctg atatttacgt aaaaatcgtc aagggatgca agaccaaagt actaaaaccc    480
cggagtcaac agcatccaag cccaagtcct tcacggagaa accccagcgt ccacatcacg    540
agcgaaggac cacctctagg catcggacgc accatccaat tagaagcagc aaagcgaaac    600
agcccaagaa aaaggtcggc ccgtcggcct tttctgcaac gctgatcacg ggcagcgatc    660
caaccaacac cctccagagt gactagggc  ggaaatttat cgggattaat ttccactcaa    720
ccacaaatca cagtcgtccc cggtattgtc ctgcagaatg caatttaaac tcttctgcga    780
atcgcttgga ttccccgccc ctggccgtag agcttaaagt atgtcccttg tcgatgcgat    840
gtatcacaac atataaatac tagcaaggga tgccatgctt ggaggatagc aaccgacaac    900
atcacatcaa gctctccctt ctctgaacaa taaaccccac agaaggcatt tatgatggtc    960
gcgtggtggt ctctatttct gtacggcctt caggtcgcgg cacctgcttt ggctgcaacg   1020
cctgcggact ggcgatcgca atccatttat ttccttctca cggatcgatt tgcaaggacg   1080
gatgggtcga cgactgcgac ttgtaatact gcggatcagg tgtgttgtta cctactagct   1140
ttcagaaaga ggaatgtaaa ctgacttgat atagaaatac tgtggtggaa catggcaggg   1200
catcatcgac aagtaaatt  gccccttat  caaaaaaaaa agaaggaaaa gcagaagaaa   1260
aataaaataa aaagaactct agtcctaacc atcacatagt tggactatat ccagggaatg   1320
ggcttcacag ccatctggat cacccccgtt acagcccagc tgcccagac  caccgcatat   1380 ggagatgcct accatggcta ctggcagcag gatatgtaag tcgatttctt taaatatcta   1440
cctgtcatct tttacatcaa tatgaactaa cttgatggtt ttagatactc tctgaacgaa   1500
aactacggca ctgcagatga cttgaaggcg ctctcttcgg cccttcatga gaggggatg    1560 tatcttatgg tcgatgtggt tgctaaccat atggttcgtg gtcctttgca actgacttcg   1620
cggatatggt tcatttcagt actgacaatg agtaatatca gggctatgat ggagcgggta   1680
gctcagtcga ttacagtgtg tttaaaccgt tcagttccca agactacttc caccccgttct   1740 gtttcattca aaactatgaa gatcagactc aggttgagga ttgctggcta ggagataaca   1800
ctgtctcctt gcctgatctc gataccacca aggatgtggt caagaatgaa tggtacgact   1860
gggtgggatc attggtatcg aactactcca gtaagatatt tctccctcat tctacaactt   1920
ggctgatcga tgatacttac gaaatcagtt gacggcctcc gtatcgacac agtaaaacac   1980
gtccagaagg acttctggcc cgggtacaac aaagccgcag gcgtgtactg tatcggcgag   2040
gtgctcgacg gtgatccggc ctacacttgt ccctaccaga acgtcatgga cggcgtactg   2100
aactatccca tgtatggttc ctccaaccat gagccttctt gcaagtctca tctcctaacg   2160
aaacggctaa aaccagttac tatccactcc tcaacgcctt caagtcaacc tccggcagca   2220
tggacgacct ctacaacatg atcaacaccg tcaaatccga ctgtccagac tcaacactcc   2280
tgggcacatt cgtcgagaac cacgacaacc cacggttcgc ttcgtaagtc ttccctttta   2340
ttttccgttc ccaatttcca cacagaaccc cacctaacaa gagcaaagtt acaccaacga   2400
catagccctc gccaagaacg tcgcagcatt catcatcctc aacgacggaa tccccatcat   2460
ctacgccggc caagaacagc actacgccgg cggaaacgac cccgcgaacc gcgaagcaac   2520
ctggctctcg ggctacccga ccgacagcga gctgtacaag ttaattgcct ccgcgaacgc   2580
aatccggaac tatgccatta gcaaagatac aggattcgtg acctacaagg taagcacaac   2640
```

| | | |
|---|---|---|
| ctctaagcat accctaatgg cctatcttca gagtatctga cacaagagac taatcactgg | | 2700 |
| caatacagaa ctggcccatc tacaaagacg acacaacgat cgccatgcgc aagggcacag | | 2760 |
| atgggtcgca gatcgtgact atcttgtcca acaagggtgc ttcgggtgat cgtataccc | | 2820 |
| tctccttgag tggtgcgggt tacacagccg ccagcaatt gacggaggtc attggctgca | | 2880 |
| cgaccgtgac ggttggttcg gatggaaatg tgcctgttcc tatggcaggt gggctaccta | | 2940 |
| gggtattgta tccgactgag aagttggcag gtagcaagat ctgtagtagc tcgtgaaggg | | 3000 |
| tggagagtat atgatggtac tgctattcaa tctggcattg acagtgagt ttgagtttga | | 3060 |
| tgtacataac caaggttgtg tctgtataat atatacatgt aagatacatg agcttcggtg | | 3120 |
| atataataca gaagtaccat acagtaccgc gttatgaaaa cacattaatc cggatccttt | | 3180 |
| cctataatag actagcgtgc ttggcattag ggttcgaaaa acaatcgaag agtataaggg | | 3240 |
| gatgacagca gtaacgactc caactgtagc ccacatcttg agttcggcaa ctactgttgg | | 3300 |
| cacgtgaccc tgtgccttgt ggtagctcct taactttgtc atcattcgaa gaattttcgt | | 3360 |
| cccttcccag gtaccatcca aaagacaagc atccgtcgct tcactctgag atcagatgag | | 3420 |
| agtaatattg ttgactgcgt ttgtgatgcg ggtgatgtcc tctgcgatcg gccgcaagct | | 3480 |
| gtttagtttg ccccggatct tctgtgccga cggttgctcc ccgaattttc ttagctagtg | | 3540 |
| taatcacgct attcagaaag gcttccaaga attaggccgg tagttcggcg cgtttggtgt | | 3600 |
| cgtcaagctc cagcagtgct ggggcctcgg ctatgatatg gttagaatgc tcggggtggg | | 3660 |
| tcacggcagg acaccgcaca ctgcaacgtc taccacattt gagcgttatt ggcagacttg | | 3720 |
| cggcgagata acgaccgcta gcttgtatca accaaatcca actgaaatta ttgctttgcc | | 3780 |
| atcccaacag tggatttcgg aggagggagg ggggaagata tacgatgaac ggaagactgg | | 3840 |
| acaagatacg ttcataaaag cagtactact tgtttcaaac tgtgtacaca ccagggctct | | 3900 |
| cgcttcagcg gagagtgtcg aaagattcag taaaacatcg ccagggtga tggaaagggg | | 3960 |
| ttaag | | 3965 |

<210> SEQ ID NO 10
<211> LENGTH: 1497
<212> TYPE: DNA
<213> ORGANISM: Aspergillus niger
<220> FEATURE:
<221> NAME/KEY: CDS
<222> LOCATION: (1)..(1497)

<400> SEQUENCE: 10

| | |
|---|---|
| atg gtc gcg tgg tgg tct cta ttt ctg tac ggc ctt cag gtc gcg gca<br>Met Val Ala Trp Trp Ser Leu Phe Leu Tyr Gly Leu Gln Val Ala Ala<br>1               5                   10                  15 | 48 |
| cct gct ttg gct gca acg cct gcg gac tgg cga tcg caa tcc att tat<br>Pro Ala Leu Ala Ala Thr Pro Ala Asp Trp Arg Ser Gln Ser Ile Tyr<br>            20                  25                  30 | 96 |
| ttc ctt ctc acg gat cga ttt gca agg acg gat ggg tcg acg act gcg<br>Phe Leu Leu Thr Asp Arg Phe Ala Arg Thr Asp Gly Ser Thr Thr Ala<br>        35                  40                  45 | 144 |
| act tgt aat act gcg gat cag aaa tac tgt ggt gga aca tgg cag ggc<br>Thr Cys Asn Thr Ala Asp Gln Lys Tyr Cys Gly Gly Thr Trp Gln Gly<br>    50                  55                  60 | 192 |
| atc atc gac aag ttg gac tat atc cag gga atg ggc ttc aca gcc atc<br>Ile Ile Asp Lys Leu Asp Tyr Ile Gln Gly Met Gly Phe Thr Ala Ile<br>65                  70                  75                  80 | 240 |
| tgg atc acc ccc gtt aca gcc cag ctg ccc cag acc acg gca tat gga<br>Trp Ile Thr Pro Val Thr Ala Gln Leu Pro Gln Thr Thr Ala Tyr Gly | 288 |

```
                    85                  90                  95
gat gcc tac cat ggc tac tgg cag cag gat ata tac tct ctg aac gaa    336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat    384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc    432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc    480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa    528
Ser Ser Gln Asp Tyr Phe His Pro Phe Cys Phe Ile Gln Asn Tyr Glu
                165                 170                 175 gat cag act cag gtt gag gat tgc tgg cta gga gat aac act gtc tcc    576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac    624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt    672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac    720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg    768
Lys Ala Ala Gly Val Tyr Cys Ile Gly Glu Val Leu Asp Gly Asp Pro
                245                 250                 255 gcc tac act tgt ccc tac cag aac gtc atg gac ggc gta ctg aac tat    816
Ala Tyr Thr Cys Pro Tyr Gln Asn Val Met Asp Gly Val Leu Asn Tyr
            260                 265                 270 ccc att tac tat cca ctc ctc aac gcc ttc aag tca acc tcc ggc agc    864
Pro Ile Tyr Tyr Pro Leu Leu Asn Ala Phe Lys Ser Thr Ser Gly Ser
        275                 280                 285 atg gac gac ctc tac aac atg atc aac acc gtc aaa tcc gac tgt cca    912
Met Asp Asp Leu Tyr Asn Met Ile Asn Thr Val Lys Ser Asp Cys Pro
    290                 295                 300 gac tca aca ctc ctg ggc aca ttc gtc gag aac cac gac aac cca cgg    960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca    1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa    1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg    1104
Gln His Tyr Ala Gly Gly Asn Asp Pro Ala Asn Arg Glu Ala Thr Trp
        355                 360                 365 ctc tcg ggc tac ccg acc gac agc gag ctg tac aag tta att gcc tcc    1152
Leu Ser Gly Tyr Pro Thr Asp Ser Glu Leu Tyr Lys Leu Ile Ala Ser
    370                 375                 380 gcg aac gca atc cgg aac tat gcc att agc aaa gat aca gga ttc gtg    1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg    1248
```

```
        Thr Tyr Lys Asn Trp Pro Ile Tyr Lys Asp Asp Thr Thr Ile Ala Met
                        405                 410                 415 cgc aag ggc aca gat ggg tcg cag atc gtg act atc ttg tcc aac aag         1296
Arg Lys Gly Thr Asp Gly Ser Gln Ile Val Thr Ile Leu Ser Asn Lys
                420                 425                 430 ggt gct tcg ggt gat tcg tat acc ctc tcc ttg agt ggt gcg ggt tac         1344
Gly Ala Ser Gly Asp Ser Tyr Thr Leu Ser Leu Ser Gly Ala Gly Tyr
            435                 440                 445 aca gcc ggc cag caa ttg acg gag gtc att ggc tgc acg acc gtg acg         1392
Thr Ala Gly Gln Gln Leu Thr Glu Val Ile Gly Cys Thr Thr Val Thr
        450                 455                 460 gtt ggt tcg gat gga aat gtg cct gtt cct atg gca ggt ggg cta cct         1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt         1488
Arg Val Leu Tyr Pro Thr Glu Lys Leu Ala Gly Ser Lys Ile Cys Ser
                485                 490                 495 agc tcg tga                                                             1497
Ser Ser <210> SEQ ID NO 11
<211> LENGTH: 498
<212> TYPE: PRT
<213> ORGANISM: Aspergillus niger

<400> SEQUENCE: 11

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
                20                  25                  30

Phe Leu Leu Thr Asp Arg Phe Ala Arg Thr Asp Gly Ser Thr Thr Ala
            35                  40                  45

Thr Cys Asn Thr Ala Asp Gln Lys Tyr Cys Gly Gly Thr Trp Gln Gly
        50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
                100                 105                 110

Asn Tyr Gly Thr Ala Asp Asp Leu Lys Ala Leu Ser Ser Ala Leu His
            115                 120                 125

Glu Arg Gly Met Tyr Leu Met Val Asp Val Val Ala Asn His Met Gly
        130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240
```

```
Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
    290                 295                 300

Asp Ser Thr Leu Leu Gly Thr Phe Val Glu His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
        355                 360                 365

Leu Ser Gly Tyr Pro Thr Asp Ser Glu Leu Tyr Lys Leu Ile Ala Ser
    370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
        435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 12
<211> LENGTH: 3697
<212> TYPE: DNA
<213> ORGANISM: Aspergillus niger

<400> SEQUENCE: 12
cttgtaatac gcttcctcaa tgtcgtattt cgaaagaaa cgggctttct ttatccaatc      60
cctgtggtaa gattgatcgt caggagatta tctgcaggaa acatcatggt ggggtaacca    120
aggttgtgtc tgtataatat atacatgtaa gatacatgag cttcggtgat ataatacaga    180
agtaccatac agtaccgcgt tatgaaaaca cattaatccg gatcctttcc tataatagac    240
tagcgtgctt ggcattaggg ttcgaaaaac aatcgaagag tataagggga tgacagcagt    300
aacgactcca actgtacgcc tccgggtagt agaccgagca gccgagccag ctcagcgcct    360
aaaacgcctt atacaattaa gcagttaaag aagttagaat ctacgcttaa aaagctactt    420
aaaaatcgat ctcgcagtcc cgattcgcct atcaaaacca gtttaaatca actgattaaa    480
ggtgccgaac gagctataaa tgatataaca atattaaagc attaattaga gcaatatcag    540
gccgcgcacg aaaggcaact taaaagcga agcgctcta ctaaacagat tactttttgaa    600 aaaggcacat cagtatttaa agcccgaatc cttattaagc gccgaaatca ggcagataaa    660
```

```
gccatacagg cagatagacc tctacctatt aaatcggctt ctaggcgcgc tccatctaaa    720
tgttctggct gtggtgtaca ggggcataaa attacgcact acccgaatcg atagaactac    780 tcattttat atagaagtca gaattcatgg tgttttgatc attttaaatt tttatatggc     840
gggtggtggg caactcgctt gcgcgggcaa ctcgcttacc gattacgtta gggctgatat    900
ttacgtaaaa atcgtcaagg gatgcaagac caaagtagta aaaccccgga gtcaacagca    960
tccaagccca agtccttcac ggagaaaccc cagcgtccac atcacgagcg aaggaccacc   1020
tctaggcatc ggacgcacca tccaattaga agcagcaaag cgaaacagcc caagaaaaag   1080
gtcggcccgt cggccttttc tgcaacgctg atcacgggca gcgatccaac caacaccctc   1140
cagagtgact aggggcggaa atttaaaggg attaatttcc actcaaccac aaatcacagt   1200 cgtcccggt attgtcctgc agaatgcaat ttaaactctt ctgcgaatcg cttggattcc    1260
ccgcccctgg ccgtagagct taaagtatgt cccttgtcga tgcgatgtat cacaacatat   1320
aaatactagc aagggatgcc atgcttggag gatagcaacc gacaacatca catcaagctc   1380
tcccttctct gaacaataaa ccccacagaa ggcatttatg atggtcgcgt ggtggtctct   1440
atttctgtac ggccttcagg tcgcggcacc tgctttggct gcaacgcctg cggactggcg   1500
atcgcaatcc atttatttcc ttctcacgga tcgatttgca aggacggatg ggtcgacgac   1560
tgcgacttgt aatactgcgg atcaggtgtg ttgttaccta ctagctttca gaaagaggaa   1620
tgtaaactga cttgatatag aaatactgtg gtggaacatg gcagggcatc atcgacaagg   1680
taaattgccc ctttatcaaa aaaaagaag gaaaagcaga agaaaaataa aataaaaga    1740 actctagtcc taaccatcac atagttggac tatatccagg gaatgggctt cacagccatc   1800
tggatcaccc ccgttacagc ccagctgccc cagaccaccg catatggaga tgcctaccat   1860
ggctactggc agcaggatat gtaagtcgat ttctttaaat atctacctgt catcttttac   1920
atcaatatga actaacttga tggttttaga tactctctga acgaaaacta cggcactgca   1980
gatgacttga aggcgctctc ttcggccctt catgagaggg ggatgtatct tatggtcgat   2040
gtggttgcta accatatggt tcgtggtcct ttgcaactga cttcgcggat atggttcatt   2100
tcagtactga caatgagtaa tatcagggct atgatggagc gggtagctca gtcgattaca   2160
gtgtgtttaa accgttcagt tcccaagact acttccaccc gttctgtttc attcaaaact   2220
atgaagatca gactcaggtt gaggattgct ggctaggaga taaacactgtc tccttgcctg   2280 atctcgatac caccaaggat gtggtcaaga atgaatggta cgactgggtg ggatcattgg   2340
tatcgaacta ctccagtaag atatttctcc ctcattctac aacttggctg atcgatgata   2400
cttacgaaat cagttgacgg cctccgtatc gacacagtaa aacacgtcca gaaggacttc   2460
tggcccgggt acaacaaagc cgcaggcgtg tactgtatcg gcgaggtgct cgacggtgat   2520
ccggcctaca cttgtcccta ccagaacgtc atggacggcg tactgaacta tcccatgtat   2580
ggttcctcca accatgagcc ttcttgcaag tctcatctcc taacgaaacg gctaaaacca   2640
gttactatcc actcctcaac gccttcaagt caacctccgg cagcatggac gacctctaca   2700
acatgatcaa caccgtcaaa tccgactgtc cagactcaac actcctgggc acattcgtcg   2760
agaaccacga caacccacgg ttcgcttcgt aagtcttccc ttttatttc cgttcccaat    2820 ttccacacag aaccccacct aacaagagca aagttacacc aacgacatag ccctcgccaa   2880
gaacgtcgca gcattcatca tcctcaacga cggaatcccc atcatctacg ccggccaaga   2940
acagcactac gccggcggaa acgaccccgc gaaccgcgaa gcaacctggc tctcgggcta   3000
```

```
cccgaccgac agcgagctgt acaagttaat tgcctccgcg aacgcaatcc ggaactatgc    3060
cattagcaaa gatacaggat tcgtgaccta caaggtaagc acaacctcta agcataccct    3120
aatggcctat cttcagagta tctgacacaa gagactaatc actggcaata cagaactggc    3180
ccatctacaa agacgacaca acgatcgcca tgcgcaaggg cacagatggg tcgcagatcg    3240
tgactatctt gtccaacaag ggtgcttcgg gtgattcgta taccctctcc ttgagtggtg    3300
cgggttacac agccggccag caattgacgg aggtcattgg ctgcacgacc gtgacggttg    3360
gttcggatgg aaatgtgcct gttcctatgg caggtgggct acctagggta ttgtatccga    3420
ctgagaagtt ggcaggtagc aagatctgta gtagctcgtg aagggtggag agtatatgat    3480
ggtactgcta ttcaatctgg cattggacag tgagtttgag tttgatgtac agttggagtc    3540
gttactgctg tcatccccct tatactcttcg attgttttc gaaccctaat gccaagcacg     3600
ctagtctatt ataggaaagg atccggatta atgtgttttc ataacgcggt actgtatggt    3660
acttctgtat tatatcaccg aagctcatgt atcttac                             3697

<210> SEQ ID NO 13
<211> LENGTH: 1497
<212> TYPE: DNA
<213> ORGANISM: Aspergillus niger
<220> FEATURE:
<221> NAME/KEY: CDS
<222> LOCATION: (1)..(1497)

<400> SEQUENCE: 13 atg gtc gcg tgg tgg tct cta ttt ctg tac ggc ctt cag gtc gcg gca         48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat         96
Pro Ala Leu Ala Ala Thr Pro Ala Asp Trp Arg Ser Gln Ser Ile Tyr
            20                  25                  30 ttc ctc ctc acg gat cga ttt gca agg acg gat ggg tcg acg act gcg        144
Phe Leu Leu Thr Asp Arg Phe Ala Arg Thr Asp Gly Ser Thr Thr Ala
        35                  40                  45 act tgt aat act gcg gat cag aaa tac tgt ggt gga aca tgg cag ggc        192
Thr Cys Asn Thr Ala Asp Gln Lys Tyr Cys Gly Gly Thr Trp Gln Gly
    50                  55                  60 atc atc gac aag ttg gac tat atc cag gga atg ggc ttc aca gcc atc        240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga        288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa        336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat        384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc        432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc        480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa        528
Ser Ser Gln Asp Tyr Phe His Pro Phe Cys Phe Ile Gln Asn Tyr Glu
                165                 170                 175
```

```
gat cag act cag gtt gag gat tgc tgg cta gga gat aac act gtc tcc      576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac      624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt      672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac      720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg      768
Lys Ala Ala Gly Val Tyr Cys Ile Gly Glu Val Leu Asp Gly Asp Pro
                245                 250                 255 gcc tac act tgt ccc tac cag aac gtc atg gac ggc gta ctg aac tat      816
Ala Tyr Thr Cys Pro Tyr Gln Asn Val Met Asp Gly Val Leu Asn Tyr
            260                 265                 270 ccc att tac tat cca ctc ctc aac gcc ttc aag tca acc tcc ggc agc      864
Pro Ile Tyr Tyr Pro Leu Leu Asn Ala Phe Lys Ser Thr Ser Gly Ser
        275                 280                 285 atg gac gac ctc tac aac atg atc aac acc gtc aaa tcc gac tgt cca      912
Met Asp Asp Leu Tyr Asn Met Ile Asn Thr Val Lys Ser Asp Cys Pro
    290                 295                 300 gac tca aca ctc ctg ggc aca ttc gtc gag aac cac gac aac cca cgg      960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca     1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa     1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg     1104
Gln His Tyr Ala Gly Gly Asn Asp Pro Ala Asn Arg Glu Ala Thr Trp
        355                 360                 365 ctc tcg ggc tac ccg acc gac agc gag ctg tac aag tta att gcc tcc     1152
Leu Ser Gly Tyr Pro Thr Asp Ser Glu Leu Tyr Lys Leu Ile Ala Ser
    370                 375                 380 gcg aac gca atc cgg aac tat gcc att agc aaa gat aca gga ttc gtg     1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg     1248
Thr Tyr Lys Asn Trp Pro Ile Tyr Lys Asp Asp Thr Thr Ile Ala Met
                405                 410                 415 cgc aag ggc aca gat ggg tcg cag atc gtg act atc ttg tcc aac aag     1296
Arg Lys Gly Thr Asp Gly Ser Gln Ile Val Thr Ile Leu Ser Asn Lys
            420                 425                 430 ggt gct tcg ggt gat tcg tat acc ctc tcc ttg agt ggt gcg ggt tac     1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg     1392
Thr Ala Gly Gln Gln Leu Thr Glu Val Ile Gly Cys Thr Thr Val Thr
    450                 455                 460 gtt ggt tcg gat gga aat gtg cct gtt cct atg gca ggt ggg cta cct     1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt     1488
Arg Val Leu Tyr Pro Thr Glu Lys Leu Ala Gly Ser Lys Ile Cys Ser
                485                 490                 495
```

```
agc tcg tga                                                          1497
Ser Ser
```

<210> SEQ ID NO 14
<211> LENGTH: 498
<212> TYPE: PRT
<213> ORGANISM: Aspergillus niger

<400> SEQUENCE: 14

```
Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
    290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
```

```
                 355                 360                 365
Leu Ser Gly Tyr Pro Thr Asp Ser Glu Leu Tyr Lys Leu Ile Ala Ser
370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
        435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 15
<211> LENGTH: 3570
<212> TYPE: DNA
<213> ORGANISM: Aspergillus niger

<400> SEQUENCE: 15
ggaaccagta cggcagctga tagtatccga aagctgcaaa ttgcttcatc gaggctggca        60
ttcgatagaa gaaagaatta tagacaacta gtcttgcaat atgacaattc tctttgatta       120
ataaatgaaa gcacgcatgt atcagcctaa tagccgagtg gcgggcatct ctggcggcct       180
cccgagcagc gtggaatgcg tccaagatcc cgtccgcggg tcgtccttcg gtcggaatga       240
tgactggagc agcagacgat gtcctgagct gaatgcatgt gatattcaca ttccagggag       300
aattgtcggc tatttagaac cctctcggct aaaagcccct attagactat gggtgcgctc       360
aagccactag ccaggatatc ccgctgaacg ctccatcacc ttgcagctga agtgcaacat       420
gggacgggct ttaactttc gtagatataa gtttaattta tcctctccac acccataggg       480
tcgtatggtg tcaaccggtg tagtctgcag gatttcatct cgcttcgcca agcgaggcgc       540
cctaacgggc agcctgcagc ttaccctgtt aaccccggct caccacccc cgagcaatcc       600
gtcgcgtcct ccacgagtca taacaaggtt cgggcgttgt ttcttacccc cactatcagg       660
cgtattcagt taacagtcag tagtcccgtg tcggagattt gttgttctgc aacaattaaa       720
ggggaccagg gttaaatcct ggcccccgaa ctgatcggag tttcggccaa tgagagatgt       780
tgtatacccc cgttcctggc agatggatta attgccggct ccatttggca tccatcaagc       840
atcatacggg attagaaggg tagttcgtgg gttgatctgc cgtgcaaggt gctcaaggct       900
ctggagtcat gctgaacgca atatttaag aatcgtcgtc agggacagcg ttctctggat       960
agtcaagctg tgcttgggac gctgttctgt cgctttgtca aaacataatt cgcagcgatg      1020
agattatcga cttcgagtct cttccttccc gtgtctctgc tggggaagct ggccctcggg      1080
ctgtcggctg cagaatggcg cactcagtcg atttacttcc tattgacgga tcggttcggt      1140
aggacggaca attcgacgac agctacatgc gatacgggtg accaagtacg ttggtattgc      1200
aggacttcca tcattcatct actgacttga atagatctat tgtggtggca gttggcaagg      1260
aatcatcaac catgtttgtg atcacttcat actatccgct gtgcgcgtgt ctgactttat      1320
```

```
ttgctgcagc tggattatat ccagggcatg ggattcacgg ccatctggat ctcgcctatc     1380
actgaacagc tgccccagga tactgctgat ggtgaagctt accatggata ttggcagcag     1440
aagatgtatg cgctcctcct tcccatatcg taggcttact ctcaggcggc gactgacttg     1500
acagatacga cgtgaactcc aacttcggca ctgcagatga cctcaagtcc ctctcagatg     1560
cgcttcatgc ccgcggaatg tacctcatgg tggacgtcgt ccctaaccac atggtaagtg     1620
ctgcttcagc atccttatca gtgaactcca agtgccaacg ctaactgtac cagggctacg     1680
ccggcaacgg caacgatgta gactacagcg tcttcgaccc cttcgattcc tcctcctact     1740
tccacccata ctgcctgatc acagattggg acaacttgac catggtccaa gattgttggg     1800
agggtgacac catcgtatct ctgccagacc taaacaccac cgaaactgcc gtgagaacaa     1860
tctggtatga ctgggtagcc gacctggtat ccaattattc aggtgcgaat tccaacccaa     1920
tttaaaataa ccatatacta agtgaaatca ccagtcgacg gactccgcat cgacagtgtc     1980
ctcgaagtcg aaccagactt cttcccgggc taccaggaag cagcaggtgt ctactgcgtc     2040
ggcgaagtcg acaacggcaa ccctgccctc gactgcccat accagaaggt cctggacggc     2100
gtcctcaact atccgatgta catcccccta tacattgttc attagatctt cgctaactcc     2160
aaccagctac tggcaactcc tctacgcctt cgaatcctcc agcggcagca tcagcaacct     2220
ctacaacatg atcaaatccg tcgcaagcga ctgctccgat ccgacactac tcggcaactt     2280
catcgaaaac cacgacaatc cccgtttcgc ctcgtatgtc ccaccccctc ccctccctac     2340
aatcacactc actaatacat ctaacagcta cacctccgac tactcgcaag ccaaaaacgt     2400
cctcagctac atcttcctct ccgacggcat ccccatcgtc tacgccggcg aagaacagca     2460
ctactccggc ggcaaggtgc cctacaaccg cgaagcgacc tggctttcag gctacgacac     2520
ctccgcagag ctgtacacct ggatagccac cacgaacgcg atccgcaaac tagccatctc     2580
agctgactcg gcctacatta cctacgcggt tcgtccttcc ctcccaccct ttaccccca     2640 ccctacaaac atcccacata ctaacaacat ttcaataatg aaatagaatg atgcattcta     2700
cactgacagc aacaccatcg caatgcgcaa aggcacctca gggagccaag tcatcaccgt     2760
cctctccaac aaaggctcct caggaagcag ctacaccctg accctcagcg gaagcggcta     2820
cacatccggc acgaagctga tcgaagcgta cacatgcaca tccgtgaccg tggactcgag     2880
cggcgatatt cccgtgccga tggcgtcggg attaccgaga gttcttctgc ccgcgtccgt     2940
cgtcgatagc tcttcgctct gtggcgggag cggaagatta tacgtcgagt aatccggagt     3000
ggtcggttac tgtgacgttg ccggtgggga ccactttcga gtataagttt attaaggtgg     3060
agtcggatgg gactgttact tgggaaagtg attcgaatcg ggagtatacg gtgccggagt     3120
gtgggagtgg ggagacggtg gttgatactt ggaggtagat gatctgagat ttctaagtgt     3180
gatgagggtg gttttggtgt atgtagtttg gcctttggta gtgttgggtt gggttgggtt     3240
aataattatg ttattgtttt tggtgcttgt gaccatggat ttgaagtgaa aatttgtagg     3300
ggctacggaa gtgtattgtg gacatgtgag taaattcatc tgggtatgta caaagtgggt     3360
tagccagtgg gcttgaagaa agtctcctg ggtctctggt ttgagtaccc atgttaagat     3420
caagcataaa aacatgaaat attgggaaaa caaagggtat ttaacaactc gtgagcatta     3480
gctcctgggt agaatgcaat cataacagaa agtacagcca gcgctgtgtc ataaagaagt     3540
ccagttggga aacgaaagac tagaatcaaa                                     3570
```

<210> SEQ ID NO 16

```
<211> LENGTH: 1518
<212> TYPE: DNA
<213> ORGANISM: Aspergillus niger
<220> FEATURE:
<221> NAME/KEY: CDS
<222> LOCATION: (1)..(1518)

<400> SEQUENCE: 16 atg aga tta tcg act tcg agt ctc ttc ctt tcc gtg tct ctg ctg ggg      48
Met Arg Leu Ser Thr Ser Ser Leu Phe Leu Ser Val Ser Leu Leu Gly
1               5                   10                  15 aag ctg gcc ctc ggg ctg tcg gct gca gaa tgg cgc act cag tcg att      96
Lys Leu Ala Leu Gly Leu Ser Ala Ala Glu Trp Arg Thr Gln Ser Ile
            20                  25                  30 tac ttc cta ttg acg gat cgg ttc ggt agg acg gac aat tcg acg aca     144
Tyr Phe Leu Leu Thr Asp Arg Phe Gly Arg Thr Asp Asn Ser Thr Thr
        35                  40                  45 gct aca tgc gat acg ggt gac caa atc tat tgt ggt ggc agt tgg caa     192
Ala Thr Cys Asp Thr Gly Asp Gln Ile Tyr Cys Gly Gly Ser Trp Gln
    50                  55                  60 gga atc atc aac cat ctg gat tat atc cag ggc atg gga ttc acg gcc     240
Gly Ile Ile Asn His Leu Asp Tyr Ile Gln Gly Met Gly Phe Thr Ala
65                  70                  75                  80 atc tgg atc tcg cct atc act gaa cag ctg ccc cag gat act gct gat     288
Ile Trp Ile Ser Pro Ile Thr Glu Gln Leu Pro Gln Asp Thr Ala Asp
                85                  90                  95 ggt gaa gct tac cat gga tat tgg cag cag aag ata tac gac gtg aac     336
Gly Glu Ala Tyr His Gly Tyr Trp Gln Gln Lys Ile Tyr Asp Val Asn
            100                 105                 110 tcc aac ttc ggc act gca gat gac ctc aag tcc ctc tca gat gcg ctt     384
Ser Asn Phe Gly Thr Ala Asp Asp Leu Lys Ser Leu Ser Asp Ala Leu
        115                 120                 125 cat gcc cgc gga atg tac ctc atg gtg gac gtc gtc cct aac cac atg     432
His Ala Arg Gly Met Tyr Leu Met Val Asp Val Val Pro Asn His Met
    130                 135                 140 ggc tac gcc ggc aac ggc aac gat gta gac tac agc gtc ttc gac ccc     480
Gly Tyr Ala Gly Asn Gly Asn Asp Val Asp Tyr Ser Val Phe Asp Pro
145                 150                 155                 160 ttc gat tcc tcc tcc tac ttc cac cca tac tgc ctg atc aca gat tgg     528
Phe Asp Ser Ser Ser Tyr Phe His Pro Tyr Cys Leu Ile Thr Asp Trp
                165                 170                 175 gac aac ttg acc atg gtc caa gat tgt tgg gag ggt gac acc atc gta     576
Asp Asn Leu Thr Met Val Gln Asp Cys Trp Glu Gly Asp Thr Ile Val
            180                 185                 190 tct ctg cca gac cta aac acc acc gaa act gcc gtg aga aca atc tgg     624
Ser Leu Pro Asp Leu Asn Thr Thr Glu Thr Ala Val Arg Thr Ile Trp
        195                 200                 205 tat gac tgg gta gcc gac ctg gta tcc aat tat tca gtc gac gga ctc     672
Tyr Asp Trp Val Ala Asp Leu Val Ser Asn Tyr Ser Val Asp Gly Leu
    210                 215                 220 cgc atc gac agt gtc ctc gaa gtc gaa cca gac ttc ttc ccg ggc tac     720
Arg Ile Asp Ser Val Leu Glu Val Glu Pro Asp Phe Phe Pro Gly Tyr
225                 230                 235                 240 cag gaa gca gca ggt gtc tac tgc gtc ggc gaa gtc gac aac ggc aac     768
Gln Glu Ala Ala Gly Val Tyr Cys Val Gly Glu Val Asp Asn Gly Asn
                245                 250                 255 cct gcc ctc gac tgc cca tac cag aag gtc ctg gac ggc gtc ctc aac     816
Pro Ala Leu Asp Cys Pro Tyr Gln Lys Val Leu Asp Gly Val Leu Asn
            260                 265                 270 tat ccg atc tac tgg caa ctc ctc tac gcc ttc gaa tcc tcc agc ggc     864
Tyr Pro Ile Tyr Trp Gln Leu Leu Tyr Ala Phe Glu Ser Ser Ser Gly
        275                 280                 285
```

```
                       275                 280                 285
agc atc agc aac ctc tac aac atg atc aaa tcc gtc gca agc gac tgc      912
Ser Ile Ser Asn Leu Tyr Asn Met Ile Lys Ser Val Ala Ser Asp Cys
290                 295                 300 tcc gat ccg aca cta ctc ggc aac ttc atc gaa aac cac gac aat ccc      960
Ser Asp Pro Thr Leu Leu Gly Asn Phe Ile Glu Asn His Asp Asn Pro
305                 310                 315                 320 cgt ttc gcc tcc tac acc tcc gac tac tcg caa gcc aaa aac gtc ctc     1008
Arg Phe Ala Ser Tyr Thr Ser Asp Tyr Ser Gln Ala Lys Asn Val Leu
                325                 330                 335 agc tac atc ttc ctc tcc gac ggc atc ccc atc gtc tac gcc ggc gaa     1056
Ser Tyr Ile Phe Leu Ser Asp Gly Ile Pro Ile Val Tyr Ala Gly Glu
            340                 345                 350 gaa cag cac tac tcc ggc ggc aag gtg ccc tac aac cgc gaa gcg acc     1104
Glu Gln His Tyr Ser Gly Gly Lys Val Pro Tyr Asn Arg Glu Ala Thr
        355                 360                 365 tgg ctt tca ggc tac gac acc tcc gca gag ctg tac acc tgg ata gcc     1152
Trp Leu Ser Gly Tyr Asp Thr Ser Ala Glu Leu Tyr Thr Trp Ile Ala
370                 375                 380 acc acg aac gcg atc cgc aaa cta gcc atc tca gct gac tcg gcc tac     1200
Thr Thr Asn Ala Ile Arg Lys Leu Ala Ile Ser Ala Asp Ser Ala Tyr
385                 390                 395                 400 att acc tac gcg aat gat gca ttc tac act gac agc aac acc atc gca     1248
Ile Thr Tyr Ala Asn Asp Ala Phe Tyr Thr Asp Ser Asn Thr Ile Ala
                405                 410                 415 atg cgc aaa ggc acc tca ggg agc caa gtc atc acc gtc ctc tcc aac     1296
Met Arg Lys Gly Thr Ser Gly Ser Gln Val Ile Thr Val Leu Ser Asn
            420                 425                 430 aaa ggc tcc tca gga agc agc tac acc ctg acc ctc agc gga agc ggc     1344
Lys Gly Ser Ser Gly Ser Ser Tyr Thr Leu Thr Leu Ser Gly Ser Gly
        435                 440                 445 tac aca tcc ggc acg aag ctg atc gaa gcg tac aca tgc aca tcc gtg     1392
Tyr Thr Ser Gly Thr Lys Leu Ile Glu Ala Tyr Thr Cys Thr Ser Val
450                 455                 460 acc gtg gac tcg agc ggc gat att ccc gtg ccg atg gcg tcg gga tta     1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt     1488
Pro Arg Val Leu Leu Pro Ala Ser Val Val Asp Ser Ser Ser Leu Cys
                485                 490                 495 ggc ggg agc gga aga tta tac gtc gag taa                             1518
Gly Gly Ser Gly Arg Leu Tyr Val Glu
            500                 505

<210> SEQ ID NO 17
<211> LENGTH: 505
<212> TYPE: PRT
<213> ORGANISM: Aspergillus niger

<400> SEQUENCE: 17

Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
```

-continued

```
                65                  70                  75                  80
Ile Trp Ile Ser Pro Ile Thr Glu Gln Leu Pro Gln Asp Thr Ala Asp
                    85                  90                  95
Gly Glu Ala Tyr His Gly Tyr Trp Gln Gln Lys Ile Tyr Asp Val Asn
                    100                 105                 110
Ser Asn Phe Gly Thr Ala Asp Asp Leu Lys Ser Leu Ser Asp Ala Leu
                    115                 120                 125
His Ala Arg Gly Met Tyr Leu Met Val Asp Val Val Pro Asn His Met
            130                 135                 140
Gly Tyr Ala Gly Asn Gly Asn Asp Val Asp Tyr Ser Val Phe Asp Pro
145                 150                 155                 160
Phe Asp Ser Ser Ser Tyr Phe His Pro Tyr Cys Leu Ile Thr Asp Trp
                    165                 170                 175
Asp Asn Leu Thr Met Val Gln Asp Cys Trp Glu Gly Asp Thr Ile Val
                    180                 185                 190
Ser Leu Pro Asp Leu Asn Thr Thr Glu Thr Ala Val Arg Thr Ile Trp
                    195                 200                 205
Tyr Asp Trp Val Ala Asp Leu Val Ser Asn Tyr Ser Val Asp Gly Leu
            210                 215                 220
Arg Ile Asp Ser Val Leu Glu Val Glu Pro Asp Phe Phe Pro Gly Tyr
225                 230                 235                 240
Gln Glu Ala Ala Gly Val Tyr Cys Val Gly Glu Val Asp Asn Gly Asn
                    245                 250                 255
Pro Ala Leu Asp Cys Pro Tyr Gln Lys Val Leu Asp Gly Val Leu Asn
                    260                 265                 270
Tyr Pro Ile Tyr Trp Gln Leu Leu Tyr Ala Phe Glu Ser Ser Ser Gly
                    275                 280                 285
Ser Ile Ser Asn Leu Tyr Asn Met Ile Lys Ser Val Ala Ser Asp Cys
            290                 295                 300
Ser Asp Pro Thr Leu Leu Gly Asn Phe Ile Glu Asn His Asp Asn Pro
305                 310                 315                 320
Arg Phe Ala Ser Tyr Thr Ser Asp Tyr Ser Gln Ala Lys Asn Val Leu
                    325                 330                 335
Ser Tyr Ile Phe Leu Ser Asp Gly Ile Pro Ile Val Tyr Ala Gly Glu
                    340                 345                 350
Glu Gln His Tyr Ser Gly Gly Lys Val Pro Tyr Asn Arg Glu Ala Thr
            355                 360                 365
Trp Leu Ser Gly Tyr Asp Thr Ser Ala Glu Leu Tyr Thr Trp Ile Ala
        370                 375                 380
Thr Thr Asn Ala Ile Arg Lys Leu Ala Ile Ser Ala Asp Ser Ala Tyr
385                 390                 395                 400
Ile Thr Tyr Ala Asn Asp Ala Phe Tyr Thr Asp Ser Asn Thr Ile Ala
                    405                 410                 415
Met Arg Lys Gly Thr Ser Gly Ser Gln Val Ile Thr Val Leu Ser Asn
                    420                 425                 430
Lys Gly Ser Ser Gly Ser Ser Tyr Thr Leu Thr Leu Ser Gly Ser Gly
            435                 440                 445
Tyr Thr Ser Gly Thr Lys Leu Ile Glu Ala Tyr Thr Cys Thr Ser Val
            450                 455                 460
Thr Val Asp Ser Ser Gly Asp Ile Pro Val Pro Met Ala Ser Gly Leu
465                 470                 475                 480
Pro Arg Val Leu Leu Pro Ala Ser Val Val Asp Ser Ser Ser Leu Cys
                    485                 490                 495
```

Gly Gly Ser Gly Arg Leu Tyr Val Glu
          500                 505

<210> SEQ ID NO 18
<211> LENGTH: 2935
<212> TYPE: DNA
<213> ORGANISM: Penicillium chrysogenum

<400> SEQUENCE: 18

| | | | | | |
|---|---|---|---|---|---|
| ggttcgaaga | ggccaagata | ttatatcgag | gagtagagca | aaaataatgc | tgatatatta | 60 |
| atgaagagat | gacaattccg | acttccaact | tccaacttgg | acctcggagt | tgttgaatcc | 120 |
| ggtcctgctt | gccccatata | gcttccgacc | accggatttg | gaccaatcaa | cgcaggaaga | 180 |
| tgtcagcagc | ttcaggcatc | agcgtcacct | gaccttcgtg | ttgcccgcgt | caacgagcgc | 240 |
| gtctcaatga | tactttagac | ttgattaatt | tacaccttt | aatatttcca | atctcccgag | 300 |
| gatacctact | tcgtaacaat | ggttgaagat | agctacacgc | gcgaggagga | gaattacgag | 360 |
| gatgaagagc | tcgacgagac | cgtgagtatc | aaaagttgga | gatatagtta | ccgattgttg | 420 |
| acggttgcct | acatagagct | tcaaatcagt | caaagatgcg | gtgctgtttg | ctatagatat | 480 |
| tagcagttcg | atgctcacgc | ctcgtccatc | gcctgatcct | aagaaacatg | gagacgaatc | 540 |
| acccgcgtct | gcagctttga | gtgtgcata | ccatctgatg | caacaacgca | tcatctccaa | 600 |
| ccctcatgac | atgattggcg | ttttgctta | cggaacgcaa | tcttccaagt | tctatgatga | 660 |
| aaatgaggat | gaccgtggag | atctctcata | tcctcactgt | tatctgtaca | cggatcttga | 720 |
| tgttccatca | gcccaggaag | tcaagcaact | gcggtccctc | gcatctccag | cagatgctga | 780 |
| tgatgacgta | ctgcaagttt | tggagccatc | aaaggagcca | gcctccatgg | ccaacatgct | 840 |
| tttctgcgcc | aaccaaatct | ttacctcaaa | agctccaaac | tttgcttctc | gacgcctgtt | 900 |
| tgtcgtgacc | gacaacgata | tccccacgc | agacaacaaa | ggaatgcggt | ctgctgcaac | 960 |
| agttcgtgcg | agggacttgt | acgatcttgg | tgtcaatatc | gagttgtttc | ccatatctca | 1020 |
| accagaccac | gaattcgaca | cctctaaatt | ctacgacgta | ggtcattaac | cttgattgca | 1080 |
| taggggtata | ctcacaattg | gcaggacatt | atctacaaaa | catcgcccag | tgatggagat | 1140 |
| gccctgcat | acctacagcc | ggataccaac | acatcaacag | ctaaaggcga | tggactttca | 1200 |
| ttgctcaatt | ctctgttgtc | gagcatcaac | tcacgatctg | tccccgccg | atcgctgttc | 1260 |
| tcaaatgtgc | cacttgagat | cggacctaat | ttcaaaatat | ccgtcaatgg | atatttgctt | 1320 |
| ctcaagaaac | aagagcctgc | aaggagttgc | ttcgtctggc | aaggaggcga | gactgctcag | 1380 |
| attgccaaag | gagtcacaac | tctaatgtct | gatgacacag | ggcaggagat | tgagaagtct | 1440 |
| gacattcgca | aggcatacaa | gtttggtggc | gagcaggtat | cattcaccat | cgaagaacaa | 1500 |
| caggcgctaa | gaagcttcgg | tgacccggtg | atccgtatta | ttgggttcaa | gccactgtca | 1560 |
| gccctcccgt | tctgggccaa | tgtcaagcac | ccctcgttta | tttatccctc | tgaagaggac | 1620 |
| tacgtcggtt | caacaagagt | cttttctgca | ctgcatcaga | aactcctcga | atcggagaaa | 1680 |
| ctggctttgg | tctggttcat | ccccgcaga | aatgcctcac | cagtcttagc | tgctatgatt | 1740 |
| gcaggtgctg | agaagatcga | cgagaatggc | gtgcagaaaa | ttccacctgg | gatgtggatt | 1800 |
| atccctcttc | ctttcgcaga | tgatgtgcgc | caaaatccag | agagcaccgt | ccaccgggca | 1860 |
| ggagatgcgc | tgaacgacgc | catgcgagat | gttgttcgcc | agttgcagct | ccccaaggct | 1920 |
| gtgtacgatc | cttcaaaata | tccgaatcct | tgtgagcctt | cgtcacttca | atctttggga | 1980 |
| caatgatact | gactgattcg | cagcgcttca | atggcattat | cgtatcttac | aggctatcgc | 2040 |

-continued

```
cttggatgaa gatttcccag aatcaccaga tgacaagacc gtgcctaagt accgacaggt      2100
tcacaaggtt ggctgcttcc atgatcccag aaatgcccga acgtactgac caaatggatg      2160
ttctagcgcg ctggcgacta tattcttaga tgggccgagg aactgaaatt gcaagcctcc      2220
gagatgtttg gtgggtcagt agccgccacc tctacgctgg taaagcgagg tgccaagacc      2280
gaggcagctg gtgagcaccc atcaaagcgg gtgaaggttg aagacagtga gcccggagtg      2340
gaagacgaag tgaagaaatg ctatgcgaaa ggcactgttt ccaaggtgag cattcaaatt      2400
ctcccaggtg attgaccaaa ctaatactcg ccttcagctt acggtggccg tgctgaagga      2460
attcttgcat gcacatggcc gtgctacagc aggaaagaaa gcagatctcg tggaccgagt      2520
tgagcagtac tttgagcaga gtttaaac attgatttga agtttgctca ggatcgtctt       2580
ggggtggtcc aaggttgctg taatctgcgg cccgtttaat gagttatgag tgtatcctac      2640
ttgcctgttt ccataaggtc atagtcattt caaatgaatc gatatctttt atccaggatg      2700
atgttaggga cattatatat aagaatatac cggcgtttct ttttcgatgt cttttcagat      2760
gtatacaaag gcgcaagccg gtaaaaggcg tgaacgccct gatatatatc accgatactt      2820
ctttatgcaa aatgccagaa aatacctcta gcaactacag gggtagaaaa agagatcacc      2880
cttccaaggt tggcctagtc ttcctagata gccttctccg atagtcactt catac           2935
```

<210> SEQ ID NO 19
<211> LENGTH: 1977
<212> TYPE: DNA
<213> ORGANISM: Penicillium chrysogenum
<220> FEATURE:
<221> NAME/KEY: CDS
<222> LOCATION: (1)..(1977)

<400> SEQUENCE: 19

| | | | | | | | | | | | | | | | | |
|---|---|---|---|---|---|---|---|---|---|---|---|---|---|---|---|---|---|
| atg | gtt | gaa | gat | agc | tac | acg | cgc | gag | gag | gag | aat | tac | gag | gat | gaa | | 48 |
| Met | Val | Glu | Asp | Ser | Tyr | Thr | Arg | Glu | Glu | Glu | Asn | Tyr | Glu | Asp | Glu | | |
| 1 | | | | 5 | | | | | 10 | | | | | 15 | | | |

| gag | ctc | gac | gag | acc | agc | ttc | aaa | tca | gtc | aaa | gat | gcg | gtg | ctg | ttt | | 96 |
|---|---|---|---|---|---|---|---|---|---|---|---|---|---|---|---|---|---|
| Glu | Leu | Asp | Glu | Thr | Ser | Phe | Lys | Ser | Val | Lys | Asp | Ala | Val | Leu | Phe | | |
| | | | 20 | | | | | 25 | | | | | 30 | | | | |

| gct | ata | gat | att | agc | agt | tcg | atg | ctc | acg | cct | cgt | cca | tcg | cct | gat | | 144 |
|---|---|---|---|---|---|---|---|---|---|---|---|---|---|---|---|---|---|
| Ala | Ile | Asp | Ile | Ser | Ser | Ser | Met | Leu | Thr | Pro | Arg | Pro | Ser | Pro | Asp | | |
| | | 35 | | | | | 40 | | | | | 45 | | | | | |

| cct | aag | aaa | cat | gga | gac | gaa | tca | ccc | gcg | tct | gca | gct | ttg | aag | tgt | | 192 |
|---|---|---|---|---|---|---|---|---|---|---|---|---|---|---|---|---|---|
| Pro | Lys | Lys | His | Gly | Asp | Glu | Ser | Pro | Ala | Ser | Ala | Ala | Leu | Lys | Cys | | |
| 50 | | | | | 55 | | | | | 60 | | | | | | | |

| gca | tac | cat | ctg | atg | caa | caa | cgc | atc | atc | tcc | aac | cct | cat | gac | atg | | 240 |
|---|---|---|---|---|---|---|---|---|---|---|---|---|---|---|---|---|---|
| Ala | Tyr | His | Leu | Met | Gln | Gln | Arg | Ile | Ile | Ser | Asn | Pro | His | Asp | Met | | |
| 65 | | | | 70 | | | | | 75 | | | | | 80 | | | |

| att | ggc | gtt | ttg | ctt | tac | gga | acg | caa | tct | tcc | aag | ttc | tat | gat | gaa | | 288 |
|---|---|---|---|---|---|---|---|---|---|---|---|---|---|---|---|---|---|
| Ile | Gly | Val | Leu | Leu | Tyr | Gly | Thr | Gln | Ser | Ser | Lys | Phe | Tyr | Asp | Glu | | |
| | | | | 85 | | | | | 90 | | | | | 95 | | | |

| aat | gag | gat | gac | cgt | gga | gat | ctc | tca | tat | cct | cac | tgt | tat | ctg | tac | | 336 |
|---|---|---|---|---|---|---|---|---|---|---|---|---|---|---|---|---|---|
| Asn | Glu | Asp | Asp | Arg | Gly | Asp | Leu | Ser | Tyr | Pro | His | Cys | Tyr | Leu | Tyr | | |
| | | | 100 | | | | | 105 | | | | | 110 | | | | |

| acg | gat | ctt | gat | gtt | cca | tca | gcc | cag | gaa | gtc | aag | caa | ctg | cgg | tcc | | 384 |
|---|---|---|---|---|---|---|---|---|---|---|---|---|---|---|---|---|---|
| Thr | Asp | Leu | Asp | Val | Pro | Ser | Ala | Gln | Glu | Val | Lys | Gln | Leu | Arg | Ser | | |
| | | 115 | | | | | 120 | | | | | 125 | | | | | |

| ctc | gca | tct | cca | gca | gat | gct | gat | gat | gac | gta | ctg | caa | gtt | ttg | gag | | 432 |
|---|---|---|---|---|---|---|---|---|---|---|---|---|---|---|---|---|---|
| Leu | Ala | Ser | Pro | Ala | Asp | Ala | Asp | Asp | Asp | Val | Leu | Gln | Val | Leu | Glu | | |
| 130 | | | | | 135 | | | | | 140 | | | | | | | |

| cca | tca | aag | gag | cca | gcc | tcc | atg | gcc | aac | atg | ctt | ttc | tgc | gcc | aac | | 480 |

```
Pro Ser Lys Glu Pro Ala Ser Met Ala Asn Met Leu Phe Cys Ala Asn
145                 150                 155                 160 caa atc ttt acc tca aaa gct cca aac ttt gct tct cga cgc ctg ttt      528
Gln Ile Phe Thr Ser Lys Ala Pro Asn Phe Ala Ser Arg Arg Leu Phe
                165                 170                 175 gtc gtg acc gac aac gat aat ccc cac gca gac aac aaa gga atg cgg      576
Val Val Thr Asp Asn Asp Asn Pro His Ala Asp Asn Lys Gly Met Arg
            180                 185                 190 tct gct gca aca gtt cgt gcg agg gac ttg tac gat ctt ggt gtc aat      624
Ser Ala Ala Thr Val Arg Ala Arg Asp Leu Tyr Asp Leu Gly Val Asn
                195                 200                 205 atc gag ttg ttt ccc ata tct caa cca gac cac gaa ttc gac acc tct      672
Ile Glu Leu Phe Pro Ile Ser Gln Pro Asp His Glu Phe Asp Thr Ser
210                 215                 220 aaa ttc tac gac gac att atc tac aaa aca tcg ccc agt gat gga gat      720
Lys Phe Tyr Asp Asp Ile Ile Tyr Lys Thr Ser Pro Ser Asp Gly Asp
225                 230                 235                 240 gcc cct gca tac cta cag ccg gat acc aac aca tca aca gct aaa ggc      768
Ala Pro Ala Tyr Leu Gln Pro Asp Thr Asn Thr Ser Thr Ala Lys Gly
                245                 250                 255 gat gga ctt tca ttg ctc aat tct ctg ttg tcg agc atc aac tca cga      816
Asp Gly Leu Ser Leu Leu Asn Ser Leu Leu Ser Ser Ile Asn Ser Arg
            260                 265                 270 tct gtc ccc cgc cga tcg ctg ttc tca aat gtg cca ctt gag atc gga      864
Ser Val Pro Arg Arg Ser Leu Phe Ser Asn Val Pro Leu Glu Ile Gly
                275                 280                 285 cct aat ttc aaa ata tcc gtc aat gga tat ttg ctt ctc aag aaa caa      912
Pro Asn Phe Lys Ile Ser Val Asn Gly Tyr Leu Leu Leu Lys Lys Gln
290                 295                 300 gag cct gca agg agt tgc ttc gtc tgg caa gga ggc gag act gct cag      960
Glu Pro Ala Arg Ser Cys Phe Val Trp Gln Gly Gly Glu Thr Ala Gln
305                 310                 315                 320 att gcc aaa gga gtc aca act cta atg tct gat gac aca ggg cag gag     1008
Ile Ala Lys Gly Val Thr Thr Leu Met Ser Asp Asp Thr Gly Gln Glu
                325                 330                 335 att gag aag tct gac att cgc aag gca tac aag ttt ggt ggc gag cag     1056
Ile Glu Lys Ser Asp Ile Arg Lys Ala Tyr Lys Phe Gly Gly Glu Gln
            340                 345                 350 gta tca ttc acc atc gaa gaa caa cag gcg cta aga agc ttc ggt gac     1104
Val Ser Phe Thr Ile Glu Glu Gln Gln Ala Leu Arg Ser Phe Gly Asp
                355                 360                 365 ccg gtg atc cgt att att ggg ttc aag cca ctg tca gcc ctc ccg ttc     1152
Pro Val Ile Arg Ile Ile Gly Phe Lys Pro Leu Ser Ala Leu Pro Phe
370                 375                 380 tgg gcc aat gtc aag cac ccc tcg ttt att tat ccc tct gaa gag gac     1200
Trp Ala Asn Val Lys His Pro Ser Phe Ile Tyr Pro Ser Glu Glu Asp
385                 390                 395                 400 tac gtc ggt tca aca aga gtc ttt tct gca ctg cat cag aaa ctc ctc     1248
Tyr Val Gly Ser Thr Arg Val Phe Ser Ala Leu His Gln Lys Leu Leu
                405                 410                 415 gaa tcg gag aaa ctg gct ttg gtc tgg ttc atc ccc cgc aga aat gcc     1296
Glu Ser Glu Lys Leu Ala Leu Val Trp Phe Ile Pro Arg Arg Asn Ala
            420                 425                 430 tca cca gtc tta gct gct atg att gca ggt gct gag aag atc gac gag     1344
Ser Pro Val Leu Ala Ala Met Ile Ala Gly Ala Glu Lys Ile Asp Glu
                435                 440                 445 aat ggc gtg cag aaa att cca cct ggg atg tgg att atc cct ctt cct     1392
Asn Gly Val Gln Lys Ile Pro Pro Gly Met Trp Ile Ile Pro Leu Pro
450                 455                 460
```

```
ttc gca gat gat gtg cgc caa aat cca gag agc acc gtc cac cgg gca      1440
Phe Ala Asp Asp Val Arg Gln Asn Pro Glu Ser Thr Val His Arg Ala
465                 470                 475                 480 gga gat gcg ctg aac gac gcc atg cga gat gtt gtt cgc cag ttg cag      1488
Gly Asp Ala Leu Asn Asp Ala Met Arg Asp Val Val Arg Gln Leu Gln
                485                 490                 495 ctc ccc aag gct gtg tac gat cct tca aaa tat ccg aat cct tcg ctt      1536
Leu Pro Lys Ala Val Tyr Asp Pro Ser Lys Tyr Pro Asn Pro Ser Leu
            500                 505                 510 caa tgg cat tat cgt atc tta cag gct atc gcc ttg gat gaa gat ttc      1584
Gln Trp His Tyr Arg Ile Leu Gln Ala Ile Ala Leu Asp Glu Asp Phe
        515                 520                 525 cca gaa tca cca gat gac aag acc gtg cct aag tac cga cag gtt cac      1632
Pro Glu Ser Pro Asp Asp Lys Thr Val Pro Lys Tyr Arg Gln Val His
    530                 535                 540 aag gtt ggc tgc ttc cat gat ccc aga aat gcc cga aca tgg gcc gag      1680
Lys Val Gly Cys Phe His Asp Pro Arg Asn Ala Arg Thr Trp Ala Glu
545                 550                 555                 560 gaa ctg aaa ttg caa gcc tcc gag atg ttt ggt ggg tca gta gcc gcc      1728
Glu Leu Lys Leu Gln Ala Ser Glu Met Phe Gly Gly Ser Val Ala Ala
                565                 570                 575 acc tct acg ctg gta aag cga ggt gcc aag acc gag gca gct ggt gag      1776
Thr Ser Thr Leu Val Lys Arg Gly Ala Lys Thr Glu Ala Ala Gly Glu
            580                 585                 590 cac cca tca aag cgg gtg aag gtt gaa gac agt gag ccc gga gtg gaa      1824
His Pro Ser Lys Arg Val Lys Val Glu Asp Ser Glu Pro Gly Val Glu
        595                 600                 605 gac gaa gtg aag aaa tgc tat gcg aaa ggc act gtt tcc aag ctt acg      1872
Asp Glu Val Lys Lys Cys Tyr Ala Lys Gly Thr Val Ser Lys Leu Thr
    610                 615                 620 gtg gcc gtg ctg aag gaa ttc ttg cat gca cat ggc cgt gct aca gca      1920
Val Ala Val Leu Lys Glu Phe Leu His Ala His Gly Arg Ala Thr Ala
625                 630                 635                 640 gga aag aaa gca gat ctc gtg gac cga gtt gag cag tac ttt gag cag      1968
Gly Lys Lys Ala Asp Leu Val Asp Arg Val Glu Gln Tyr Phe Glu Gln
                645                 650                 655 aag ttt taa                                                          1977
Lys Phe <210> SEQ ID NO 20
<211> LENGTH: 658
<212> TYPE: PRT
<213> ORGANISM: Penicillium chrysogenum

<400> SEQUENCE: 20

Met Val Glu Asp Ser Tyr Thr Arg Glu Glu Asn Tyr Glu Asp Glu
1               5                   10                  15

Glu Leu Asp Glu Thr Ser Phe Lys Ser Val Lys Asp Ala Val Leu Phe
                20                  25                  30

Ala Ile Asp Ile Ser Ser Ser Met Leu Thr Pro Arg Pro Ser Pro Asp
            35                  40                  45

Pro Lys Lys His Gly Asp Glu Ser Pro Ala Ser Ala Ala Leu Lys Cys
        50                  55                  60

Ala Tyr His Leu Met Gln Gln Arg Ile Ile Ser Asn Pro His Asp Met
65                  70                  75                  80

Ile Gly Val Leu Leu Tyr Gly Thr Gln Ser Ser Lys Phe Tyr Asp Glu
                85                  90                  95

Asn Glu Asp Asp Arg Gly Asp Leu Ser Tyr Pro His Cys Tyr Leu Tyr
            100                 105                 110
```

```
Thr Asp Leu Asp Val Pro Ser Ala Gln Glu Val Lys Gln Leu Arg Ser
        115                 120                 125

Leu Ala Ser Pro Ala Asp Ala Asp Asp Val Leu Gln Val Leu Glu
    130                 135                 140

Pro Ser Lys Glu Pro Ala Ser Met Ala Asn Met Leu Phe Cys Ala Asn
145                 150                 155                 160

Gln Ile Phe Thr Ser Lys Ala Pro Asn Phe Ala Ser Arg Arg Leu Phe
                165                 170                 175

Val Val Thr Asp Asn Asp Asn Pro His Ala Asp Asn Lys Gly Met Arg
            180                 185                 190

Ser Ala Ala Thr Val Arg Ala Arg Asp Leu Tyr Asp Leu Gly Val Asn
        195                 200                 205

Ile Glu Leu Phe Pro Ile Ser Gln Pro Asp His Glu Phe Asp Thr Ser
    210                 215                 220

Lys Phe Tyr Asp Asp Ile Ile Tyr Lys Thr Ser Pro Ser Asp Gly Asp
225                 230                 235                 240

Ala Pro Ala Tyr Leu Gln Pro Asp Thr Asn Thr Ser Thr Ala Lys Gly
                245                 250                 255

Asp Gly Leu Ser Leu Leu Asn Ser Leu Leu Ser Ser Ile Asn Ser Arg
            260                 265                 270

Ser Val Pro Arg Arg Ser Leu Phe Ser Asn Val Pro Leu Glu Ile Gly
        275                 280                 285

Pro Asn Phe Lys Ile Ser Val Asn Gly Tyr Leu Leu Leu Lys Lys Gln
    290                 295                 300

Glu Pro Ala Arg Ser Cys Phe Val Trp Gln Gly Gly Glu Thr Ala Gln
305                 310                 315                 320

Ile Ala Lys Gly Val Thr Thr Leu Met Ser Asp Asp Thr Gly Gln Glu
                325                 330                 335

Ile Glu Lys Ser Asp Ile Arg Lys Ala Tyr Lys Phe Gly Gly Glu Gln
            340                 345                 350

Val Ser Phe Thr Ile Glu Glu Gln Gln Ala Leu Arg Ser Phe Gly Asp
        355                 360                 365

Pro Val Ile Arg Ile Ile Gly Phe Lys Pro Leu Ser Ala Leu Pro Phe
    370                 375                 380

Trp Ala Asn Val Lys His Pro Ser Phe Ile Tyr Pro Ser Glu Glu Asp
385                 390                 395                 400

Tyr Val Gly Ser Thr Arg Val Phe Ser Ala Leu His Gln Lys Leu Leu
                405                 410                 415

Glu Ser Glu Lys Leu Ala Leu Val Trp Phe Ile Pro Arg Arg Asn Ala
            420                 425                 430

Ser Pro Val Leu Ala Ala Met Ile Ala Gly Ala Glu Lys Ile Asp Glu
        435                 440                 445

Asn Gly Val Gln Lys Ile Pro Pro Gly Met Trp Ile Ile Pro Leu Pro
    450                 455                 460

Phe Ala Asp Asp Val Arg Gln Asn Pro Glu Ser Thr Val His Arg Ala
465                 470                 475                 480

Gly Asp Ala Leu Asn Asp Ala Met Arg Asp Val Val Arg Gln Leu Gln
                485                 490                 495

Leu Pro Lys Ala Val Tyr Asp Pro Ser Lys Tyr Pro Asn Pro Ser Leu
            500                 505                 510

Gln Trp His Tyr Arg Ile Leu Gln Ala Ile Ala Leu Asp Glu Asp Phe
        515                 520                 525
```

```
Pro Glu Ser Pro Asp Asp Lys Thr Val Pro Lys Tyr Arg Gln Val His
    530                 535                 540

Lys Val Gly Cys Phe His Asp Pro Arg Asn Ala Arg Thr Trp Ala Glu
545                 550                 555                 560

Glu Leu Lys Leu Gln Ala Ser Glu Met Phe Gly Gly Ser Val Ala Ala
                565                 570                 575

Thr Ser Thr Leu Val Lys Arg Gly Ala Lys Thr Glu Ala Ala Gly Glu
            580                 585                 590

His Pro Ser Lys Arg Val Lys Val Glu Asp Ser Glu Pro Gly Val Glu
        595                 600                 605

Asp Glu Val Lys Lys Cys Tyr Ala Lys Gly Thr Val Ser Lys Leu Thr
610                 615                 620

Val Ala Val Leu Lys Glu Phe Leu His Ala His Gly Arg Ala Thr Ala
625                 630                 635                 640

Gly Lys Lys Ala Asp Leu Val Asp Arg Val Glu Gln Tyr Phe Glu Gln
                645                 650                 655

Lys Phe

<210> SEQ ID NO 21
<211> LENGTH: 3605
<212> TYPE: DNA
<213> ORGANISM: Penicillium chrysogenum

<400> SEQUENCE: 21
gatttcggat atgttatgac ctaaggagag ttgagttggc gataaagtcg atgtgaagtt     60
gcatcgaggg gaagaagtgg cagttatcgc tacgatccaa ttcttaatga aagccttatt    120
tccacttcca aatagaggga gctggcttct aacgacgcac agaccaccaa acaccaacaa    180
agacggcgtg tgatgtcatg tgccttcgtg tttcggtcta aaccgcaagt ggaaatatca    240
cgcgtctgcc tgttgtcttg agccccaaag caactttgtc ttgccatttt cccaacatca    300
tcatcattat ggcggagaaa gaggctacag tttacattgt agacatggga cggtctatgg    360
gcgagcgcca ccatggccgt cctatgacag atctcgaatg ggccatgcag tatgtctggg    420
ataggatcac tgccacggta tgtgacttga ccttgttcaa cgccagagaa ctgacaattc    480
caggtggcta ctggtcgaaa gacggctacg gttggcgtag ttggactcag gactgatggt    540
gagtggtcgg ctaccagtca gcacccattg ggacccttgt ctcatgtttg aacaggaac     600 tatcaacgac ttggaagaag agagcttttc taatatttct attctcttcg gtcttggcca    660
gtatgtgtgg cttaattaat cgacagcttt atgccgagtc gcctgactaa attgtctttc    720
agagtcctca tgcctgatat ccggaaactg cgagaaacga tcaagcccag caacactaac    780
agaggcgatg gtatgtgact gttgaagtct tgtcaagctg cttattctga ctttatataa    840
gccatctctt ctattgtcat tgccatgcag atgatcattg actacacgaa gaaaaacaaa    900
tacaagcgca agatcatctt ggtgaccaat ggtaccggcg tgatgagcga tgataatatc    960
gaaggcatca ttgaaaagat gaaagaggtt aacattgagt tggtggtcat gtatgtttct   1020
tgccgacatg acttcacatt catgctaata ctatgcagtg gagccgattt tgatgacgct   1080
gagtatggtg taaggaaga agacaaagac agtcgaaagg ttctaagcca tctccaatct   1140
attctgttat tcatgttgac aaagcgctct gcaggctgaa acgagactt ttctccgaag    1200 cctggctgag gactgcgaag gtgcttatgg aacgctggag caagccgttt cggaattgga   1260
tattccccgt atcaaagtga ccaagagcat gccatctttc aagggaaacc tcacgctcgg   1320
caatcccgag gagtatgaca cggctatgac tatacccgtg gagcgatact tccgaaccta   1380
```

```
cgtcgccaaa ccaatctcag cgagctcgtt cgtaccacgc tccggcaccg aacctggaag    1440
tcaagcaccg gttaaaggcg atgctgaagg cgatgctctc gcctcagtgc gaacatcacg    1500
gacgtatcag atcacagatg agtccgcacc aggtggtaag atcgacgttg aacgcgatga    1560
cctcgccaag gggtacgagt acggacgtac cgcggttcct atcgagcaaa ccgatgagaa    1620
tgttgcaaat ctacaaacat ttgctggtat ggggctgatc gggttcgttc agaaggatca    1680
ggtgtgtctt tatgccaata ttaagtgcta acagctaa tccgtgactt agtatgaccg     1740
gtacatgcat atgtcaaaca cgaatatcat catccctcag cgtgcaaatg actatgcgtc    1800
tcttgcgttg tcttctctca ttcatgcact ctacgaattg gagtcctatg cggttgcccg    1860
cttggtgacc aaagaatcca aaccaccgat gcttgtgttg ctagctccat ctatcgaggc    1920
agactatgag tgcttgattg aagtacagct tccatttgca gaagacgtgc ggtcgtatcg    1980
gttcccacct ttggataaga ttatcactgt ctctggcaag gtggtgactg aacatcgaaa    2040
cctcccaagc gtggcgttga agatgcgat gagtaactac gtggacagca tggattttgt    2100
caccacaaac gacgaagggt aagtatagtc tacttgatta tcgactttat cagttaatca    2160
aaagagccag gcaagccact gacgatctcc caatcgacga gtcattctca ccgttattgc    2220
accgcatcga atcagcagtt cgatatcgtg ctgtgcatcc caatgaccct gtcctcgacc    2280
cctcagagcg gctcactgaa ttcgcacacc cctcagaaga catggtcaag aactccaaat    2340
cccatcttga gaaattgatg tccatagcag atgtcaagaa aggtaacctc gatttccata    2400
ctacatccgg aagatacccc actcacccac gcattttgtc ttatagttcc accgaagaca    2460
aaaggccgta acgccaacg tgaaacagag aaacctctct caggtttgga cgtggacgcc    2520
ctgctcagcc tcgaacccaa gcgaacgaag atttccaccg agaatgcaat cccagagttc    2580
aagcaaacac tttcccgcgc ggaaaacatc gacgcaatcc acgacgctgt gcagcagatg    2640
gctaaaatca tcgagagcca gatcacacac agcctcggtc attcaaatta cgaccgtgtt    2700 atcgagggc ttggtactat gcgtgaagaa ctggtggact atgaggaacc ggcggtgtac     2760
aatgactttg tgcgtcagtt gaagggcaag atgttgcggg aggagctggg tggggatcgg    2820
agggagctgt ggtggtttgt aaggaaggga agcttgggc tcattggcaa gagtgaggtg     2880
gatagctcgg ctgttgagga gcaagaggct caagaggtga ggtttggcct tttattgtgg    2940
aatggaacga gtgctaacac tgcgtatagt ttctggctcc caattgagga attgagtggg    3000
ggggcgggtt attgtctcgc tattcaaaca tgaaatagtg agcatacgag ggatgtggaa    3060
tattcatact attctctatg ccagatttac gcgatgtaga gcttcctgtg gaagttatgt    3120
tatatggtac gtcgtagaag taaggccggg aaacggagta tagtccacct caggtgatga    3180
ggtccaataa tactgaccac ccagatcaaa ggatacggat tggaggggtt acggagaaat    3240
ggaaatattg agcaagccca tgaacagcat tgtcatatag acgtagaatt gacacataca    3300
ggaacgaagc ccgcagacag aacaatatga ggcacgaagt gaatcggtgc ccaattgcaa    3360
ggcatgacga gtcgtcaatg aacaacagaa ccaaacgccg tgcataacat gcccaataac    3420
cagtattcgc tccagaaaac agcaaaagac cgagatttgc aaactcaaac attaaaaagc    3480
atccagatgc atcagggaaa aggggtatgc agaagtgttg tcccggtagg acgagaagaa    3540
tggaacaaga agcgctccga ggaaacttgg agagtttcga ggggcgaaag aagagagcag    3600
aacat                                                                3605

<210> SEQ ID NO 22
```

```
<211> LENGTH: 2157
<212> TYPE: DNA
<213> ORGANISM: Penicillium chrysogenum
<220> FEATURE:
<221> NAME/KEY: CDS
<222> LOCATION: (1)..(2157)

<400> SEQUENCE: 22 atg gcg gag aaa gag gct aca gtt tac att gta gac atg gga cgg tct      48
Met Ala Glu Lys Glu Ala Thr Val Tyr Ile Val Asp Met Gly Arg Ser
1               5                   10                  15 atg ggc gag cgc cac cat ggc cgt cct atg aca gat ctc gaa tgg gcc      96
Met Gly Glu Arg His His Gly Arg Pro Met Thr Asp Leu Glu Trp Ala
            20                  25                  30 atg cag tat gtc tgg gat agg atc act gcc acg gtg gct act ggt cga     144
Met Gln Tyr Val Trp Asp Arg Ile Thr Ala Thr Val Ala Thr Gly Arg
        35                  40                  45 aag acg gct acg gtt ggc gta gtt gga ctc agg act gat gtc agc acc     192
Lys Thr Ala Thr Val Gly Val Val Gly Leu Arg Thr Asp Val Ser Thr
    50                  55                  60 cat tgg gac cct tgt ctc atg ttt gga aca gga act atc aac gac ttg     240
His Trp Asp Pro Cys Leu Met Phe Gly Thr Gly Thr Ile Asn Asp Leu
65                  70                  75                  80 gaa gaa gag agc ttt tct aat att tct att ctc ttc ggt ctt ggc caa     288
Glu Glu Glu Ser Phe Ser Asn Ile Ser Ile Leu Phe Gly Leu Gly Gln
                85                  90                  95 gtc ctc atg cct gat atc cgg aaa ctg cga gaa acg atc aag ccc agc     336
Val Leu Met Pro Asp Ile Arg Lys Leu Arg Glu Thr Ile Lys Pro Ser
            100                 105                 110 aac act aac aga ggc gat gcc atc tct tct att gtc att gcc atg cag     384
Asn Thr Asn Arg Gly Asp Ala Ile Ser Ser Ile Val Ile Ala Met Gln
        115                 120                 125 atg atc att gac tac acg aag aaa aac aaa tac aag cgc aag atc atc     432
Met Ile Ile Asp Tyr Thr Lys Lys Asn Lys Tyr Lys Arg Lys Ile Ile
    130                 135                 140 ttg gtg acc aat ggt acc ggc gtg atg agc gat gat aat atc gaa ggc     480
Leu Val Thr Asn Gly Thr Gly Val Met Ser Asp Asp Asn Ile Glu Gly
145                 150                 155                 160 atc att gaa aag atg aaa gag gtt aac att gag ttg gtg gtc atg tat     528
Ile Ile Glu Lys Met Lys Glu Val Asn Ile Glu Leu Val Val Met Tyr
                165                 170                 175 tat ggt gta aag gaa gaa gac aaa gac agt cga aag gct gaa aac gag     576
Tyr Gly Val Lys Glu Glu Asp Lys Asp Ser Arg Lys Ala Glu Asn Glu
            180                 185                 190 act ttt ctc cga agc ctg gct gag gac tgc gaa ggt gct tat gga acg     624
Thr Phe Leu Arg Ser Leu Ala Glu Asp Cys Glu Gly Ala Tyr Gly Thr
        195                 200                 205 ctg gag caa gcc gtt tcg gaa ttg gat att ccc cgt atc aaa gtg acc     672
Leu Glu Gln Ala Val Ser Glu Leu Asp Ile Pro Arg Ile Lys Val Thr
    210                 215                 220 aag agc atg cca tct ttc aag gga aac ctc acg ctc ggc aat ccc gag     720
Lys Ser Met Pro Ser Phe Lys Gly Asn Leu Thr Leu Gly Asn Pro Glu
225                 230                 235                 240 gag tat gac acg gct atg act ata ccc gtg gag cga tac ttc cga acc     768
Glu Tyr Asp Thr Ala Met Thr Ile Pro Val Glu Arg Tyr Phe Arg Thr
                245                 250                 255 tac gtc gcc aaa cca atc tca gcg agc tcg ttc gta cca cgc tcc ggc     816
Tyr Val Ala Lys Pro Ile Ser Ala Ser Ser Phe Val Pro Arg Ser Gly
            260                 265                 270 acc gaa cct gga agt caa gca ccg gtt aaa ggc gat gct gaa ggc gat     864
Thr Glu Pro Gly Ser Gln Ala Pro Val Lys Gly Asp Ala Glu Gly Asp
```

-continued

```
                    275                 280                 285
gct ctc gcc tca gtg cga aca tca cgg acg tat cag atc aca gat gag        912
Ala Leu Ala Ser Val Arg Thr Ser Arg Thr Tyr Gln Ile Thr Asp Glu
    290                 295                 300 tcc gca cca ggt ggt aag atc gac gtt gaa cgc gat gac ctc gcc aag        960
Ser Ala Pro Gly Gly Lys Ile Asp Val Glu Arg Asp Asp Leu Ala Lys
305                 310                 315                 320 ggg tac gag tac gga cgt acc gcg gtt cct atc gag caa acc gat gag       1008
Gly Tyr Glu Tyr Gly Arg Thr Ala Val Pro Ile Glu Gln Thr Asp Glu
                325                 330                 335 aat gtt gca aat cta caa aca ttt gct ggt atg ggg ctg atc ggg ttc       1056
Asn Val Ala Asn Leu Gln Thr Phe Ala Gly Met Gly Leu Ile Gly Phe
        340                 345                 350 gtt cag aag gat cag tat gac cgg tac atg cat atg tca aac acg aat       1104
Val Gln Lys Asp Gln Tyr Asp Arg Tyr Met His Met Ser Asn Thr Asn
    355                 360                 365 atc atc atc cct cag cgt gca aat gac tat gcg tct ctt gcg ttg tct       1152
Ile Ile Ile Pro Gln Arg Ala Asn Asp Tyr Ala Ser Leu Ala Leu Ser
370                 375                 380 tct ctc att cat gca ctc tac gaa ttg gag tcc tat gcg gtt gcc cgc       1200
Ser Leu Ile His Ala Leu Tyr Glu Leu Glu Ser Tyr Ala Val Ala Arg
385                 390                 395                 400 ttg gtg acc aaa gaa tcc aaa cca ccg atg ctt gtg ttg cta gct cca       1248
Leu Val Thr Lys Glu Ser Lys Pro Pro Met Leu Val Leu Leu Ala Pro
                405                 410                 415 tct atc gag gca gac tat gag tgc ttg att gaa gta cag ctt cca ttt       1296
Ser Ile Glu Ala Asp Tyr Glu Cys Leu Ile Glu Val Gln Leu Pro Phe
        420                 425                 430 gca gaa gac gtg cgg tcg tat cgg ttc cca cct ttg gat aag att atc       1344
Ala Glu Asp Val Arg Ser Tyr Arg Phe Pro Pro Leu Asp Lys Ile Ile
    435                 440                 445 act gtc tct ggc aag gtg gtg act gaa cat cga aac ctc cca agc gtg       1392
Thr Val Ser Gly Lys Val Val Thr Glu His Arg Asn Leu Pro Ser Val
450                 455                 460 gcg ttg aaa gat gcg atg agt aac tac gtg gac agc atg gat ttt gtc       1440
Ala Leu Lys Asp Ala Met Ser Asn Tyr Val Asp Ser Met Asp Phe Val
465                 470                 475                 480 acc aca aac gac gaa ggg caa gcc act gac gat ctc cca atc gac gag       1488
Thr Thr Asn Asp Glu Gly Gln Ala Thr Asp Asp Leu Pro Ile Asp Glu
                485                 490                 495 tca ttc tca ccg tta ttg cac cgc atc gaa tca gca gtt cga tat cgt       1536
Ser Phe Ser Pro Leu Leu His Arg Ile Glu Ser Ala Val Arg Tyr Arg
        500                 505                 510 gct gtg cat ccc aat gac cct gtc ctc gac ccc tca gag cgg ctc act       1584
Ala Val His Pro Asn Asp Pro Val Leu Asp Pro Ser Glu Arg Leu Thr
    515                 520                 525 gaa ttc gca cac ccc tca gaa gac atg gtc aag aac tcc aaa tcc cat       1632
Glu Phe Ala His Pro Ser Glu Asp Met Val Lys Asn Ser Lys Ser His
530                 535                 540 ctt gag aaa ttg atg tcc ata gca gat gtc aag aaa gtt cca ccg aag       1680
Leu Glu Lys Leu Met Ser Ile Ala Asp Val Lys Lys Val Pro Pro Lys
545                 550                 555                 560 aca aaa ggc cgt aaa cgc caa cgt gaa aca gag aaa cct ctc tca ggt       1728
Thr Lys Gly Arg Lys Arg Gln Arg Glu Thr Glu Lys Pro Leu Ser Gly
                565                 570                 575 ttg gac gtg gac gcc ctg ctc agc ctc gaa ccc aag cga acg aag att       1776
Leu Asp Val Asp Ala Leu Leu Ser Leu Glu Pro Lys Arg Thr Lys Ile
        580                 585                 590 tcc acc gag aat gca atc cca gag ttc aag caa aca ctt tcc cgc gcg       1824
```

```
                Ser Thr Glu Asn Ala Ile Pro Glu Phe Lys Gln Thr Leu Ser Arg Ala
                            595                 600                 605 gaa aac atc gac gca atc cac gac gct gtg cag cag atg gct aaa atc       1872
Glu Asn Ile Asp Ala Ile His Asp Ala Val Gln Gln Met Ala Lys Ile
610                 615                 620 atc gag agc cag atc aca cac agc ctc ggt cat tca aat tac gac cgt       1920
Ile Glu Ser Gln Ile Thr His Ser Leu Gly His Ser Asn Tyr Asp Arg
625                 630                 635                 640 gtt atc gag ggg ctt ggt act atg cgt gaa gaa ctg gtg gac tat gag       1968
Val Ile Glu Gly Leu Gly Thr Met Arg Glu Glu Leu Val Asp Tyr Glu
                645                 650                 655 gaa ccg gcg gtg tac aat gac ttt gtg cgt cag ttg aag ggc aag atg       2016
Glu Pro Ala Val Tyr Asn Asp Phe Val Arg Gln Leu Lys Gly Lys Met
            660                 665                 670 ttg cgg gag gag ctg ggt ggg gat cgg agg gag ctg tgg tgg ttt gta       2064
Leu Arg Glu Glu Leu Gly Gly Asp Arg Arg Glu Leu Trp Trp Phe Val
        675                 680                 685 agg aag gga aag ctt ggg ctc att ggc aag agt gag gtg gat agc tcg       2112
Arg Lys Gly Lys Leu Gly Leu Ile Gly Lys Ser Glu Val Asp Ser Ser
    690                 695                 700 gct gtt gag gag caa gag gct caa gag ttt ctg gct ccc aat tga           2157
Ala Val Glu Glu Gln Glu Ala Gln Glu Phe Leu Ala Pro Asn
705                 710                 715

<210> SEQ ID NO 23
<211> LENGTH: 718
<212> TYPE: PRT
<213> ORGANISM: Penicillium chrysogenum

<400> SEQUENCE: 23

Met Ala Glu Lys Glu Ala Thr Val Tyr Ile Val Asp Met Gly Arg Ser
1               5                   10                  15

Met Gly Glu Arg His His Gly Arg Pro Met Thr Asp Leu Glu Trp Ala
            20                  25                  30

Met Gln Tyr Val Trp Asp Arg Ile Thr Ala Thr Val Ala Thr Gly Arg
        35                  40                  45

Lys Thr Ala Thr Val Gly Val Val Gly Leu Arg Thr Asp Val Ser Thr
    50                  55                  60

His Trp Asp Pro Cys Leu Met Phe Gly Thr Gly Thr Ile Asn Asp Leu
65                  70                  75                  80

Glu Glu Glu Ser Phe Ser Asn Ile Ser Ile Leu Phe Gly Leu Gly Gln
                85                  90                  95

Val Leu Met Pro Asp Ile Arg Lys Leu Arg Glu Thr Ile Lys Pro Ser
            100                 105                 110

Asn Thr Asn Arg Gly Asp Ala Ile Ser Ser Ile Val Ile Ala Met Gln
        115                 120                 125

Met Ile Ile Asp Tyr Thr Lys Lys Asn Lys Tyr Lys Arg Lys Ile Ile
    130                 135                 140

Leu Val Thr Asn Gly Thr Gly Val Met Ser Asp Asp Asn Ile Glu Gly
145                 150                 155                 160

Ile Ile Glu Lys Met Lys Glu Val Asn Ile Glu Leu Val Val Met Tyr
                165                 170                 175

Tyr Gly Val Lys Glu Glu Asp Lys Asp Ser Arg Lys Ala Glu Asn Glu
            180                 185                 190

Thr Phe Leu Arg Ser Leu Ala Glu Asp Cys Glu Gly Ala Tyr Gly Thr
        195                 200                 205

Leu Glu Gln Ala Val Ser Glu Leu Asp Ile Pro Arg Ile Lys Val Thr
```

```
            210                 215                 220
Lys Ser Met Pro Ser Phe Lys Gly Asn Leu Thr Leu Gly Asn Pro Glu
225                 230                 235                 240

Glu Tyr Asp Thr Ala Met Thr Ile Pro Val Glu Arg Tyr Phe Arg Thr
                245                 250                 255

Tyr Val Ala Lys Pro Ile Ser Ala Ser Ser Phe Val Pro Arg Ser Gly
                260                 265                 270

Thr Glu Pro Gly Ser Gln Ala Pro Val Lys Gly Asp Ala Glu Gly Asp
            275                 280                 285

Ala Leu Ala Ser Val Arg Thr Ser Arg Thr Tyr Gln Ile Thr Asp Glu
        290                 295                 300

Ser Ala Pro Gly Gly Lys Ile Asp Val Glu Arg Asp Asp Leu Ala Lys
305                 310                 315                 320

Gly Tyr Glu Tyr Gly Arg Thr Ala Val Pro Ile Glu Gln Thr Asp Glu
                325                 330                 335

Asn Val Ala Asn Leu Gln Thr Phe Ala Gly Met Gly Leu Ile Gly Phe
            340                 345                 350

Val Gln Lys Asp Gln Tyr Asp Arg Tyr Met His Met Ser Asn Thr Asn
        355                 360                 365

Ile Ile Ile Pro Gln Arg Ala Asn Asp Tyr Ala Ser Leu Ala Leu Ser
370                 375                 380

Ser Leu Ile His Ala Leu Tyr Glu Leu Glu Ser Tyr Ala Val Ala Arg
385                 390                 395                 400

Leu Val Thr Lys Glu Ser Lys Pro Pro Met Leu Val Leu Leu Ala Pro
                405                 410                 415

Ser Ile Glu Ala Asp Tyr Glu Cys Leu Ile Glu Val Gln Leu Pro Phe
            420                 425                 430

Ala Glu Asp Val Arg Ser Tyr Arg Phe Pro Pro Leu Asp Lys Ile Ile
        435                 440                 445

Thr Val Ser Gly Lys Val Val Thr Glu His Arg Asn Leu Pro Ser Val
450                 455                 460

Ala Leu Lys Asp Ala Met Ser Asn Tyr Val Asp Ser Met Asp Phe Val
465                 470                 475                 480

Thr Thr Asn Asp Glu Gly Gln Ala Thr Asp Leu Pro Ile Asp Glu
            485                 490                 495

Ser Phe Ser Pro Leu Leu His Arg Ile Glu Ser Ala Val Arg Tyr Arg
            500                 505                 510

Ala Val His Pro Asn Asp Pro Val Leu Asp Pro Ser Glu Arg Leu Thr
        515                 520                 525

Glu Phe Ala His Pro Ser Glu Asp Met Val Lys Asn Ser Lys Ser His
530                 535                 540

Leu Glu Lys Leu Met Ser Ile Ala Asp Val Lys Lys Val Pro Pro Lys
545                 550                 555                 560

Thr Lys Gly Arg Lys Arg Gln Arg Glu Thr Glu Lys Pro Leu Ser Gly
                565                 570                 575

Leu Asp Val Asp Ala Leu Leu Ser Leu Glu Pro Lys Arg Thr Lys Ile
            580                 585                 590

Ser Thr Glu Asn Ala Ile Pro Glu Phe Lys Gln Thr Leu Ser Arg Ala
        595                 600                 605

Glu Asn Ile Asp Ala Ile His Asp Ala Val Gln Gln Met Ala Lys Ile
    610                 615                 620

Ile Glu Ser Gln Ile Thr His Ser Leu Gly His Ser Asn Tyr Asp Arg
625                 630                 635                 640
```

```
Val Ile Glu Gly Leu Gly Thr Met Arg Glu Glu Leu Val Asp Tyr Glu
            645             650             655

Glu Pro Ala Val Tyr Asn Asp Phe Val Arg Gln Leu Lys Gly Lys Met
            660             665             670

Leu Arg Glu Glu Leu Gly Gly Asp Arg Arg Glu Leu Trp Trp Phe Val
        675             680             685

Arg Lys Gly Lys Leu Gly Leu Ile Gly Lys Ser Glu Val Asp Ser Ser
        690             695             700

Ala Val Glu Glu Gln Glu Ala Gln Glu Phe Leu Ala Pro Asn
705             710             715
```